(12) United States Patent
Kandimalla

(10) Patent No.: US 9,950,002 B2
(45) Date of Patent: Apr. 24, 2018

(54) NANOPARTICLES/THERANOSTIC VEHICLES

(71) Applicant: Regents of the University of Minnesota, Minneapolis, MN (US)

(72) Inventor: Karunya K. Kandimalla, Rochester, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 173 days.

(21) Appl. No.: 14/487,928

(22) Filed: Sep. 16, 2014

(65) Prior Publication Data

US 2015/0078995 A1    Mar. 19, 2015

Related U.S. Application Data

(60) Provisional application No. 61/878,407, filed on Sep. 16, 2013.

(51) Int. Cl.

| | |
|---|---|
| *A61K 51/12* | (2006.01) |
| *A61K 31/726* | (2006.01) |
| *A61K 49/18* | (2006.01) |
| *A61K 49/00* | (2006.01) |
| *A61K 9/51* | (2006.01) |
| *A61K 9/00* | (2006.01) |

(52) U.S. Cl.
CPC .......... *A61K 31/726* (2013.01); *A61K 9/5161* (2013.01); *A61K 49/0002* (2013.01); *A61K 49/0043* (2013.01); *A61K 49/0056* (2013.01); *A61K 49/1863* (2013.01); *A61K 51/1244* (2013.01); *A61K 9/0019* (2013.01)

(58) Field of Classification Search
CPC ...... A61K 31/726; A61K 51/00; A61K 49/08; A61K 9/00

See application file for complete search history.

(56) References Cited

U.S. PATENT DOCUMENTS

| 5,192,535 | A | 3/1993 | Davis et al. | |
|---|---|---|---|---|
| 7,303,748 | B2 | 12/2007 | Wiegand et al. | |
| 8,257,740 | B1 * | 9/2012 | Sung | A61K 9/5161 |
| | | | | 424/488 |
| 8,673,359 | B2 * | 3/2014 | Cho | A61K 9/5026 |
| | | | | 424/497 |
| 2007/0077305 | A1 * | 4/2007 | Le | A61K 9/1652 |
| | | | | 424/488 |
| 2008/0112886 | A1 * | 5/2008 | Mitragotri | A61K 9/0097 |
| | | | | 424/9.1 |
| 2010/0226997 | A1 | 9/2010 | Bowman et al. | |

OTHER PUBLICATIONS

Edward K. Agyare et al. Development of a Smart Nano-vehicle to Target Cerebrovascular Amyloid Deposits and Brain Parenchymal Plaques Observed in Alzheimer's Disease and Cerebral Amyloid Angiopathy, Pharmaceutical Research, vol. 25(11), 2674-2684, 2008.*

Jae-Yound Je et al. Chitosan as Potential Marine Nutraceutical, Advances in Food and Nutrition Research, vol. 65, 121-135, 2012.*

"Zeroing in on the best shape for cancer-fighting nanoparticles", Methodist Hospital, Houston, [Online]. Retrieved from the Internet: <URL: http://www.sciencedaily.com/releases/2012/06/120604155600.htm>, (Jun. 4, 2012), 2 pgs.

Brambilla, D., et al., "Nanoparticles against Alzheimer's disease: PEG-PACA nanoparticles are able to link the aβ-peptide and influence its aggregation kinetic", J Control Release, 148(1), (Nov. 20, 2010), e112-3.

Gibney, Michael, et al., "Study: Disc-shaped nanoparticles best at crossing cell membranes", Published on FierceDrugDelivery (http://www.fiercedrugdelivery.com), [Online]. Retrieved from the Internet: <URL: http://www.fiercedrugdelivery.com/node/5079/print>, (Oct. 8, 2013), 2 pgs.

Greenemeier, Larry, et al., "Nanoparticles Enlisted to Impede Alzheimer's-Inducing Brain Plaque", Scientific American, [Online]. Retrieved from the Internet: <URL: http://www.scientificamerican.com/article/nanotechnology-protein-amyloid-alzheimers/>, (May 20, 2011), 2 pgs.

Hu, Y., et al., "Synthesis and characterization of chitosan-poly(acrylic acid) nanoparticles", Biomaterials, 23(15), (Aug. 2002), 3193-201.

Jaruszewski, K. M, et al., "Chitosan enhances the stability and targeting of immuno-nanovehicles to cerebro-vascular deposits of Alzheimer's disease amyloid protein", Nanomedicine, 8(2), (Feb. 2012), 250-60.

Kao, Huei-Jen, et al., "Characterization of pilocarpine-loaded chitosan/Carbopol nanoparticles", J Pharm Pharmacol., 58(2), (Feb. 2006), 179-86.

Poduslo, J. F, et al., "Targeting vascular amyloid in arterioles of Alzheimer disease transgenic mice with amyloid β protein antibody-coated nanoparticles", J Neuropathol Exp Neurol., 70(8), (Aug. 2011), 653-61.

* cited by examiner

*Primary Examiner* — Michael G Hartley
*Assistant Examiner* — Jagadishwar Samala
(74) *Attorney, Agent, or Firm* — Schwegman Lundberg & Woessner, P.A.

(57) ABSTRACT

A nanotheranostic probe and its use to facilitate diagnoses, treatment and targeting of amyloid deposits are disclosed herein.

11 Claims, 17 Drawing Sheets
(14 of 17 Drawing Sheet(s) Filed in Color)

A

B

NANOPARTICLES/THERANOSTIC VEHICLES

CROSS-REFERENCE TO RELATED APPLICATION

This application claims priority to U.S. Provisional Application Ser. No. 61/878,407, filed on Sep. 16, 2013, which is incorporated by reference herein in its entirety.

BACKGROUND

Cerebral amyloid angiopathy (CAA) is characterized by the accumulation of Aβ proteins primarily within the media and adventitia of small arteries and capillaries in the cortex and leptomeninges. About 85% of AD patients and many individuals over 60 years of age manifest CAA (Ellis, Olichney et al. 1996). Due to the lack of early diagnostic agents or biomarkers, a probable CAA diagnosis is often reached through cortical biopsies after the patient has sustained multiple lobar hemorrhages (Greenberg and Vonsattel 1997, Sakaguchi, Ueda et al. 2011). Due to sampling variability, even cortical biopsy is not specific enough to distinguish between the pathological accumulation of cerebrovascular amyloid deposits found in CAA patients and the vascular amyloid seen in normal aged brain. Hence, a definitive CAA diagnosis can currently be reached only post-mortem (Thanvi and Robinson 2006).

In addition to challenges associated with the early diagnosis, the treatment options for CAA are very few and mostly ineffective. In a sub-class of CAA patients, however, chronic treatment with immunosuppressants, like cyclophosphamide and methylprednisolone, offer symptomatic relief from cerebrovascular inflammation (Eng, Frosch et al. 2004). However, immunosuppressants exhibit systemic toxicity and severe side effects that have the potential of being worse than the disease itself. Moreover, immunosuppressant therapy does not address the underlying pathology of the disease, which is triggered by the anamolous accumulation of amyloid proteins in the cerebral vasculature.

SUMMARY

The nanovehicle described herein fills the gaps in CAA diagnosis and treatment by: i) functioning as an early diagnostic probe; ii) offering symptomatic relief from cerebrovascular inflammation; and iii) treating CAA by initiating the removal of cerebrovascular amyloid. This contribution is significant as CAA is the leading cause of brain hemorrhage and brain ischemia independent of stroke. The AD patients with CAA show more rapid decline in cognitive test performance than those without it (Cordonnier and van der Flier 2011). Hence, the multifunctional nanovehicle platform that aids in CAA diagnosis and treatment also reduces AD morbidity.

One embodiment provides a nanoparticle comprising an imaging agent, chitosan and polyacrylic acid and/or polycarbophil. In one embodiment, the imaging agent is gadolinium (Magnevist®), $^{19}F$, $^{125}I$, $^{99}Tcm$, $^{64}Cu$, or a fluorescent compound. In one embodiment, the nanoparticle has a saucer shape. In a further embodiment, the nanoparticle comprises one or more targeting agents, such as an agent that binds (e.g., an antibody that binds) amyloid deposits/plaques (e.g., a fibrillar Aβ protein, Aβ protein, or a non-toxic fragment of Aβ protein). One embodiment provides one or more therapeutic agents attached to the particles, such as an anti-inflammatory agent, anti-amyloidogenic agent, antioxidant, or immunosuppressive (these agent's include, but are not limited to, curcumin, dexamethasone or cyclophosphamide). One embodiment provides a pharmaceutical composition comprising the particles described herein and a pharmaceutically acceptable carrier.

The nanovehicle components can be released into the vascular wall in a controlled release manner (FIG. 20) and initiate the removal of cerebrovascular amyloid. Following the accumulation in the basement membrane, the nanoparticles disintegrate over time releasing cyclophosphamide, chitosan and pIgG4.1. The free chitosan can stimulate perivascular macrophages that were shown to efficiently scavenge cerebrovascular amyloid. On the other hand, IgG4.1 can initiate passive immunization therapy, which was shown to be more effective if the anti-amyloid antibodies are directly administered to the brain tissue. Supporting experimental evidence is provided in FIGS. 21 and 22.

One embodiment provides a method of treating a neurological disease and/or condition where accumulation of amyloid beta (Aβ) proteins have a role in the disease pathogenesis comprising administering an effective amount of the particles described herein or a pharmaceutical composition comprising such nanoparticles. In one embodiment, the disease and/or condition comprises cerebral amyloid angiopathy. In another embodiment, the disease and/or condition comprises Alzheimer's disease, brain hemorrhage (including microhemorrhage and lobar hemorrhages), vascular dysfunction, cerebrovascular inflammation, stroke and brain ischemia.

One embodiment provides a method to decrease expression of at least one pro-inflammatory cytokine (e.g., IL-6, IL-1β and TNF-α) comprising administering to a subject an effective amount of the particles described herein or a pharmaceutical composition comprising the particles.

Another embodiment provides a method to treat cerebral inflammation in CAA comprising administering to a subject in need thereof an effective amount of the particles described herein or a pharmaceutical composition comprising the particles.

One embodiment provides a method to increase immunostimulation in a subject comprising administering the nanoparticles described herein or a pharmaceutical composition comprising such nanoparticles to a subject so as to increase immunostimulation. In one embodiment, little or no immune response occurs in the subject's brain.

Another embodiment provides a method to increase phagocytosis of F-Aβ42 fibrils comprising administering an effective amount of the nanoparticles described herein or a pharmaceutical composition comprising the nanoparticles to a subject in need thereof, thereby increasing phagocytosis of F-Aβ42 fibrils as compared to a control or a subject administered chitosan or a targeting moiety separately and not as a component of a particle.

One embodiment provides a method to detect accumulation of amyloid beta (Aβ) proteins comprising administering the particles described herein or a pharmaceutical composition comprising the particles and imaging the subject's head. In one embodiment, the amyloid accumulation is detected in cerebral vasculature. In another embodiment, the imaging is SPECT, MRI, PET, or fluorescent imaging.

Another embodiment provides a method of preparing a nanoparticle comprising conjugating the imaging agent to chitosan, adding polyacrylic acid and/or polycarbophil to the formed imaging agent-chitosan conjugate. In one embodiment, the polyacrylic acid and/or polycarbophil entrap a therapeutic agent prior to adding to the imaging agent-chitosan conjugate. In one embodiment, a targeting moiety is conjugated to or coated on the nanoparticle. Another embodiment further provides a radiolabel.

Additionally, the nanovehicle can be customized to incorporate various targeting ligands and therapeutic agents to facilitate the diagnosis (or monitoring of disease progression or treatment for effectiveness) and treatment of other cerebrovascular pathologies.

BRIEF DESCRIPTION OF THE DRAWINGS

The patent or application file contains at least one drawing executed in color. Copies of this patent or patent application publication with color drawing(s) will be provided by the Office upon request and payment of the neccessary fee.

DETAILED DESCRIPTION

Figure 1:
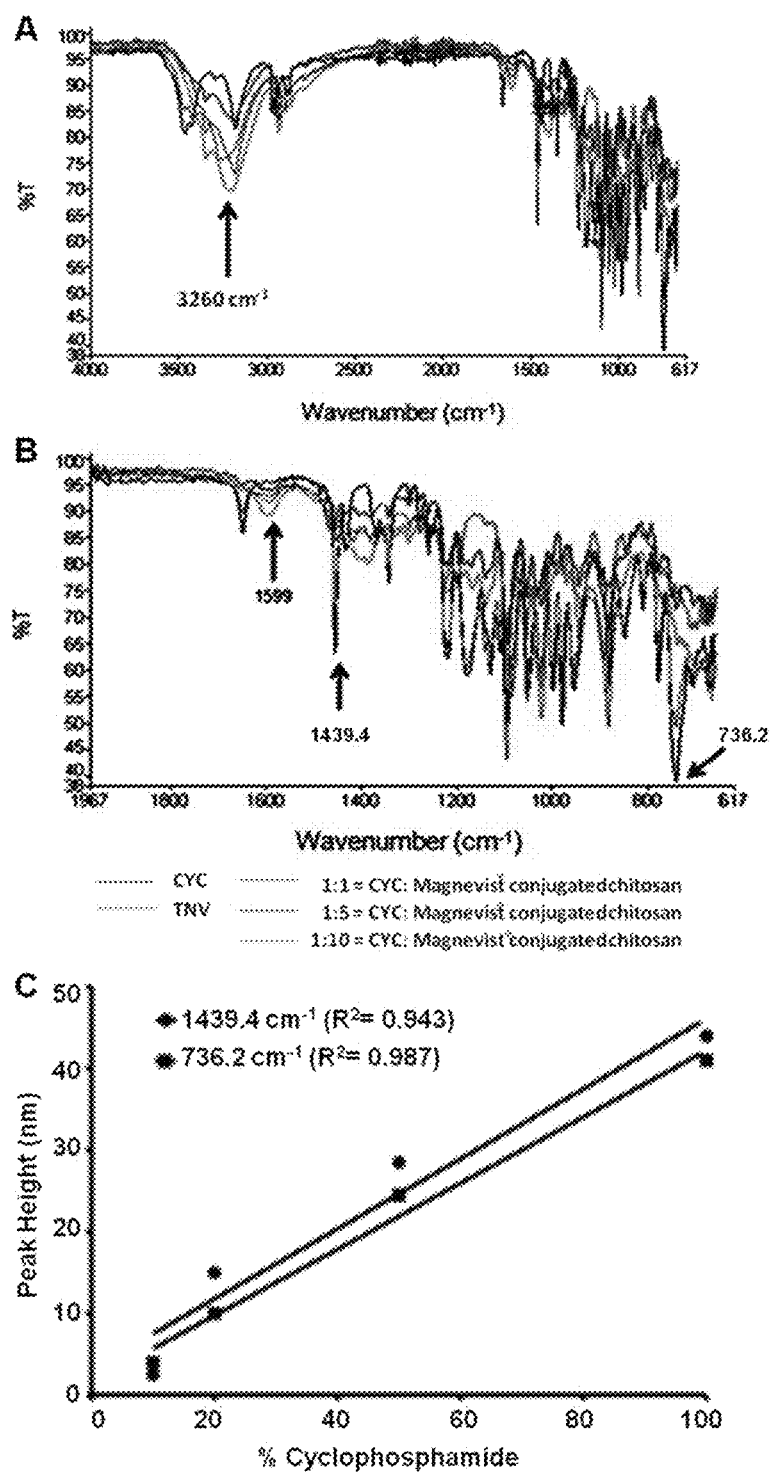
FIG. 1. Fourier transform infrared (FTIR) spectra showing the absorption peaks of cyclophosphamide (CYC); theranostic nanovehicle (TNV); 1:1=CYC:Magnevist®-conjugated chitosan (MCC); 1:4=CYC:MCC; 1:9=CYC:MCC. (A) FTIR specta between the wave numbers 617-4000 $cm^{-1}$. The absorbance peak (shown by an arrow) at 3.26K $cm^{-1}$ indicates hydroxyl groups, while the bracket outlines an absorption band between 3.1-2.7 $Kcm^{-1}$ formed by the amide bonds. (B) FTIR spectra of CYC, TNV, and various physical mixtures of cyclophosphamide and MCC between wavenumber 1967 and 617 $cm^{-1}$.

Presented herein is a theranostic nanovehicle (TNV) capable of permeating the blood brain barrier (BBB) and specifically targeting cerebrovascular amyloid. By providing MRI contrast and delivering immunosuppressants to the amyloid ridden cerebrovascular tissue, the TNVs aid in the early detection of CAA and allows for pre-symptomatic treatment.

In one embodiment, the TNVs described herein are: about 150-170 nm in particle size (small enough to permeate the BBB, yet large enough to prevent migration from the cerebrovascular basement membrane into the brain parenchyma, which allows effective targeting of Aβ proteins that accumulate within the cerebrovasculature and contribute to cerebral amyloid angiopathy); the core is hydrogel (hydrophilic and hydrophobic drugs can be entrapped (with the aid of cyclodextrans)); the surface comprises chitosan (polymer); the shape is saucer shaped (similar to a blood platelet with hydrogel in the core—this shape increases margination and the gel core generates the optimal buoyant density; with heights as low as about 10 nm); margination is very good; with regards to amyloid responsive binding to endothelial cells, TNVs marginate and demonstrate affinity to Aβ treated cell monolayer than to control monolayer and TNVs are taken up by the BBB endothelium 7-8 fold more in Aβ pretreated mice than in control mice; with regards to treatment, TNVs can carry substantial amounts of, for example, Magnevist®, as the chitosan carrying Magnevist® is covalently secured to the surface, TNVs can carry hydrophilic as well as hydrophobic drugs in the core and sustain their release over a period of about 2-3 days and TNVs show a decrease in the amyloid burden in AD transgenic mice; and/or MRI contrast throughout the cortex and hippocampus. In one embodiment, the saucer shaped nanoparticles are formed when chitosan is about 5-16 fold excess to polycarbophil. In another embodiment, the ratio of polycarbophil to chitosan is 1:5. This ratio produced smaller particles with a positively charged surface. In one embodiment, the TNVs had a gel core of polycarbophil that is negatively charged and an outside ring of chitosan, which is positively charged. The positively charged surface enables the nanoparticle to interact with the negatively charged endothelial cells surface. In another embodiment, a ratio of 1:5 polycarbophil to chitosan (form saucer-shaped TNVs) is stirred at 700 rpm, such that TNVs are spontaneously formed. Then, the nanoparticle is cross-linked (e.g., cross-link the chitosan to the polycarbophil) using, for example, a 1-step carbodiimide conjugation procedure that also accomplishes the conjugation of anti-amyloid antibody to the nanocore surface. The ratio allows for the optimal size and charge. Moreover, cross-linking the TNV prevents it from falling apart at the physiological pH.

Definitions

In describing and claiming the invention, the following terminology will be used in accordance with the definitions set forth below.

The articles "a" and "an" are used herein to refer to one or to more than one (i.e., to at least one) of the grammatical object of the article. By way of example, "an element" means one element or more than one element.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 20% of the numerical value of the number with which it is being used. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about."

As use herein, the terms "administration of" and or "administering" a compound should be understood to mean providing a compound of the invention or a prodrug of a compound of the invention to a subject in need of treatment.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and $F(ab)_2$, as well as single chain antibodies and humanized antibodies.

The term "antibody" refers to polyclonal and monoclonal antibodies and derivatives thereof (including chimeric, synthesized, humanized and human antibodies), including an entire immunoglobulin or antibody or any functional fragment of an immunoglobulin molecule which binds to the target antigen and or combinations thereof. Examples of such functional entities include complete antibody molecules, antibody fragments, such as Fv, single chain Fv, complementarity determining regions (CDRs), VL (light chain variable region), VH (heavy chain variable region), Fab, $F(ab')_2$ and any combination of those or any other functional portion of an immunoglobulin peptide capable of binding to target antigen.

The term "biocompatible", as used herein, refers to a material that does not elicit a substantial detrimental response in the host.

As used herein, the term "biologically active fragments" or "bioactive fragment" of the polypeptides encompasses natural or synthetic portions of the full length protein that are capable of specific binding to their natural ligand or of performing the function of the protein.

The term "biological sample," as used herein, refers to samples obtained from a subject, including, but not limited to, skin, hair, tissue, blood, plasma, cells, sweat and urine.

Accumulation of amyloid proteins including an increase in amount or in a form not normally present in subjects without disease associated with amyloid proteins. Amyloids are insoluble fibrous protein aggregates sharing specific structural traits. They arise from at least 18 inappropriately folded versions of proteins and polypeptides present naturally in the body. These misfolded structures alter their proper configuration such that they erroneously interact with one another or other cell components forming insoluble fibrils. They have been associated with the pathology of more than 20 serious human diseases in that, abnormal accumulation of amyloid fibrils in organs may lead to amyloidosis, and may play a role in various neurodegenerative disorders, including, but not limited to, Alzheimer's disease, Parkinson's disease, transmissible spongiform encephalopathy, fatal familial insomnia, Huntington's disease, familial amyloid polyneuropathy, cerebral amyloid angiopathy, systemic AL amyloidosis, and multiple myeloma.

"Cytokine," as used herein, refers to intercellular signaling molecules, the best known of which are involved in the regulation of mammalian somatic cells. A number of families of cytokines, both growth promoting and growth inhibitory in their effects, have been characterized including, for example, interleukins, interferons, and transforming growth factors. A number of other cytokines are known to those of skill in the art. The sources, characteristics, targets and effector activities of these cytokines have been described.

The use of the word "detect" and its grammatical variants refers to measurement of the species without quantification, whereas use of the word "determine" or "measure" with their grammatical variants are meant to refer to measurement of the species with quantification. The terms "detect" and "identify" are used interchangeably herein.

As used herein, a "detectable marker" or a "reporter molecule" is an atom or a molecule that permits the specific detection of a compound comprising the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence polarization or altered light scattering.

As used herein, the term "diagnosis" refers to detecting amyloid proteins.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, an "effective amount" or "therapeutically effective amount" means an amount sufficient to produce a selected effect, such as alleviating symptoms of a disease or disorder.

As used herein, a "functional" biological molecule is a biological molecule in a form in which it exhibits a property by which it is characterized. A functional enzyme, for example, is one which exhibits the characteristic catalytic activity by which the enzyme is characterized.

The term "immunologically active fragments thereof" will generally be understood in the art to refer to a fragment of a polypeptide antigen comprising at least an epitope, which means that the fragment at least comprises 4 contiguous amino acids from the sequence of the polypeptide antigen.

The term "inhibit," as used herein, refers to the ability of a compound, agent, or method to reduce or impede a described function, level, activity, rate, etc., based on the context in which the term "inhibit" is used. Preferably, inhibition is by at least 10%, more preferably by at least 25%, even more preferably by at least 50%, and most preferably, the function is inhibited by at least 75%. The term "inhibit" is used interchangeably with "reduce" and "block."

The term "pharmaceutical composition" shall mean a composition comprising at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

As used herein, the term "pharmaceutically-acceptable carrier" means a chemical composition with which an appropriate compound or derivative can be combined and which, following the combination, can be used to administer the appropriate compound to a subject.

"Pharmaceutically acceptable" means physiologically tolerable, for either human or veterinary application.

As used herein, "pharmaceutical compositions" include formulations for human and veterinary use.

"Plurality" means at least two.

The term "prevent," as used herein, means to stop something from happening, or taking advance measures against something possible or probable from happening. In the context of medicine, "prevention" generally refers to action taken to decrease the chance of getting a disease or condition.

A "preventive" or "prophylactic" treatment is a treatment administered to a subject who does not exhibit signs, or exhibits only early signs, of a disease or disorder. A prophylactic or preventative treatment is administered for the purpose of decreasing the risk of developing pathology associated with developing the disease or disorder.

The term "standard," as used herein, refers to something used for comparison. For example, it can be a known standard agent or compound which is administered and used for comparing results when administering a test compound or it can be a standard parameter or function which is measured to obtain a control value when measuring an effect of an agent or compound on a parameter or function. Standard can also refer to an "internal standard", such as an agent or compound which is added at known amounts to a sample and is useful in determining such things as purification or recovery rates when a sample is processed or subjected to purification or extraction procedures before a marker of interest is measured. Internal standards are often a purified marker of interest which has been labeled, such as with a radioactive isotope, allowing it to be distinguished from an endogenous marker.

A "subject" of analysis, diagnosis, or treatment is an animal. Such animals include mammals, preferably a human.

As used herein, a "subject in need thereof" is a patient, animal, mammal, or human, who will benefit from the method of this invention.

The terms nanoparticle, nanovehicle or particle as used herein are interchangeable unless specifically stated otherwise.

The term "symptom," as used herein, refers to any morbid phenomenon or departure from the normal in structure, function, or sensation, experienced by the patient and indicative of disease. In contrast, a "sign" is objective evidence of disease. For example, a bloody nose is a sign. It is evident to the patient, doctor, nurse and other observers.

A "therapeutic" treatment is a treatment administered to a subject who exhibits signs of pathology for the purpose of diminishing or eliminating those signs.

EMBODIMENTS

The present invention relates to nanotheranostic particles and their use to facilitate diagnoses, treatment and targeting of amyloid proteins/deposits is disclosed herein.

A. Nanoparticles

A nanoparticle comprising an imaging agent, chitosan and polyacrylic acid and/or polycarbophil. The particles can further comprise one or more targeting agents and/or one or more therapeutic agents.

B. Targeting Moiety

By having targeting moieties, the particles are able to efficiently bind to or otherwise associate with a biological entity, for example, a cell surface protein. Targeting of a therapeutic agent (e.g., to a particular tissue or cell type, to a specific diseased tissue but not to normal tissue, etc.) is desirable for the treatment of tissue specific diseases. For example, in contrast to systemic delivery of a cytotoxic agent, targeted delivery could prevent the agent from killing healthy cells. Additionally, targeted delivery would allow for the administration of a lower dose of the agent, which could reduce any undesirable side effects.

In some embodiments, a targeting moiety may be an antibody and/or characteristic portion thereof. Antibodies refer to polypeptides substantially encoded by an immunoglobulin gene or immunoglobulin genes, or fragments thereof, which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively.

A variety of methods for producing polyclonal and monoclonal antibodies are known in the art. See, e.g., Goding, MONOCLONAL ANTIBODIES; PRINCIPLES AND PRACTICE, Academic Press, 2nd Edition (1986); and Harlow & Lane. A monoclonal antibody directed against or reactive with, for example, human cells expressing a desired antigen is obtained by using combinations of immunogens to immunize mice and screening hybridoma supernatant against cells which express the desired antigen or by a screening assay designed to be specific for monoclonal antibodies directed against the antigen of interest. Useful cell lines for screening for the antibodies of this invention are readily available or obtained. Such cells include the Burkitt's lymphoma cell lines Daudi, and Raji.

Recombinant DNA methodologies can be used to synthesize antibodies of this invention. For example, an antibody portion of an immunotoxin for use in humans is a "humanized" antibody against a cell antigen which contains murine complementarity-determining regions (CDRs) combined with human variable region frameworks and human constant regions.

Humanized (chimeric) antibodies are immunoglobulin molecules comprising a human and non-human portion. More specifically, the antigen combining region (or variable region) of a humanized chimeric antibody is derived from a non-human source (e.g., murine) and the constant region of the chimeric antibody (which confers biological effector function to the immunoglobulin) is derived from a human source. The humanized chimeric antibody should have the antigen binding specificity of the non-human antibody molecule and the effector function conferred by the human antibody molecule. A large number of methods of generating chimeric antibodies are well known to those of skill in the art (see, e.g., U.S. Pat. Nos. 5,502,167, 5,500,362, 5,491,088, 5,482,856, 5,472,693, 5,354,847, 5,292,867, 5,231,026, 5,204,244, 5,202,238, 5,169,939, 5,081,235, 5,075,431, and 4,975,369). Detailed methods for preparation of chimeric (humanized) antibodies can be found in U.S. Pat. No. 5,482,856.

In another embodiment, this invention provides for fully human antibodies. Human antibodies consist entirely of characteristically human polypeptide sequences. The human antibodies of this invention can be produced in using a wide variety of methods (see, e.g., Larrick et al, U.S. Pat. No. 5,001,065, for review).

The antibody moieties of this invention can be single chain antibodies which refers to an antibody wherein the genetic information encoding the functional fragments of the antibody are located in a single contiguous length of DNA. For a thorough description of single chain antibodies, see Bire, et al., Science 242:423 (1988) and Huston, et al., Proc. Nat'l Acad. Sci. USA 85:5879 (1988).

Antibodies directed against proteins, polypeptides, or peptide fragments thereof of the invention may be generated using methods that are well known in the art. For instance, U.S. patent application Ser. No. 07/481,491, which is incorporated by reference herein in its entirety, discloses methods of raising antibodies to peptides. For the production of antibodies, various host animals, including but not limited to rabbits, mice, and rats, can be immunized by injection with a polypeptide or peptide fragment thereof. To increase the immunological response, various adjuvants may be used depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*.

In one embodiment, antibodies, or antisera, directed against amyloid protein or a homolog or fragment thereof, are useful for targeting amyloid protein for diagnostic and therapeutic purposes.

Fragments of amyloid protein may be generated and antibodies prepared against the fragments. Assays are provided herein to determine whether an antibody directed against amyloid protein, or a fragment thereof, have the ability to detect amyloid protein or inhibit its formation.

For the preparation of monoclonal antibodies, any technique which provides for the production of antibody molecules by continuous cell lines in culture may be utilized. For example, the hybridoma technique originally developed by Kohler and Milstein (1975, Nature 256:495-497), the trioma technique, the human B-cell hybridoma technique (Kozbor et al., 1983, Immunology Today 4:72), and the EBV-hybridoma technique (Cole et al., 1985, in Monoclonal Antibodies and Cancer Therapy, Alan R. Liss, Inc., pp. 77-96) may be employed to produce human monoclonal antibodies. In another embodiment, monoclonal antibodies are produced in germ-free animals.

In accordance with the invention, human antibodies may be used and obtained by utilizing human hybridomas (Cote et al., 1983, Proc. Natl. Acad. Sci. U.S.A. 80:2026-2030) or by transforming human B cells with EBV virus in vitro (Cole et al., 1985, in Monoclonal Antibodies and Cancer Therapy, Alan R. Liss, Inc., pp. 77-96). Furthermore, techniques developed for the production of "chimeric antibodies" (Morrison et al., 1984, Proc. Natl. Acad. Sci. U.S.A. 81:6851-6855; Neuberger et al., 1984, Nature 312:604-608; Takeda et al., 1985, Nature 314:452-454) by splicing the genes from a mouse antibody molecule specific for epitopes of SLLP polypeptides together with genes from a human antibody molecule of appropriate biological activity can be employed; such antibodies are within the scope of the present invention. Once specific monoclonal antibodies have been developed, the preparation of mutants and variants thereof by conventional techniques is also available.

In one embodiment, techniques described for the production of single-chain antibodies (U.S. Pat. No. 4,946,778, incorporated by reference herein in its entirety) are adapted to produce protein-specific single-chain antibodies. In another embodiment, the techniques described for the construction of Fab expression libraries (Huse et al., 1989, Science 246:1275-1281) are utilized to allow rapid and easy identification of monoclonal Fab fragments possessing the desired specificity for specific antigens, proteins, derivatives, or analogs of the invention.

Antibody fragments which contain the idiotype of the antibody molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment; the Fab fragments which can be generated by treating the antibody molecule with papain and a reducing agent; and Fv fragments.

The generation of polyclonal antibodies is accomplished by inoculating the desired animal with the antigen and isolating antibodies which specifically bind the antigen therefrom.

In the production of antibodies, screening for the desired antibody can be accomplished by techniques known in the art, e.g., ELISA (enzyme-linked immunosorbent assay). Antibodies generated in accordance with the present invention may include, but are not limited to, polyclonal, monoclonal, chimeric (i.e., "humanized"), and single chain (recombinant) antibodies, Fab fragments, and fragments produced by a Fab expression library.

C. Therapeutic Agent Delivery for Treatment or Contrast Agent for Diagnostic

According to the present invention, any agents ("payload"), including, for example, therapeutic agents (e.g. anti-amyloid agents), diagnostic agents (e.g. contrast agents; radionuclides; and fluorescent, luminescent, and magnetic moieties), prophylactic agents (e.g. vaccines), nutraceutical agents (e.g. vitamins, minerals, antioxidants etc.), anti-inflammatory agents, immunosuppressants, and/or anti-amyloidogenic agents may be delivered by the particles of the invention. Exemplary agents to be delivered in accordance with the present invention include, but are not limited to, small molecules (e.g. cytotoxic agents), nucleic acids (e.g., siRNA, RNAi, and mircoRNA agents), proteins (e.g. antibodies), peptides, lipids, carbohydrates, hormones, metals, radioactive elements and compounds, drugs, vaccines, immunological agents, etc., and/or combinations thereof. In some embodiments, the agent to be delivered is an agent useful in the treatment or diagnosis of CAA and/or Alzheimer's disease.

For instance, the targeting moiety may target or cause the particle to become localized at specific portions within a subject, and the payload may be delivered to those portions. In a particular embodiment, the drug or other payload is released in a controlled release manner from the particle and allowed to interact locally with the particular targeting site. The term "controlled release" (and variants of that term) as used herein (e.g., in the context of "controlled-release system") is generally meant to encompass release of a substance (e.g., a drug) at a selected site or otherwise controllable in rate, interval, and/or amount. Controlled release encompasses, but is not necessarily limited to, substantially continuous delivery, patterned delivery (e.g., intermittent delivery over a period of time that is interrupted by regular or irregular time intervals), and delivery of a bolus of a selected substance (e.g., as a predetermined, discrete amount if a substance over a relatively short period of time (e.g., a few seconds or minutes)).

Non-limiting examples of potentially suitable drugs/payloads include the antibody itself, imaging agents, such as gadolinium (Magnevist®), $^{125}$I, $^{99}$Tcm, $^{64}$Cu and/or a fluorescent compound, anti-inflammatory agent, anti-amyloidogenic agent, anti-oxidant, or immunosuppressive (including for example, dexamethasone or cyclophosphamide).

D. Methods of Treatment

In some embodiments, the particles in accordance with the present invention may be used to treat, alleviate, ameliorate, relieve, delay onset of, inhibit progression of, reduce severity of, and/or reduce incidence of one or more symptoms or features of a disease, disorder, and/or condition. In some embodiments, inventive particles may be used to treat a neurological disease and/or condition where accumulation of amyloid beta (Aβ) proteins have a role in the disease pathogenesis, such as cerebral amyloid angiopathy.

Diseases and/or conditions where accumulation of amyloid beta (Aβ) proteins have a role in the disease pathogenesis also includes Alzheimer's Disease, brain hemorrhage (including microhemorrhage and lobar hemorrhages), vascular dysfunction, cerebrovascular inflammation, stroke and brain ischemia.

In one embodiment, the particles may be used to decrease the expression of at least one pro-inflammatory cytokine (e.g., IL-6, IL-1β and TNF-α) as compared to a control or a control subject. In another embodiment, the particles may be used to treat cerebral inflammation in CAA.

E. Pharmaceutical Compositions

The present invention also relates to a pharmaceutical composition comprising the nanoparticles of the present invention in a pharmaceutically acceptable carrier. In therapeutic applications, compositions are administered to a patient suffering from a disease, in an amount sufficient to cure or at least partially arrest the disease and its complications. An amount adequate to accomplish this is defined as a therapeutically effective dose. Amounts effective for this use will depend on the severity of the disease and the general state of the patient's health.

The nanoparticles of the present invention may be administered by various means appropriate for different purposes. As used herein "injecting or applying" includes administration of a compound of the invention by any number of routes and means including, but not limited to, topical, oral, buccal, intravenous, intramuscular, intra arterial, intramedullary, intrathecal, intraventricular, transdermal, subcutaneous, intraperitoneal, intranasal, enteral, topical, sublingual, vaginal, ophthalmic, pulmonary, or rectal means.

Advantageously, the pharmaceutical composition is suitable for parenteral administration. As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, and intrasternal injection Single or multiple administrations of the compositions may be administered depending on the dosage and frequency as required and tolerated by the patient. In any event, the composition should provide a sufficient quantity of the proteins of this invention to effectively treat the patient.

The compositions for administration will commonly comprise a solution of the particles in a pharmaceutically acceptable carrier. As used herein, the term "pharmaceutically acceptable carrier" means a non-toxic, inert solid, semi-solid or liquid filler, diluent, encapsulating material or formulation auxiliary of any type. Remington's Pharmaceutical Sciences. Ed. by Gennaro, Mack Publishing, Easton, Pa., 1995 discloses various carriers used in formulating pharmaceutical compositions and known techniques for the preparation thereof. Some examples of materials which can serve as pharmaceutically acceptable carriers include, but are not limited to, sugars such as lactose, glucose, and sucrose; starches such as corn starch and potato starch; cellulose and its derivatives such as sodium carboxymethyl cellulose, ethyl cellulose, and cellulose acetate; powdered tragacanth;

malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as TWEEN™80; pH adjusting and buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. If filtration or other terminal sterilization methods are not feasible, the formulations can be manufactured under aseptic conditions. The concentration of nanoparticle in these formulations can vary widely, and will be selected primarily based on fluid volumes, viscosities, body weight and the like in accordance with the particular mode of administration selected and the patient's needs.

It will be appreciated that the exact dosage of the nanoparticles etc disclosed herein is chosen by the individual physician in view of the patient to be treated, in general, dosage and administration are adjusted to provide an effective amount of the particle to the patient being treated. As used herein, the "effective amount" of a particle refers to the amount necessary to elicit the desired biological response. As will be appreciated by those of ordinary skill in this art, the effective amount of a particle may vary depending on such factors as the desired biological endpoint, the drug to be delivered, the target tissue, the route of administration, etc. Additional factors which may be taken into account include the severity of the disease state; age, weight and gender of the patient being treated; diet, time and frequency of administration; drug combinations; reaction sensitivities; and tolerance/response to therapy and or diagnostic.

The nanoparticles of the invention may be formulated in dosage unit form for ease of administration and uniformity of dosage. The expression "dosage unit form" as used herein refers to a physically discrete unit of nanoparticle appropriate for the patient to be treated. It will be understood, however, that the total daily usage of the compositions of the present invention will be decided by the attending physician within the scope of sound medical judgment. For any nanoparticle, the therapeutically effective dose can be estimated initially either in cell culture assays or in animal models, usually mice, rabbits, dogs, or pigs. The animal model is also used to achieve a desirable concentration range and route of administration. Such information can then be used to determine useful doses and routes for administration in humans. Therapeutic efficacy and toxicity of nanoparticles can be determined by standard pharmaceutical procedures in cell cultures or experimental animals, e.g., $ED_{50}$ (the dose is therapeutically effective in 50% of the population) and $LD_{50}$ (the dose is lethal to 50% of the population). The dose ratio of toxic to therapeutic effects is the therapeutic index, and it can be expressed as the ratio, $LD_{50}/ED_{50}$. Pharmaceutical compositions which exhibit large therapeutic indices may be useful in some embodiments. The data obtained from cell culture assays and animal studies can be used in formulating a range of dosage for human use.

The present invention also provides any of the above-mentioned compositions in kits, optionally with instructions for administering any of the compositions described herein by any suitable technique as previously described, for example, orally, intravenously, pump or implantable delivery device, or via another known route of drug delivery. "Instructions" can define a component of promotion, and typically involve written instructions on or associated with packaging of compositions of the invention. Instructions also can include any oral or electronic instructions provided in any manner. The "kit" typically defines a package including any one or a combination of the compositions of the invention and the instructions, but can also include the composition of the invention and instructions of any form that are provided in connection with the composition in a manner such that a clinical professional will clearly recognize that the instructions are to be associated with the specific composition.

The kits described herein may also contain one or more containers, which may contain the inventive composition and other ingredients as previously described. The kits also may contain instructions for mixing, diluting, and/or administrating the compositions of the invention in some cases. The kits also can include other containers with one or more solvents, surfactants, preservative and/or diluents (e.g., normal saline (0.9% NaCl), or 5% dextrose) as well as containers for mixing, diluting or administering the components in a sample or to a subject in need of such treatment.

The compositions of the kit may be provided as any suitable form, for example, as liquid solutions or as dried powders. When the composition provided is a dry powder, the composition may be reconstituted by the addition of a suitable solvent, which may also be provided. In embodiments where liquid forms of the composition are used, the liquid form may be concentrated or ready to use. The solvent will depend on the nanoparticle and the mode of use or administration. Suitable solvents for drug compositions are well known, for example as previously described, and are available in the literature. The solvent will depend on the nanoparticle and the mode of use or administration.

The invention also involves, in another aspect, promotion of the administration of any of the nanoparticle described herein. In some embodiments, one or more compositions of the invention are promoted for the prevention or treatment of various diseases such as those described herein via administration of any one of the compositions of the present invention. As used herein, "promoted" includes all methods of doing business including methods of education, hospital and other clinical instruction, pharmaceutical industry activity including pharmaceutical sales, and any advertising or other promotional activity including written, oral and electronic communication of any form, associated with compositions of the invention.

The invention is now described with reference to the following Examples and Embodiments. Without further description, it is believed that one of ordinary skill in the art can, using the preceding description and the following illustrative examples, make and utilize the present invention and practice the claimed methods. The following working examples therefore, are provided for the purpose of illustration only and specifically point out the preferred embodiments of the present invention, and are not to be construed as limiting in any way the remainder of the disclosure. Therefore, the examples should be construed to encompass any and all variations which become evident as a result of the teaching provided herein.

EXAMPLES

Example 1

Theranostic Nanovehicles Capable of Targeting Cerebrovascular Amyloid Deposits

Introduction

Cerebral amyloid angiopathy (CAA) is characterized by the deposition of amyloid beta (Aβ) proteins within the walls of small to medium-sized blood vessels of the brain and leptomeninges. About 80% of Alzheimer's disease (AD) patients manifest some degree of CAA [1]. Several studies have demonstrated that AD patients with CAA show worst cognitive test performance during life [2-4]. In addition to causing cerebrovascular inflammation, CAA triggers vascular dysfunction, which is believed to accelerate AD progression [5-7]. If detected in the early stages, the vascular inflammation resulting from CAA can be treated using immunosuppressants such as cyclophosphamide [8]. However, cyclophosphamide has narrow therapeutic index and long-term cyclophosphamide administration via conventional routes is associated with severe side effects.

On the other hand, a definitive diagnosis of CAA requires pathological examination of the affected tissue, which is very invasive [9]. Computerized axial tomography (CT) is commonly used to detect CAA. However, due to low sensitivity of CT, only advanced stages of CAA associated with acute stroke and massive hemorrhages can be detected. Theoretically, magnetic resonance imaging (MRI) has sufficient spatial and contrast resolution to visualize cerebrovascular amyloid deposits. However, visualization of deposits less than 35 μm in diameter will require contrast enhancement. Due to the lack of effective contrast agents, clinicians currently make a probable diagnosis of CAA based on the occurrence of strictly lobar hemorrhages, particularly in the cortico-subcortical area, detected by T2*-weighted MRI [10]. Unfortunately, these hemorrhages occur in the advanced stages of CAA, when the opportunities of intervention are limited [11].

Presented herein is a theranostic nanovehicle (TNV) capable of permeating the blood brain barrier (BBB) and specifically targeting cerebrovascular amyloid. By providing MRI contrast and delivering immunosuppressants to the amyloid ridden cerebrovascular tissue, the TNVs aid in the early detection of CAA and allows for pre-symptomatic treatment.

Abbreviations

CAA, cerebral amyloid angiopathy; Aβ, amyloid beta; TNV, theranostic nanovehicle; MRI, magnetic resonance imaging; CYC, cyclophosphamide; pIgG4.1, putrescein modified anti-amyloid antibody IgG4.1; CCN, control chitosan nanoparticles; BBB, blood brain barrier; AD, Alzheimer's disease; CT, computerized axial tomography; TPP, pentasodium tripolyphosphate; DMEM/F12, Dulbecco's modified eagle medium and F-12 nutrient mixture 50:50; EDC, 1-ethyl-3-(3 dimethylaminopropyl) carbodiimide; NHS, N-hydroxyl-succinimide; Gd-DTPA, gadopentetate dimeglumine; BBMVE, bovine brain microvascular endothelial; MWCO, molecular weight cut off; FTIR, fourier-transformed infrared spectroscopy; BSA, bovine serum albumin; SEM, standard error of the mean; HPLC, high performance liquid chromatography; Gd, gadolinium; QCM-D, quartz crystal microbalance-dissipation; ELISA, enzyme linked immunosorbent assay; HBSS, hanks balanced salt solution; kel, elimination rate constant; AUC, area under the curve; Cl, clearance; Vss, volume of steady state; SPECT, single photon emission computerized tomography; SE, spin-echo; TR, repetition times; TE, echo times; GRE, gradient recalled echo; ROIs, regions of interest; PFA, paraformaldehyde; MCC; Magnevist®-conjugated chitosan; IL-6, interleukin-6; IL-1β, interleukin-1beta; TNF-α, tumor necrosis factor-alpha.

Materials and Methods

Materials

Medium molecular weight chitosan with degree of deacetylation around 84%, pentasodium tripolyphosphate (TPP), donor horse serum, heparin and gentamicin sulphate were purchased from Sigma-Aldrich (St. Louis, USA). Dulbecco's modified eagle medium and F-12 nutrient mixture 50:50 (DMEM/F-12), Ultra-pure agarose, 1-ethyl-3-(3 dimethylaminopropyl) carbodiimide (EDC), and N-hydroxyl-succinimide (NHS) were procured from Invitrogen, (Carlsbad, Calif.). Cyclophosphamide was purchased from MP Biomedicals (Solon, Ohio). Magnevist® containing 469 mg/ml gadopentetate dimeglumine (Gd-DTPA) was procured from Berlex Laboratories (Montville, N.J.).

Animals

B6SJLF1/J mice were obtained from Harlan Laboratories Inc. (Madison, Wis.) at 6-8 weeks of age and maintained in a virus-free, light and temperature controlled barrier environment until 12-14 months old. The animals were provided with standard pellets diet and water ad libitum. All procedures with the mice were performed in accordance with the National Institutes of Health Guide for the Care and Use of Laboratory Animals and were approved by the Mayo Institutional Animal Care and Use Committee.

In Vitro Cell Culture

Primary bovine brain microvascular endothelial (BBMVE) cells were obtained frozen from the Cell Applications Inc. (San Diego, Calif.). The cells were cultured in a gelatin coated flask (75 cm2) at 37° C. under humidified air with 5% $CO_2$ according to the protocols outlined in our earlier publications [12]. The growth medium constituted of 90% DMEM/F-12 and 10% donor horse serum supplemented with 10 mM HEPES, 13 mM sodium bicarbonate, 100 μg/ml heparin and 50 μg/ml Gentamicin sulphate.

In Vitro BBB Model

The filter membrane (pore size=0.4 μm) of each 24 mm Transwell® insert (Costar, Cambridge, Mass.) was coated with 0.01% rat tail collagen (type 1) followed by 0.01% bovine fibronectin. The BBMVE cells were then seeded on the filter membrane at a density of approximately 80,000 cells/cm². The growth medium was added to both donor (1.5 ml) and receiver compartments (2.5 ml) and incubated at 37° C. under humidified air containing 5% $CO_2$. The medium was changed every other day for 13-15 days until the polarized monolayers were formed. High transendothelial electrical resistance values, which are characteristic of well-formed polarized BBMVE cell monolayers, were ascertained using 'chopstick' electrodes attached to a Millicell-ERS meter (Millipore Corp., Bedford, Mass.). Monolayers with mean TEER values greater than 170 Ω×cm² were selected for this study.

Preparation of TNVs

Modification of IgG4.1 or F(ab')₂ Fragments of IgG4.

The monoclonal antibody IgG4.1 or F(ab')₂ portion of IgG4.1 was cationized with putrescine (1,4-butanediamine) using carbodiimide chemistry. The pIgG4.1 or pF(ab')₂4.1 thus formed was concentrated in Vivaspin with 30-kDa molecular weight cut off (MWCO) filter.

Preparation of Magnevist®-Conjugated Chitosan

MRI contrast agent, Magnevist®, was attached to chitosan as described previously [13, 14]. The Magnevist® conjugated chitosan solution thus obtained was lyophilized for later use. The presence of amide bond that signifies the successful conjugation of Magnevist® to chitosan was verified by fourier-transformed infrared spectroscopy (FTIR).

TNV Formulation

The cyclophosphamide was entrapped in the nanoparticle made from Magnevist®-conjugated chitosan using ionic gelation with TPP. The surface of the nanoparticle was conjugated with pIgG4.1 or pF(ab')$_2$4.1 using carbodiimide chemistry. The TNVs thus formed were separated from the free cyclophosphamide and pIgG4.1 or F(ab')$_2$4.1 by ultracentrifugation at 20,000 rpm for 15 min. The supernatant was discarded and the pellets were re-suspended in PBS. The control chitosan nanoparticles (CCN) were prepared in a similar fashion except that they were conjugated with bovine serum albumin (BSA).

Radioiodination of TNV

The TNVs were labeled with carrier-free Na$^{125}$I, using the chloramine-T procedure as described previously [15]. Free radioactive iodine was separated from the radiolabeled TNVs by dialysis against 0.01 M phosphate-buffered saline at pH 7.4. The CCNs were also labeled with $^{125}$I using the same procedure.

TNV Characterization

Particle Size and Zeta Potential of TNVs

The mean hydrodynamic diameter of TNVs dispersed in distilled water was determined using photon correlation spectroscopy (Particle sizer; Brookhaven Instruments, N.Y., US), whereas the zeta potential was determined by laser doppler anemometry (Zeta Potential Analyzer, Brookhaven Instruments, N.Y., US). The aqueous TNV suspensions were diluted with distilled water before analysis. The analyses were performed on three independently prepared samples and the mean±standard error of the mean (SEM) was reported.

Encapsulation and Release of Cyclophosphamide from TNVs

To quantify the amount of cyclophosphamide incorporated in TNVs, mixtures of cyclophosphamide and lyophilized blank nanoparticles made from Magnevist®-conjugated chitosan were prepared in the ratio of 1:1, 1:5 and 1:10, respectively. The IR spectra (500-4000 cm$^{-1}$) for each component, the mixtures, and the TNVs were acquired using FTIR spectrophotometer (Perkin Elmer Life and Analytical Sciences, Connecticut). Cyclophosphamide absorbance peaks that are distinct from the blank nanoparticles were selected and a standard curve of the peak height versus cyclophosphamide percentage was constructed. The percentage of unknown amount of cyclophosphamide in the TNVs was determined from the standard curve.

To evaluate cyclophosphamide release from the TNVs, 30 mg of lyophilized TNVs were re-suspended in 3 ml distilled water and placed in a dialysis bag (MWCO=12.5 kDa), which was then immersed completely in a trough containing 50 ml PBS maintained at 37° C. The trough contents were stirred constantly at 150 rpm, sampled at predetermined time intervals (0, 0.25, 0.5, 0.75, 1, 2, 3, 6, 14, 18 hrs), and was replaced with the same volume of fresh PBS. The amount of cyclophosphamide in the collected samples was determined using the high performance liquid chromatography (HPLC) method reported previously [16]. The cyclophosphamide peak was separated on C18 column (5 μm, 4.6 mm×150 mm ID) with mobile phase constituting of 77.25% acetonitrile and 22.75% of 10 mM potassium phosphate buffer (pH=6) and run at a flow rate of 1.3 ml/min. The cyclophosphamide peak exhibiting retention time of 4.9 min was detected at 192 nm using photo diode array detector.

Gadolinium Content in TNV

Gadolinium (Gd) content in TNVs was determined as per the previously published arsenazo III colorimetric method [17, 18].

Ability of TNVs to Bind to Aβ Fibrils

Quartz crystal microbalance-dissipation (QCM-D) was used to study the ability of TNVs to bind to pre-formed Aβ40 fibrils.

Aβ Fibril Formation

To form Aβ fibrils, 1 mg/ml monomeric Aβ40 solution was prepared, filtered through 0.22 μm filter, and the filtrate was agitated at 250 rpm on orbital shaker for 48 hrs at 37° C. The fibrils thus obtained were sonicated for 60 seconds and diluted with distilled water to obtain 0.5 mg/ml Aβ fibril suspensions.

Adsorption of Aβ40 Fibrils to the Crystal

The gold/quartz crystal surface was equilibrated with distilled water and then Aβ40 fibril suspension (0.5 mg/ml) was flown over the crystal at a flow rate of 100 μl/min. The binding of Aβ40 fibrils to the gold surface was monitored by recording the frequency changes in the gold/quartz crystal sensors and the flow of Aβ40 fibril suspension was continued until the frequency plateaued. Distilled water was again flown over the crystal for 10 min to remove the loosely bound Aβ40 fibrils.

Binding of TNVs to Adsorbed Aβ40 Fibril Bed on the Gold Quartz Crystal

TNV or CCN suspension (10 mg/ml) was flown over the Aβ40 fibril bed adsorbed to the gold/quartz crystal. The mass of Aβ40 fibrils adsorbed on the quartz crystal or TNVs bound to the pre-adsorbed Aβ40 fibrils on the crystal was calculated as follows:

$$\Delta m = -\frac{C\Delta f}{n} \quad (1)$$

where C is the mass sensitivity constant (C=17.7 ng cm$^{-2}$ Hz$^{-1}$ at f=5 MHz), n is the harmonic (overtones) number and Δf is the change in frequency.

The Uptake of TNVs by In Vitro BBB

The in vitro CAA model was prepared by pre-incubating the BBMVE monolayer with 25 μg/ml fluorescein isothiocyanate (FITC)-DutchAβ40 protein for 30 min. The FITC-DutchAβ40 was aspirated, 30 μg/ml Alexa Fluor 647 (AF647)-TNVs was added and incubated for 60 min at 5% CO$_2$ and 37° C. with minimal shaking. The TNVs were removed, the cells were washed with HBSS, harvested and fixed using 4% paraformaldehyde. The Transwells® were stained with DAPI, mounted, and imaged with an Axiovert 100 M microscope equipped with Zeiss LSM 510 laser confocal microscope (DAPI, Ex/Em: 350/470 nm and AF647, Ex/Em: 652/668). Both images were acquired using the settings. These results were confirmed using flow cytometry which determines the amount of intracellular AF647 signal.

In Vivo Studies

Plasma Pharmacokinetics and Tissue Distribution of $^{125}$I-TNVs

For the in vivo studies $^{125}$I-TNVs were prepared by radioiodinating the pIgG4.1 or pF(ab)$_2$4.1 using chloramine-T reaction. The femoral vein and artery of each mouse were catheterized under general anesthesia (isoflurane=1.5% and oxygen=4 l/min). A bolus IV dose of $^{125}$I-TNVs (100 μCi) were administered to a group of three mice previously injected with 150 μl saline. The treatment group of mice received a pre-injection of 150 μl (3.3 mg/ml) of DutchAβ40, followed by an IV bolus dose of $^{125}$I-TNVs (100 μCi) after 30 min. Blood was sampled (20 μl) from the femoral artery of each mouse at various time intervals (0.5, 1, 3, 5, 10, 15, 30, 45, 60 and 90 min). Each blood sample was diluted to a volume of 100 μl with normal saline, the plasma was separated by centrifugation and analyzed for $^{125}$I activity using a two-channel gamma counter (Cobra II; Amersham Biosciences Inc., Piscataway, N.J.). At the end of the experiment, the animals were transcardially perfused with excess saline. Various peripheral organs such as heart, liver, kidney, spleen as well as the brain of each animal were removed. The brain was then dissected into various anatomical regions (cortex, caudate putamen, hippocampus, thalamus, brain stem, and cerebellum) and were all analyzed for $^{125}$I radioactivity. Pharmacokinetic modeling was conducted using 1 compartmental analysis with uniform weighting (WinNonlin®, Version 5.2, Mountain View, Calif.) as defined by the equation:

$$Cp = Cp^0 \times e^{-Kel \times t} \quad (2)$$

Where Cp is the plasma concentration at the predetermined time point, $Cp^0$ is the plasma concentration at time=0, kel is the elimination rate constant and t is the predetermined time points. From this, the area under the curve (AUC), clearance (cl) and volume of steady state (Vss) were derived.

Brain Single Photon Emission Computerized Tomography (SPECT) Imaging

To evaluate the brain distribution of $^{125}$I-TNVs, a dose of 5 μCi/g of $^{125}$I-CCNs or $^{125}$I-TNVs was administered to mice intravenously under general anesthesia (isoflurane=1.5% and oxygen=4 l/min). Then the brain uptake of either $^{125}$I-CCNs or $^{125}$I-TNVs was monitored by dynamic SPECT imaging with continuous image acquisitions every minute for 10 min.

Magnetic Resonance Imaging

Preparation of TNV Phantoms

Phantoms were prepared according to the procedures described previously [19]. Briefly, 10 mg/ml of TNV stock suspension was prepared in distilled water, which was further diluted with distilled water to obtain ratios of 1:1, 1:5, 1:10, 1:30, 1:100, 1:300, 1:1000 and 1:3000. Each sample was then mixed with 1% agarose at a ratio of 1:1. The TNV-agarose mixtures containing gadolinium concentration of 2000, 200, 70, 20, 7, 2, 0.7 or 0.2 μM were carefully injected into microcapillary tubes (length=90 mm and diameter=5 mm) (Wilmad-Labglass Co, Vineland N.J.) without forming air bubbles. Each capillary tube containing 900 μl of TNV-agarose mixture was allowed to solidify on ice. The control phantoms were prepared by replacing TNVs with distilled water and were simultaneously imaged with the TNV phantoms.

MRI Relaxation of Phantoms

All MR images were acquired using a 21.1 T vertical magnet with a bore diameter of 105-mm [20]. The magnet was equipped with a Bruker Avance III spectrometer console and acquisition was performed with ParaVision 5.1 software (Biospin Corp., Billerica, Mass.) and a 64-mm inner diameter high performance gradient (Resonance Research Inc, MA). All samples were imaged in unison within a 10-mm nmr tube using a 10-mm birdcage coil tuned to 900 MHz and by maintaining the proton (1H) resonance frequency at 21.1 T. Measurements were performed to quantify 1/$T_1$ relaxation rate ($R_1$), 1/$T_2$ relaxation rate ($R_2$) and 1/$T_2^*$ relaxation rate ($R_2^*$) for each sample. Common acquisition parameters for all sequences included: Matrix=128×128, FOV=8.8×8.8 mm, slice thickness=1.0 mm and 2 averages. For $R_1$ and $R_2$ measurements, a single slice 2D spin-echo (SE) sequence was used with nine incrementing repetition times (TR=25-15000 ms) and 16 incrementing echo times (TE=8-124 ms) for each respective contrast weighting. For $R_2^*$ measurements, a 2D gradient recalled echo (GRE) sequence was used with TR=5000 ms, and 16 incremented TEs from 3.0-63 ms. Magnitude images were analyzed using regions of interest (ROIs) drawn to cover each individual microcapillary tube as well as a noise ROI for baseline corrections. The ROI signal intensities were fitted by non-linear regression using the Levenburg-Marquadt algorithm in SigmaPlot 7.101 (SPSS Inc, Chicago, Ill.). For $R_2$ and $R_2^*$ measurements, a single exponential decay function with baseline adjustment was employed while a single exponential growth with baseline adjustment was applied for $R_1$. All regressions were fitted with a noise baseline to account for the rectified noise of magnitude images.

MR Imaging of Ex-Vivo Mouse Brain

Mice were administered with an IV bolus dose of saline (150 μl) or 0.5 mg of DutchAβ40 in 150 μl under general anesthesia (isoflurane 1.5% and oxygen 4 l/min). After 30 min, 200 μl of TNV suspension containing 2 mM gadolinium was injected. The mice were deeply anesthetized during ensuing time period. At the end of each experiment, the animals were transcardially perfused with 20 ml of phosphate-buffered saline (PBS) followed by 10 ml of 4% paraformaldehyde (PFA). The mice brains were excised and stored in 4% paraformaldehyde prior to MRI. The brains were placed individually in 10-mm NMR tubes containing fluorinert (3M Center, St. Paul, Minn.), a perfluorinated liquid with no 1H MRI signal. The brains were imaged in unison with a 35-mm RF birdcage coil resonating at 900 MHz. A 3D GRE was used to generate high resolution $T_2^*$ weighted images. Echo (TE) and repetition (TR) times were set to 10 and 150 ms respectively with a spectral width of 12.5 kHz. Using a field of view of 2×2.5×1.8 cm to cover multiple brains and a matrix seize of 400×500×360, a 50-μm isotropic resolution was achieved. The data set was processed with AMIRA 5.3.3 (Visage imaging, CA) to visualize the brain structure of interest and compare each individual brain in an accurate manner.

Cytokines Inhibition Studies

Luminal or abluminal region of BBMVE cell monolayer was either challenged with DutchAβ40 alone, in the presence of TNVs, or with naked cyclophosphamide (TNV=1.74 mg/ml, Aβ40=25 μg/ml, cyclophosphamide=3.05 mg/ml) at 37° C. for 24 hr. At the end of 24 hour treatment, the luminal or abluminal solutions of the control and the treated Transwells® was assayed for IL-6, IL-1β and TNF-α using cytokine enzyme linked immunosorbent assay (ELISA) kit (Thermo Scientific, Rockford, Ill.). The cytokine levels secreted by the control BBMVE cell monolayer incubated with hanks balanced salt solution (HBSS) were used as the baseline values.

Results

TNV Characterization

Figure 2:
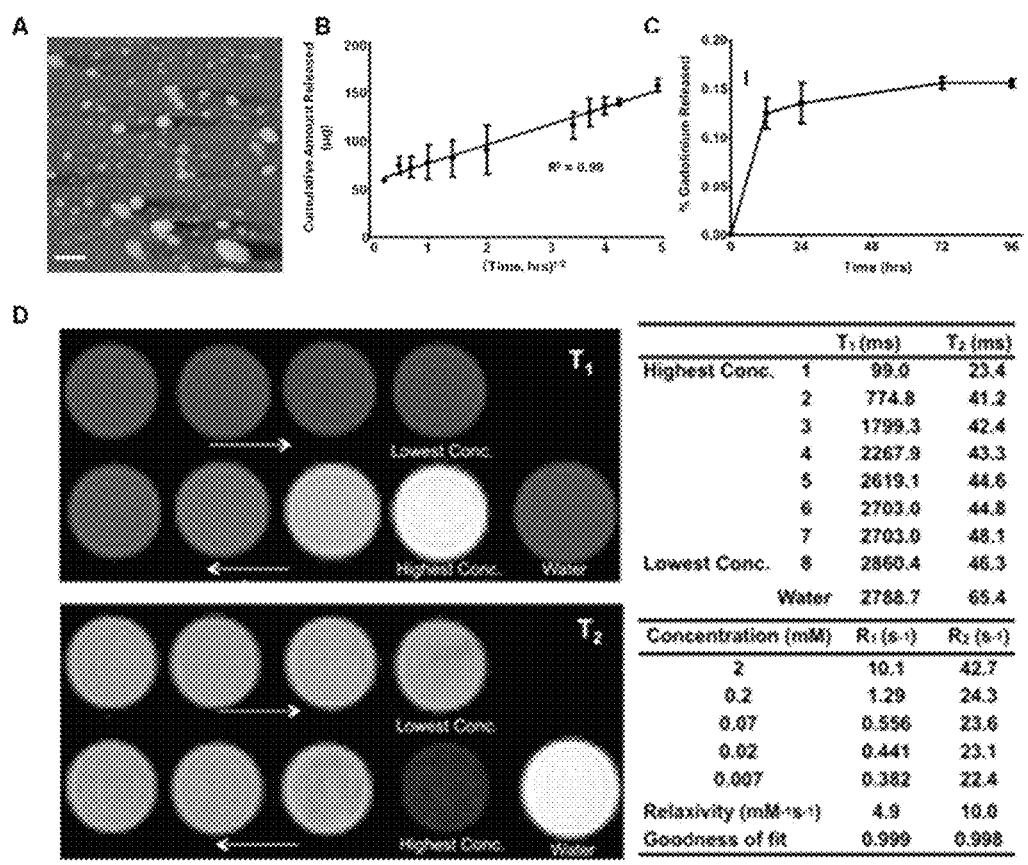
FIG. 2. (A) Atomic force micrograph of theranostic nanovehicles (TNV); scale bar represents 250 nm. Gadolinium and cyclophosphamide (CYC) interaction and release from chitosan nanocarrier: (B) Standard curve of absorption peak heights, measured at 1454.2 or 738.4 $cm^{-1}$, and cyclophosphamide content (%) in TNV and other physical mixtures of cyclophosphamide and Magnevist®-conjugated chitosan (MCC); (C) Cyclophosphamide release profile from TNVs in phosphate buffer solution (pH 7.4) at 37° C.; (D) Leakage of gadolinium from TNVs in four days. (E) Relationship between gadolinium concentration and $T_1$ or $T_2$ relaxation times at 21.1 Tesla. The $T_1$ or $T_2$ relaxation time decreases with increase in gadolinium concentration.

The FTIR spectrum of Magnevist®-conjugated chitosan (MCC) exhibited prominent absorbance band around 3260 cm$^{-1}$ (FIG. 1A), most likely from the free hydroxyl groups on chitosan, and an absorbance peak at 1599 cm-1 that may signify amide linkage between chitosan and Magnevist® (FIG. 1B). The AFM micrograph demonstrated that the TNVs made from the MCC are roughly spherical particles and a majority of them are smaller than 250 nm (FIG. 2A).

The mean hydrodynamic diameter of TNVs (239±4.08 nm) determined by photon correlation spectroscopy was 45% larger than that of CCNs (164±1.21 nm) made from chitosan. However, the CCNs showed mean zeta potential value almost twice as much as the TNVs (Table 1).

TABLE 1

Mean particle size, zeta potential, and loading efficiency of control chitosan nanoparticles (CCNs) and theranostic nanovehicles (TNVs).

| Formulation | Size (nm) | Zeta Potential (mV) | Cyclophosphamide (w/w, %) | Magnevist ® (w/w, %) |
|---|---|---|---|---|
| CCN | 164 ± 1.2 | 21.6 ± 1.7 | — | — |
| TNV | 239 ± 4.1 | 11.9 ± 0.5 | 21.7 ± 1.3 | 60.67 ± 9.2 |

— = contains no cyclophosphamide (CYC) or Magnevist ®.
Data shown are mean ± SEM (n = 3).

Gadolinium and Cyclophosphamide Content in TNVs

The loading efficiency of cyclophosphamide in TNVs was predicted using FTIR spectroscopy. The FTIR peak intensities at 1454 or 736 cm$^{-1}$, which are unique to cyclophosphamide, in the MCC and cyclophosphamide mixtures (FIG. 1B), were plotted against the known cyclophosphamide concentrations in MCC matrix (FIG. 2B). From this standard curve, the unknown cyclophosphamide concentration in the TNVs was predicted to be 21.7±1.31% w/w (Table 1), which coincided with that obtained from mass balance studies. The gadolinium content in the TNVs was determined as 60.67±9.2% by arsenazo III assay (Table 1).

In vitro release of cyclophosphamide and leakage of gadolinium from the TNVs Cyclophosphamide release from the TNVs was linear with $\sqrt{\text{time}}$ and exhibited adequate fit to Higuchi's model with $r^2$=0.997 (FIG. 2C). However, the leakage of gadolinium from the TNVs was as low as 0.1% in the first 12 hours and was insignificant (<0.02%) for the following four days (FIG. 2D).

MRI Relaxometry of TNVs

The TNVs were embedded in tissue mimicking agarose and the MRI contrast generated by these phantoms was evaluated as a function of gadolinium concentration (FIG. 2E). As the amount of gadolinium increased in the phantoms, greater $T_1$ contrast enhancement and the consequent shortening of T1 relaxation times were seen. In a similar manner, phantoms carrying higher gadolinium concentrations generated greater $T_2$ contrast under $T_2$ weighted imaging sequence. Utilizing the inverse relaxations times ($R_1$=1/$T_1$ and $R_2$=1/$T_2$) as a function of concentration, relaxivities $r_1$ and $r_2$ were calculated and estimated to be 4.9 and 10.0 mM$^{-1}$ s$^{-1}$, respectively under 21.1 T (900 MHz) field strength.

Ability of TNVs to Bind to Amyloid Deposits

Figure 3:
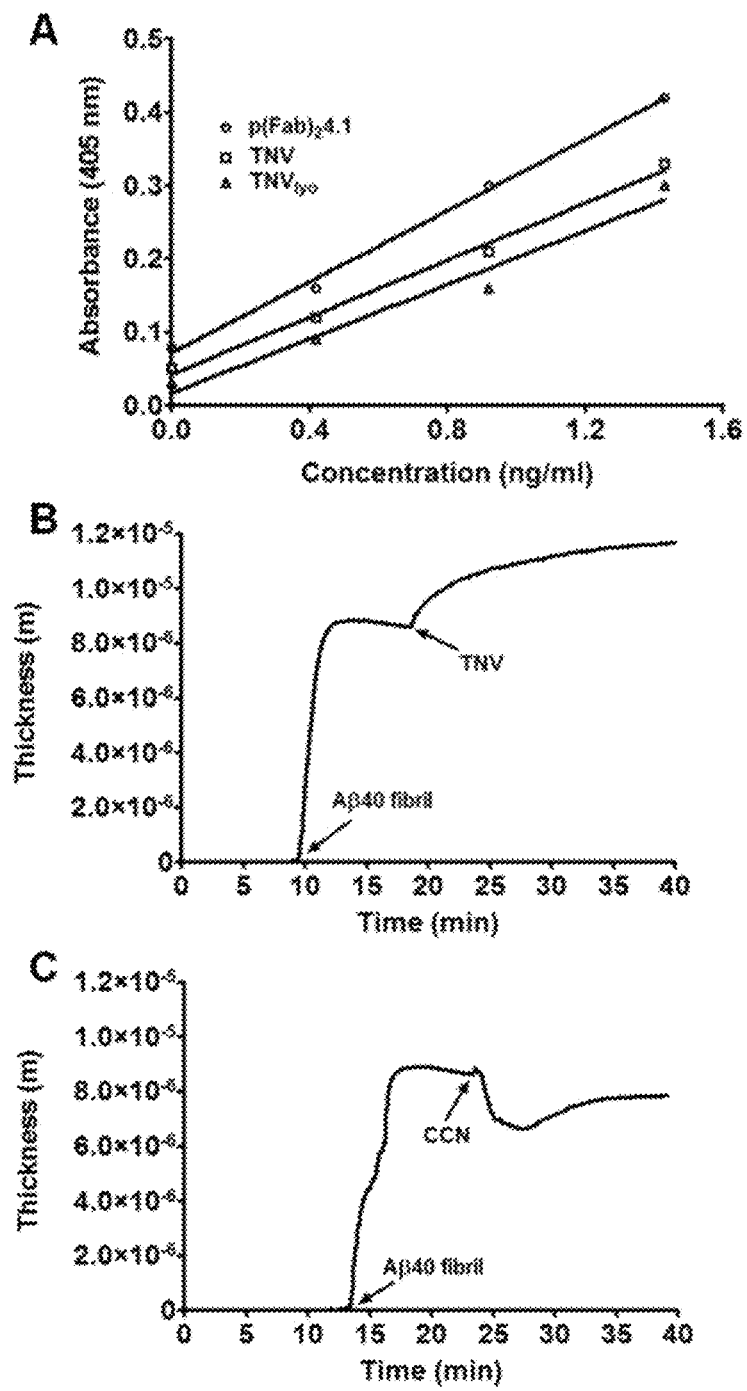
FIG. 3. Binding of various TNV formulations to soluble human Aβ40 or Aβ40 fibrils determined by ELISA and quartz crystal microbalance-dissipation methods. (A) Binding of p(Fab')$_2$4.1, freshly prepared TNVs, lyophilized TNVs (TNVlyo) to soluble human Aβ40 protein. (B) Binding of TNVs to Aβ40 fibrils adsorbed on the QCM-D crystal sensor and (C) Binding of control chitosan nanoparticles (CCNs) to Aβ40 fibrils adsorbed on QCM-D crystal sensor.

The ability of CCNs or TNVs to detect and bind to Aβ fibrils was determined by two approaches, ELISA and QCM-D methods. The ELISA data have shown stronger TNV binding to Aβ40 fibril coated-substrate than that of CCNs. However, p(Fab$_2$)4.1 showed slightly stronger binding to Aβ40 fibrils (FIG. 3A) than either TNV or CCN. There was no statistically significant difference between the binding of freshly prepared TNVs or lyophilized TNVs (TNV$_{lyo}$) to Aβ40 fibrils (FIG. 3A). According to the QCM-D method, the adsorption of TNVs to the Aβ40 fibril-bed deposited on the gold-coated quartz crystal (FIG. 3B) was estimated as 3.1±0.2 μg/cm$^{-2}$ (Table 2). Conversely, the mass of CCNs (FIG. 3C) adsorbed to the Aβ40 fibril-bed was 2.5±0.4 μg/cm$^{-2}$ (Table 2).

TABLE 2

Comparison of control chitosan nanoparticle (CCNs) and theranostic nanovehicle (TNVs) binding to immobilized Aβ40fibrils on quartz gold crystal.

| | Treatment | |
|---|---|---|
| Parameter | With Aβ40 fibril | Without Aβ40 fibril |
| HBSS (μg/cm$^2$) | 1.6 ± 0.2 | n/a |
| CCN (μg/cm$^2$) | 2.5 ± 0.4 | 0.8 ± 3.3 |
| TNV (μg/cm$^2$) | 3.1 ± 0.2 | 1.4 ± 0.5 |

Data are expressed as mean ± SEM (n = 3).

The Uptake of TNVs in the In Vitro BBB Model

Figure 4:
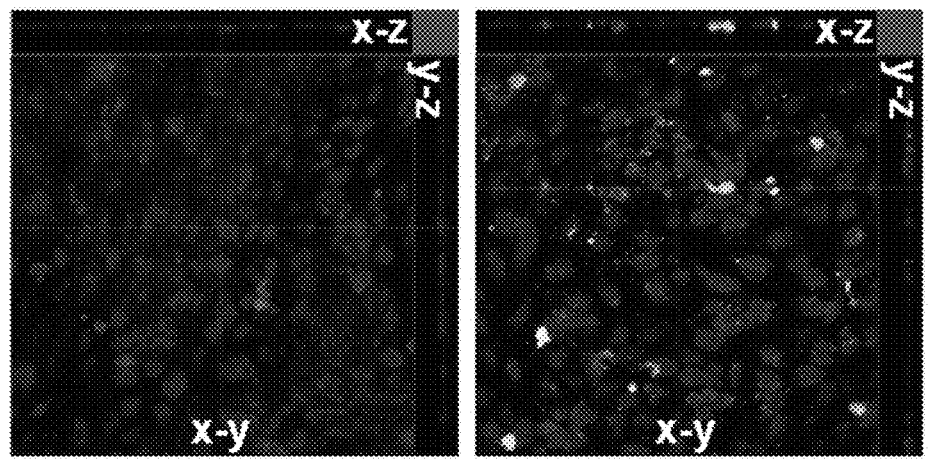
FIG. 4. (A) The uptake of a) alexa fluor 647 (AF647)-TNVs in saline- or b) AF647-TNVs in fluorescein isothiocyanate (FITC)-DutchAβ40-treated BBMVE monolayers, respectively, as seen using laser confocal microscopy. (B) The uptake of HBSS- (control), AF647-IgG4.1, AF647-control chitosan nanoparticles (CCNs) or AF647-TNVs in DutchAβ40-treated BBMVE monolayers as seen using flow cytometry. G.M. is geometric mean whereas C.V. is the coefficient of variance. ***$p<0.001$; AF647-TNVs and AF647-CCNs versus AF-647-IgG4.1 in DutchAβ40 treated BBMVE cells.
Figure 4:
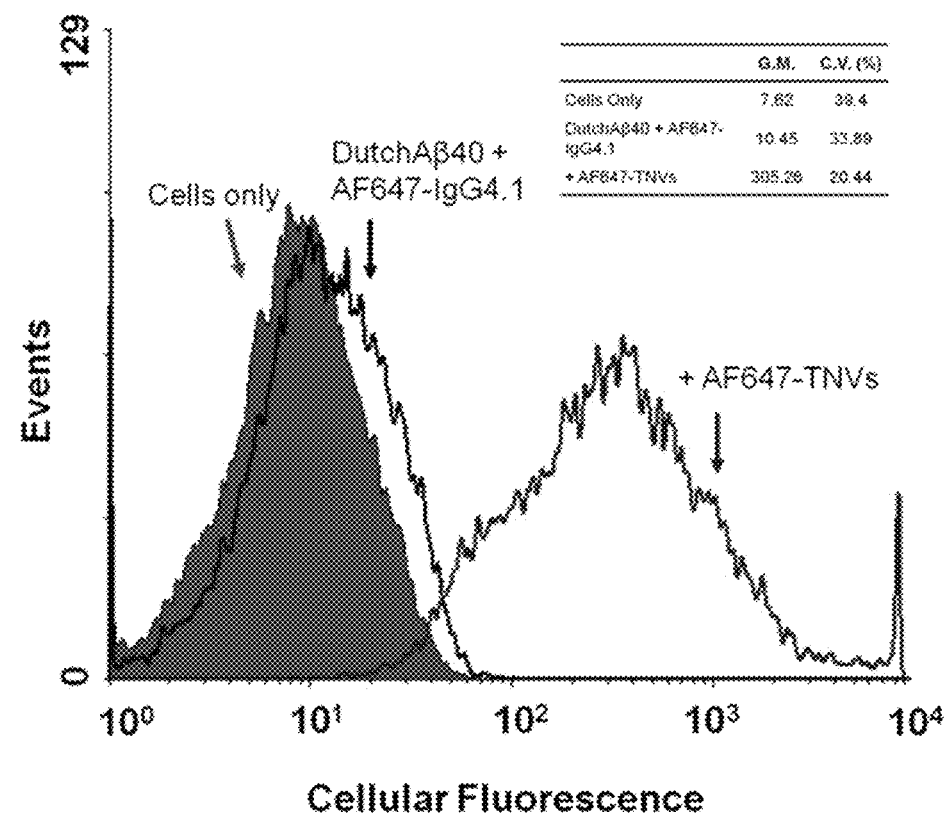

The uptake of AF647-TNVs by the BBMVE cell monolayers was evaluated first through laser confocal microscopy, which clearly showed greater uptake of AF647-TNVs in the BBMVE cell monolayer pre-treated with FITC-DutchAβ40 (FIG. 4A.i) than in those pre-treated with HBSS (FIG. 4A.ii). Next, the amount of intracellular AF647 fluorescence signal was quantified using flow cytometry as a measure of AF647-TNV uptake by the BBMVE cells. The accumulation of AF647-TNVs in DutchAβ40 pre-treated BBMVE cells showed a 30-fold increase than that of free AF647-IgG4.1 antibody (FIG. 4B).

Biodistribution of TNVs

Figure 5:
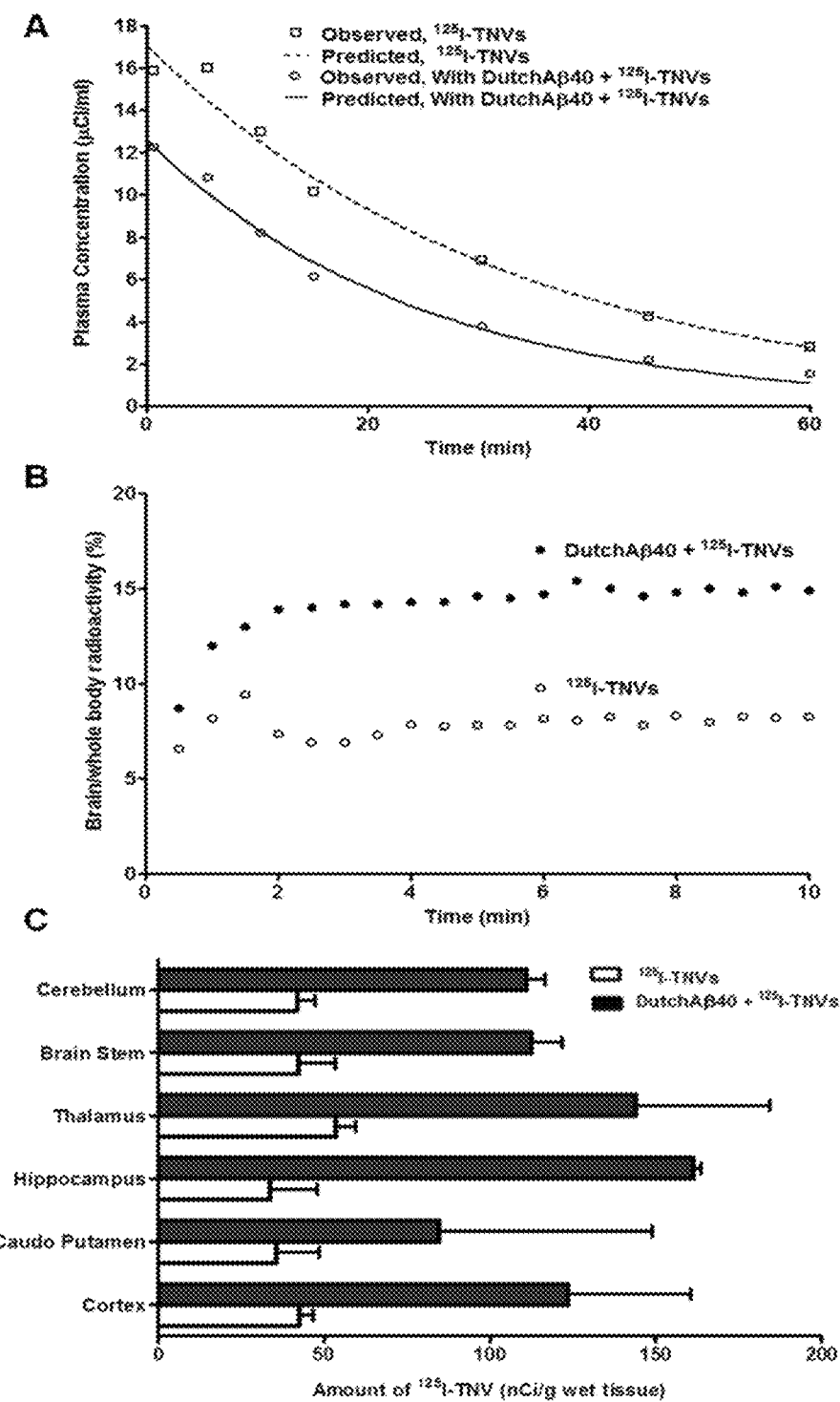
FIG. 5. (A) Plasma pharmacokinetics of $^{125}$I-TNV in control and DutchAβ40 pre-injected mice. (B) Uptake of radioiodinated theranostic nanovehicles (125I-TNV) or control chitosan nanoparticles ($^{125}$I-CCN) by cerebrovascular endothelium as determined by dynamic single photon emission computerized tomography (SPECT/CT). (C) Accumulation of $^{125}$I-theranostic nanovehicles (TNVs) in the various regions of the brain in control and DutchAβ40 pre-injected mice.

Following intravenous administration, the plasma pharmacokinetics of $^{125}$I-TNVs in control and DutchAβ40 pre-injected WT mice exhibited a monoexponential disposition (FIG. 5A). Initial plasma concentration (Cp$^0$) and AUC of $^{125}$I-TNVs in DutchAβ40 pre-injected mice were significantly (p<0.001) lower than that in the control mice injected with saline (Table 3). However, the volume of distribution (Vss) and elimination rate constant (kel) of $^{125}$I-TNVs in DutchAβ40 pre-injected mice were not significantly different from those seen in control mice. In addition, there was no significant difference in the $^{125}$I-TNVs accumulation was observed in the heart, liver, kidney and spleen of control versus DutchAβ40 pre-injected mice (Table 4).

TABLE 3

Pharmacokinetic parameters of $^{125}$I-theranostic nanovehicle ($^{125}$I-TNV) in control and DutchAβ40 pre-injected mice.

| | $^{125}$I-TNVs | | |
|---|---|---|---|
| Parameter | With DutchAβ40 | Without DutchAβ40 | p |
| AUC (min × μCi/ml) | 303.2 ± 29.91 | 567.8 ± 5.16 | *** |
| K10 (min$^{-1}$) | 0.045 ± 0.01 | 0.031 ± 0.002 | N.S. |
| Cl (ml/min/μCi) | 0.34 ± 0.036 | 0.18 ± 0.002 | * |
| Vss (ml/μCi) | 7.48 ± 0.30 | 5.90 ± 0.53 | N.S. |

Data presented as mean ± SEM,
* p < 0.05,
*** p < 0.001.
N.S., not significant

TABLE 4

Biodistribution of $^{125}$I-theranostic nanovehicle ($^{125}$I-TNV) in control and DutchAβ40 preinjected adult mice

| | $^{125}$I-TNVs | | |
|---|---|---|---|
| Organ | With DutchAβ40 (nCi/g wet tissue) | Without DutchAβ40 (nCi/g wet tissue) | p |
| Heart | 674.1 ± 498.5 | 1350 ± 202.5 | N.S. |
| Liver | 9696 ± 4869 | 12515 ± 4957 | N.S. |

TABLE 4-continued

Biodistribution of $^{125}$I-theranostic nanovehicle ($^{125}$I-TNV) in control and DutchAβ40 preinjected adult mice

| | $^{125}$I-TNVs | | |
|---|---|---|---|
| Organ | With DutchAβ40 (nCi/g wet tissue) | Without DutchAβ40 (nCi/g wet tissue) | p |
| Kidney | 10173 ± 6209 | 19685 ± 5316 | N.S. |
| Spleen | 7699 ± 4586 | 5285 ± 1986 | N.S. |

Data are mean ± standard error of the mean (n = 3);
ns: not significant

Dynamic SPECT imaging demonstrated differential targeting of $^{125}$I-TNV and $^{125}$I-CCN to the cerebral vasculature immediately following IV bolus administration (FIG. 5B). The results showed greater cerebrovascular accumulation of $^{125}$I-TNVs (19.3% of the total body counts) compared to that of $^{125}$I-CCNs (8.2% of the total body counts). To further investigate the ability of TNVs to target Aβ protein accumulated in the cerebral vasculature, the mice were pre-injected with vasculotropic DutchAβ40 prior to the $^{125}$I-TNVs administration. The $^{125}$I-TNVs accumulation in various brain regions of DutchAβ40 pre-injected mice was found to be 2- to 4-fold greater than that in the control mice pre-injected with saline (FIG. 5C).

Detection of Cerebral DutchAβ40 by MRI Using TNVs as Contrast Agents

Figure 6:
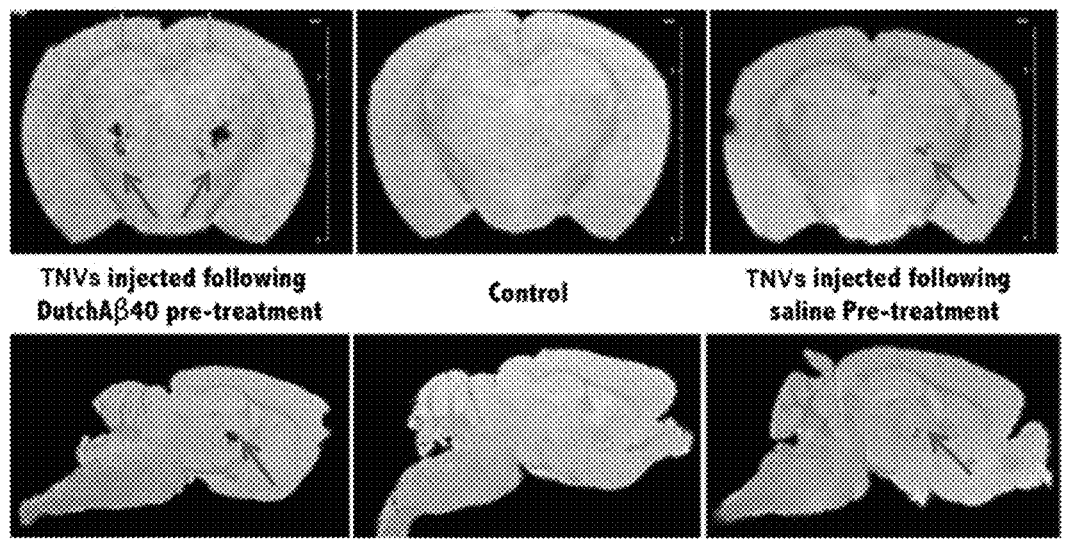
FIG. 6. Ex vivo magnetic resonance images of saline and DutchAβ40 pre-treated mice injected with theranostic nanovehicles (TNV). Control mouse received neither pre-treatment nor MNV injection. Red arrows indicated hypointense larger arteries in mice injected with MNVs; no evidence of specific contrast was found in the control specimen. Orange arrows indicate representative hyperintense regions found in the highly vascularized hippocampus and cortex.

High-resolution GRE images displayed in the coronal orientation clearly demonstrated the accumulation of TNVs in ex-vivo mouse brain (FIG. 6). Highest contrast enhancement manifested as signal voids appeared in the cortex as well as in the hippocampal regions. In addition, hypointensity in larger arteries indicated with red arrows was found in TNV injected brains but not in the control specimen. Orange arrows indicate the structural delineation of sub-regions within the highly vascularized hippocampus of DutchAβ40 treated brains.

TNVs Inhibit Pro-Inflammatory Cytokine Release Triggered by DutchAβ40 Exposure.

Figure 7:
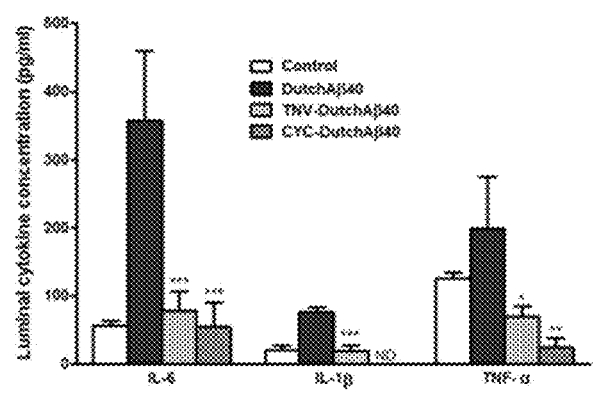
FIGS. 7. (A) Luminal and (B) abluminal secretions of interleukin-6 (IL-6), interleukin-1beta (IL-1β) and tumor necrosis factor-alpha (TNF-α) by BBMVE cell monolayers in control; challenged with DutchAβ40; theranostic nanovehicle (TNV)+DutchAβ40; and cyclophoshamide (CYC)+DutchAβ40 (TNV=1.74 mg/ml, DutchAβ40=25 μg/ml, cyclophosphamide=3.05 mg/ml) groups. Data expressed as mean±S.D (n=3) and analyzed using one-way ANOVA followed by Turkey's comparison test. *$p<0.001$, IL-6 secretion by DutchAβ40 challenged versus TNV+DutchAβ40 treated or CYC+DutchAβ40 treated; *$p<0.001$, IL-1β secretion by DutchAβ40 challenged versus TNV+DutchAβ40 treated; **$p<0.01$, TNF-α secretion between DutchAβ40 challenged versus CYC+DutchAβ40 treated.

The BBMVE cell monolayer treated with vasculotropic DutchAβ40 on the luminal side showed an enhanced release of pro-inflammatory cytokines such as interleukin-6 (IL-6), interleukin-1beta (IL-1β) and tumor necrosis factor-alpha (TNF-α). However, when the TNVs or naked cyclophosphamide (at a concentration 10-fold greater than that found in TNVs) were added to the luminal side along with DutchAβ40 protein, a significant decrease in the secretions of these cytokines was observed (FIG. 7).

Discussion

Currently there is no diagnosis or treatment for CAA [22]. The definitive CAA diagnosis is reached post mortem by histopathological examination of the patient's brain. On the other hand, the current CAA treatment with immunosuppressants such as cyclophosphamide and methylprednisolone is associated with extensive systemic toxicity. To address these limitations, we designed TNVs comprising of cyclophosphamide loaded nanocore made of Magnevist® conjugated chitosan. Novel anti-amyloid antibody 4.1 (IgG4.1) or its F(ab')$_2$ fragment (F(ab')$_2$4.1) is grafted on the polymeric core to aid the targeting of TNVs to cerebrovascular amyloid. The IgG4.1 or F(ab')$_2$4.1 are cationized with putrescein, which was shown to enhance the BBB permeability of the nanovehicle [12]. By providing MRI contrast and delivering therapeutic agents to the amyloid ridden cerebrovascular tissue, the TNVs aid in the early detection of CAA and allows for its pre-symptomatic treatment.

The mean hydrodynamic diameter of TNVs (239±4.1 nm) was greater than that of the blank nanoparticle (164±1.2 nm), most likely due to the incorporation of cyclophosphamide and Magnevist® (Table 1). However, the mean zeta potential value of the blank nanoparticles was almost 2-fold greater than that of the TNVs. Such reduction of TNV zeta potential value may be attributed to the participation of amine groups (—NH2) on chitosan polymer, which contributes to positive zeta potential value when protonated, in the amide bond formation with the carboxyl groups of the Magnevist® [13]. The amide bond formation was indicated by the increased FTIR absorption at 1599 cm$^{-1}$ (FIG. 1B). The FTIR spectroscopy was also employed to assay the cyclophosphamide entrapped in TNVs by quantifying the absorption peak at 736.2 cm$^{-1}$, which is unique to cyclophosphamide (FIG. 2B). When exposed to aqueous environment, the cyclophosphamide release from TNVs was linear with √time, which is typically seen with controlled drug release from polymeric matrices (FIG. 2C). The Magnevist® did not leak out appreciably when the TNVs were exposed to aqueous environment and the agarose TNV phantoms provided excellent contrast enhancement in high field strength (21.1 Tesla) MR environment (FIG. 2D-E).

The ability of TNVs to detect and bind to Aβ fibrils was determined using ELISA and QCM-D methods. The ELISA has shown that the extent of pF(ab')$_2$4.1 binding to Aβ40 fibrils was not significantly compromised after conjugation to the nanovehicle (FIG. 3A). Moreover, freshly prepared as well as lyophilized TNVs have comparable binding to Aβ fibrils, which suggested that the integrity of pF(ab')$_2$4.1 was not significantly altered during lyophilization. The ability of TNVs to bind to Aβ40 fibrils under the shear force exerted by the blood flow in the cerebral vasculature was determined by QCM-D, in which the TNV suspension was passed through a microfluidic channel over the Aβ40 fibril bed adsorbed to the gold-coated quartz crystal. The QCM-D data showed higher binding of TNVs than CCNs to the Aβ fibril bed adsorbed on the gold/quartz crystal (FIG. 3B-C). Although, the CCNs have comparable concentration and viscosity as TNVs, they created an initial trough in the mass adsorbed to the sensor (FIG. 3C). This could be attributed to the removal of trapped water by the CCNs as they exited from the microfluidic chamber. In case of TNVs, however, the loss of weight due to water removal is most likely compensated by the enhanced binding of the nanovehicles to the Aβ fibril bed on the crystal.

A substantial increase in uptake of AF647-TNVs was seen in the BBMVE cell monolayers pre-treated with FITC-DutchAβ40 as compared to those pre-treated with HBSS (FIG. 4Aa-b). This clearly demonstrates the ability of the IgG4.1 conjugated on the surface of TNVs to facilitate increased transcytosis of TNVs in response to the DutchAβ40 protein. Next, flow cytometry was used to determine the amount of intracellular accumulated AF647-IgG4.1 and AF-TNVs in DutchAβ40 treated cells. A 40-fold increase in internalization of AF647-TNVs in BBMVE cells pre-treated with DutchAβ40 as compared to those treated with only HBSS was seen (FIG. 4B). Alternatively, AF647-IgG4.1 exhibited a non-significant increase in the uptake by cells pre-treated with Dutchβ40 compared to HBSS treated cells (FIG. 3D), which shows significant uptake of AF647-TNVs compared to AF647IgG4.1. These results again clearly show that the IgG4.1, which is conjugated to the nanoparticle surface, plays a major role in facilitating the intracellular uptake of the TNVs in the DutchAβ40 treated monolayer (FIG. 4B).

Further studies were conducted to determine the biodistribution of TNVs and their ability to serve as MRI and SPECT contrast agents to detect cerebrovascular amyloid (FIG. 5A). The SPECT/CT imaging of the mice injected with $^{125}$I-TNVs or $^{125}$I-CCNs have demonstrated the greater ability of $^{125}$I-TNVs to target cerebrovascular endothelium than that of the $^{125}$I-CCNs (FIG. 5B). This is indicative of greater margination of TNV towards the BBB endothelium than the radiolabeled albumin grafted-control chitosan nanoparticles ($^{125}$I-CCNs). Based on these major findings, it is concluded that TNVs are capable of detecting amyloid accumulation in the cerebral vasculature (FIG. 5B-C).

Ex vivo MR images revealed greater contrast provided by TNVs in the brains pre-treated with DutchAβ40 than in the untreated mice brains or those treated with saline (FIG. 6). However, in contrast to TNV phantoms, the contrast enhancement in these images is represented by signal voids with no $T_1$ enhancement which indicates that the TNV is confined to cells or intracellular vesicles where the surface-to-volume ratio is low and consequently limits water access resulting in a so called $T_1$-quenching [21, 22].

Enhanced expression of pro-inflammatory cytokines, such as IL-6, IL-1β and TNF-α, has been observed in the brains of CAA and/or AD patients [23]. The cytokine upregulation was shown to trigger the overexpression of amyloid precursor protein [24], microglial activation, and the release of free radicals. On the other hand, amyloid accumulation in the cerebral vasculature has been shown to enhance cytokine secretion, stimulate immune response mediated by monocyte invasion into the brain tissue, and leads to the hemorrhages seen in CAA patients [25, 26]. Hence, the ability of TNVs to reduce the cytokine secretion provoked by the exposure of vasculotropic DutchAβ40 was tested. The data showed that TNVs significantly inhibited IL-6, IL-1β and TNF secretion triggered by DutchAβ40 on the luminal side (FIG. 7A).

Based on these findings, it is could concluded that TNVs are capable of detecting amyloid accumulation in the cerebral vasculature and also inhibit cytokines secreted by the BBMVE cell monolayer triggered by the Aβ40 exposure, and thereby treat cerebral inflammation in CAA.

BIBLIOGRAPHY

[1] Vinters H V, Gilbert J J. Cerebral amyloid angiopathy: incidence and complications in the aging brain. II. The distribution of amyloid vascular changes. Stroke; a journal of cerebral circulation. 1983; 14:924-8.
[2] Arvanitakis Z, Leurgans S E, Wang Z, Wilson R S, Bennett D A, Schneider J A. Cerebral amyloid angiopathy pathology and cognitive domains in older persons. Ann Neurol. 2010.
[3] Cordonnier C, van der Flier W M. Brain microbleeds and Alzheimer's disease: innocent observation or key player? Brain. 2011; 134:335-44.
[4] Viswanathan A, Patel P, Rahman R, Nandigam R N, Kinnecom C, Bracoud L, et al. Tissue microstructural changes are independently associated with cognitive impairment in cerebral amyloid angiopathy. Stroke; a journal of cerebral circulation. 2008; 39:1988-92.
[5] Kloppenborg R P, Richard E, Sprengers M E, Troost D, Eikelenboom P, Nederkoorn P J. Steroid responsive encephalopathy in cerebral amyloid angiopathy: a case report and review of evidence for immunosuppressive treatment. J Neuroinflammation. 2010; 7:18.
[6] Fountain N B, Lopes M B. Control of primary angiitis of the CNS associated with cerebral amyloid angiopathy by cyclophosphamide alone. Neurology. 1999; 52:660-2.
[7] Greenberg S M. Cerebral amyloid angiopathy and vessel dysfunction. Cerebrovasc Dis. 2002; 13 Suppl 2:42-7.
[8] Oh U, Gupta R, Krakauer J W, Khandji A G, Chin S S, Elkind M S. Reversible leukoencephalopathy associated with cerebral amyloid angiopathy. Neurology. 2004; 62:494-7.
[9] Thanvi B, Robinson T. Sporadic cerebral amyloid angiopathy—an important cause of cerebral haemorrhage in older people. Age Ageing. 2006; 35:565-71.
[10] Gonzalez-Duarte A, Cantu C, Ruiz-Sandoval J L, Barinagarrementeria F. Recurrent Primary Cerebral Hemorrhage: Frequency, Mechanisms, and Prognosis. Stroke; a journal of cerebral circulation. 1998; 29:1802-5.
[11] Ellis R J, Olichney J M, Thal L J, Mirra S S, Morris J C, Beekly D, et al. Cerebral amyloid angiopathy in the brains of patients with Alzheimer's disease: the CERAD experience, Part XV. Neurology. 1996; 46:1592-6.
[12] Agyare E K, Curran G L, Ramakrishnan M, Yu C C, Poduslo J F, Kandimalla K K. Development of a smart nano-vehicle to target cerebrovascular amyloid deposits and brain parenchymal plaques observed in Alzheimer's disease and cerebral amyloid angiopathy. Pharm Res. 2008; 25:2674-84.
[13] Saha T K, Ichikawa H, Fukumori Y. Gadolinium diethylenetriaminopentaacetic acid-loaded chitosan microspheres for gadolinium neutron-capture therapy. Carbohydr Res. 2006; 341:2835-41.
[14] Shikata F, Tokumitsu H, Ichikawa H, Fukumori Y. In vitro cellular accumulation of gadolinium incorporated into chitosan nanoparticles designed for neutron-capture therapy of cancer. Eur J Pharm Biopharm. 2002; 53:57-63.
[15] Poduslo J F, Curran G L, Wengenack T M, Malester B, Duff K. Permeability of proteins at the blood-brain barrier in the normal adult mouse and double transgenic mouse model of Alzheimer's disease. Neurobiol Dis. 2001; 8:555-67.
[16] Larson R R, Khazaeli M B, Dillon H K. Development of an HPLC method for simultaneous analysis of five antineoplastic agents. Appl Occup Environ Hyg. 2003; 18:109-19.
[17] Darras V, Nelea M, Winnik F M, Buschmann M D. Chitosan modified with gadolinium diethylenetriaminepentaacetic acid for magnetic resonance imaging of DNA/chitosan nanoparticles. Carbohydrate Polymers. 80:1137-46.
[18] Rowatt E, Williams R J. The interaction of cations with the dye arsenazo III. Biochem J. 1989; 259:295-8.
[19] Cheng F Y, Su C H, Yang Y S, Yeh C S, Tsai C Y, Wu C L, et al. Characterization of aqueous dispersions of Fe(3)O(4) nanoparticles and their biomedical applications. Biomaterials. 2005; 26:729-38.
[20] Fu R, Brey W W, Shetty K, Gor'kov P, Saha S, Long J R, et al. Ultra-wide bore 900 MHz high-resolution NMR at the National High Magnetic Field Laboratory. J Magn Reson. 2005; 177:1-8.
[21] Kok M B, Hak S, Mulder W J, van der Schaft D W, Strijkers G J, Nicolay K. Cellular compartmentalization of internalized paramagnetic liposomes strongly influences both T1 and T2 relaxivity. Magn Reson Med. 2009; 61:1022-32.

[22] Rosenberg J T, Kogot J M, Lovingood D D, Strouse G F, Grant S C. Intracellular bimodal nanoparticles based on quantum dots for high-field MRI at 21.1 T. Magn Reson Med. 2010; 64:871-82.

[23] Mrak R E, Griffin W S. Interleukin-1, neuroinflammation, and Alzheimer's disease. Neurobiol Aging. 2001; 22:903-8.

[24] Lannfelt L, Bogdanovic N, Appelgren H, Axelman K, Lilius L, Hansson G, et al. Amyloid precursor protein mutation causes Alzheimer's disease in a Swedish family. Neurosci Lett. 1994; 168:254-6.

[25] Maat-Schieman M L, van Duinen S G, Rozemuller A J, Haan J, Roos R A. Association of vascular amyloid beta and cells of the mononuclear phagocyte system in hereditary cerebral hemorrhage with amyloidosis (Dutch) and Alzheimer disease. Journal of neuropathology and experimental neurology. 1997; 56:273-84.

[26] Miao J, Xu F, Davis J, Otte-Holler I, Verbeek M M, Van Nostrand W E. Cerebral microvascular amyloid beta protein deposition induces vascular degeneration and neuroinflammation in transgenic mice expressing human vasculotropic mutant amyloid beta precursor protein. The American journal of pathology. 2005; 167:505-15.

Example 2

Multimodal Nanoprobes to Target Cerebrovascular Amyloid in Alzheimer's Disease Brain Introduction Cerebral amyloid angiopathy (CAA) currently affects a majority of Alzheimer's disease (AD) patients and one third of the aging population over 60 years old. The AD patients with CAA display more pronounced build-up of amyloid beta (Aβ) 40 and 42 proteins within the cerebral arteries and arterioles than those without CAA. The accumulation of these toxic Aβ proteins leads to cerebrovascular inflammation, vascular dysfunction, microhemorrhages in the early stages, but in advanced stages lobar hemorrhages and massive strokes are predominant [1].

Currently, there is neither a treatment nor a definitive pre-mortem diagnosis available for CAA. Theoretically, magnetic resonance imaging (MRI) has sufficient spatial and contrast resolution to visualize cerebrovascular amyloid and aid in CAA diagnosis. However, the detection of deposits less than 35 μm, which is critical for the early diagnosis of CAA, will require contrast enhancement [2]. Development of monocrystalline iron oxide nanoparticles (MIONs) as MRI contrast agents to detect cerebrovascular amyloid has been previously attempted [3]. However, this approach addresses CAA diagnosis, but not the treatment. In addition, MIONs cannot be tuned for detection via other modalities such as PET and SPECT imaging. Described herein is the development a nanovehicle capable of: a) specifically targeting cerebrovascular amyloid; b) serve as PET or MRI contrast agent for the early detection of CAA; and c) function as a drug delivery vehicle carrying effective doses of antioxidants such as curcumin or immunosuppressants like dexamethasone to the cerebral vasculature ridden with amyloid deposits.

Materials and Methods

Monoclonal antibody raised against human fibrillar Aβ42, IgG4.1, was developed at the Mayo Clinic [4], whereas DutchAβ40 was synthesized by the Mayo Clinic Proteomics Core Facility (Rochester, Minn.). SuperSignal West Dura extended duration chemiluminescent substrate and Bicinchoninic acid (BCA) protein assay kit were acquired from Thermo Scientific (Rockford, Ill.). The Mini-Protean® TGXTM 4-15% gel was obtained from Bio-Rad (Hercules, Calif.). Alexa Fluor 647 (AF647) labeling kit was attained from Invitrogen (Carlsbad, Calif.). Fetal bovine serum, donor horse serum, Dulbecco's modified Eagle's medium-Ham's F12 nutrient mixture (DMEM-F12), DMEM, and gentamycin, were acquired from Mediatech Inc. (Manassas, Va.). Quartz crystals (100 nm) with gold electrodes were purchased from Biolin Scientific® (Sweden). All other chemicals were purchased from Sigma Chemical Co (St. Louis, Mo.).

Animals

The B6/SJL mice were obtained from Jackson Laboratory (Bar Harbour, Me.). Swedish Tg2576 transgenic mice were purchased from Taconic (Germantown, N.Y.). All procedures were approved by the Mayo Clinic Institutional Animal Care and Use Committee and were performed in strict accordance with National Institutes of Health Guide for the Care and Use of Laboratory animals. Animals were housed in a non-barrier facility under controlled light and temperature.

Cell Culture

Human brain microvascular endothelial cells (hCMEC/D3) were cultured as described previously [6]. The hCMEC/D3 cells were seeded on the Transwells® (12 mm, Costar, Cambridge, Mass.) pre-coated with 0.1% type 1 rat-tail collagen. The Transwells® were maintained for 7 days at 5% $CO_2$ and 37° C. until the monolayer displayed transendothelial electrical resistance (TEER) values >175 ohms.

Nanoparticle Preparation

The polymeric nanocore without any surface modification is referred to as nanoparticle in this example.

Hydroxypropyl-Beta-Cyclodextran and Drug (HPβCD [Drug]) Complexation.

An aliquot of 50 mg HPβCD was added to 10 ml distilled water and continuously stirred overnight at room temperature. The next day, either 1.25 mg/ml of curcumin in acetone or 6.25 mg/ml dexamethasone in ethanol was added, allowed to equilibrate overnight, and the ethanol or acetone was allowed to evaporate for an additional 4 hours [7].

Conjugation of Magnevist® to Chitosan.

An aliquot of 95 mg/ml Magnevist®, a gadolinium based MRI contrast agent, was conjugated to 0.5% medium MW chitosan (MW=190,000-300,000 Da) using the carbodiimide reaction at pH 4.5 for 6 hrs [6, 8, 9]. Free Magnevist® was removed by dialyzing the conjugated preparation against distilled water using a Spectrapor 7 dialysis membrane with a MW cut-off (MWCO) of 50 kd.

Formation of Nanoparticles.

Curcumin or dexamethasone loaded nanoparticles were prepared using the ionic gelation technique at pH 5.0. The HPβCD complex was slowly added to Magnevist®-chitosan dispersion in a 2:9 ratio. The chitosan was then cross linked with 0.05% tripolyphosphate (TPP) to form the nanoparticles.

Preparation of Nanovehicles (Nanoparticles-IgG4.1).

The IgG4.1 nanoparticle is referred to as nanovehicle in this manuscript. The IgG4.1 (600, 1200 or 2400 μg) was covalently conjugated to 75 mg freshly prepared nanoparticles using the carbodiimide conjugation previously developed [3]. Nanovehicles were subjected to ultracentrifugation (171,000×g; 10 min) which served as a 1-step procedure to remove free IgG4.1 and therapeutic agent. The amount of IgG4.1 retained on the nanovehicle surface was characterized using BCA protein assay.

Substantiation of IgG4.1 Conjugation to Nanovehicles.

Western blot analysis was used to confirm successful conjugation of IgG4.1 to nanovehicles. Equivalent concentrations of pure IgG4.1 antibody and nanovehicles were separated using a 4-15% mini-PROTEAN® TGX™ precast gel and blotted onto 0.2 µm nitrocellulose membranes. The blots were blocked with 5% non-fat milk in phosphate buffered saline containing 0.05% Tween-20 (PBST), incubated with anti-mouse IgG-horseradish peroxidase antibody for 1 hr, washed with PBST and developed using SuperSignal West Dura chemiluminescent detection reagent.

Radioiodination.

The chloramine-T reaction was used to radiolabel nanovehicles with $^{125}$I [PerkinElmer Life and Analytical Sciences, Boston, Mass.] [10]. Unbound $^{125}$I was removed through overnight dialysis of the $^{125}$I-nanovehicle against PBS (pH 7.4). The purity of the radiolabeled nanovehicle was determined using the trichloroacetic acid (TCA) precipitation method and confirmed using paper chromatography as outlined previously [11].

Nanovehicle Characterization

The nanovehicle morphology was characterized using atomic force microscope (AFM) equipped with MultiMode Scanning Probe microscope (Veeco Metrology Inc., Plainview, N.Y.). Nanoparticles and nanovehicles were also characterized in terms of particle size (hydrodynamic diameter) and zeta potential using a BI-200SM dynamic laser light scattering system (Brookhaven Instruments, Holtsville, N.Y.) and a Zeta Plus machine (Brookhaven Instruments, Holtsville, N.Y.), respectively.

The amount of Magnevist® retained on the nanovehicle surface was quantified by measuring the differences in absorbance of nanovehicles with and without Magnevist® at 660 nm with 0.2 M Arsenazo III [12]. The amount of encapsulated curcumin in the nanovehicle formulation was quantified by measuring the fluorescence intensity after ultracentrifugation. To evaluate the curcumin released from the nanovehicles, 625 µg/ml of freshly prepared nanovehicles were placed in a dialysis bag (MWCO 50,000) and immersed in a PBS trough at 25° C. The trough contents were stirred continuously at 200 rpm, sampled at predetermined time points (1, 2, 4, 8, 16, 21, 25, 36, 48, 62, 72 and 90 hours) and the corresponding fluorescent signals were evaluated (Ex/Em: 488/535 nm).

The ability of nanovehicle formulations to recognize and bind to DutchAβ40 was evaluated using an enzyme linked immunosorbent assay (ELISA) method previously developed. A high protein binding 96-well plate was coated overnight with DutchAβ40, blocked using bovine serum albumin (BSA), and incubated with 7.5 mg nanovehicles at 37° C. for 3 hrs. The secondary anti-mouse IgG-alkaline phosphatase was used to estimate the amount of IgG4.1 bound to DutchAβ40 [4].

Nanovehicle Characterization Using In Vitro Techniques

Quartz crystal microbalance-dissipation (QCM-D) was used to evaluate the impact of systemic dilution on the propensity of various nanovehicles to marginate towards the BBB endothelium. In addition, the ability of nanovehicles to target cerebrovascular amyloid was tested by determining the extent of nanovehicle accumulation with the DutchAβ40 treated Madin Darby canine kidney (MDCK) cell monolayer grown on the quartz crystal sensor. The polarized MDCK cell monolayers are widely used as in vitro BBB models and were chosen for this experiment owing to their durability and compatibility with quartz sensors. The sensors, which are outfitted with gold electrodes were cleaned according to the manufacturers recommended protocol (QSense®, Västra Frölunda, Sweden). The MDCK cells were seeded on the sensor surface at a density of 5,000 cells/sensor and were incubated under 5% $CO_2$ and 37° C. for five days. The culture medium, which consisted of 90% DMEM, 10% FBS and 1× penicillin-streptomycin, was changed every 12 hrs. Before the experiment, the monolayer was incubated with 0.1% BSA in Hank's Buffered Salt Solution (HBSS) and 15 mM HEPES to block non-specific binding. The cell-sensors were placed in the QCM-D chamber maintained at 37° C. and HBSS-HEPES was passed through the chamber at a flow rate of 0.1 ml/min. Once the equilibration was established and the baseline stabilized, either HBSS (control) or 12.5 µg DutchAβ40 (treatment) was introduced over the course of 5 min, followed by 400 µl HBSS-HEPES to remove unbound DutchAβ40 at 100 µl/min. A 10.6 mg/ml aliquot of nanovehicle suspension was introduced at 100 µl/min for 5 min and changes in the sensor frequency were monitored. To evaluate the effect of systemic dilution of the nanoparticles as well as nanovehicles, various concentrations of nanoparticles or nanovehicle were floated across the naked sensor surface at the same flow rate and temperature settings. The changes in frequency were monitored and the mass absorbed to the crystal was calculated as follows:

$$\Delta m = -\frac{\Delta F \times C}{n} \quad (1)$$

where $\Delta m$ is the change in mass, $\Delta F$ is the change in frequency, C (mass sensitivity constant) is equal to 17.7 ng·cm$^{-2}$·Hz$^{-1}$ and n (overtone number) is equal to 5.

The Uptake of Nanovehicles by Human BBB In Vitro Model.

An amyloid treated brain endothelial model was prepared by pre-incubating the hCMEC/D3 monolayer (see section 2.2) with 12.5 µg DutchAβ40 protein for 20 min [13]. The protein was removed and an aliquot of 30 µg/ml Alexa Fluor 647 (AF647)-nanovehicles, in which AF647 was conjugated to IgG4.1 on the nanovehicle, was added and incubated for 1 hr at 5% $CO_2$ and 37° C. with minimal shaking. The nanovehicles were removed, the cells were harvested, washed with PBS and fixed using 4% paraformaldehyde. The amount of intracellular fluorescent signal was quantified using flow cytometry.

Elucidating the Mechanism of Nanovehicle Uptake by Human BBB Model In Vitro.

The human brain endothelial cell model was pre-treated with HBSS (control), 10 µg/ml nystatin (caveolae mediated endocytosis inhibitor) or 5 µg/ml chlorpromazine (clathrin mediated endocytosis inhibitor) for 30 min and then incubated with a 30 µg/ml aliquot of AF647-nanovehicles for 1 hour at 5% $CO_2$ and 37° C. with minimal shaking. The treatment was removed, the monolayers were washed, and fixed using 4% paraformaldehyde. The Transwells® were stained with DAPI, mounted, and imaged with an Axiovert 100 M microscope equipped with Zeiss LSM 510 laser confocal microscope (DAPI, Ex/Em: 350/470 nm and AF647, Ex/Em: 652/668). To maintain consistency, all images were acquired using the instrument settings.

In Vivo Characterization

To evaluate the brain distribution of nanovehicles, WT mice (20-25 g) were anesthetized (1.5% isoflurane, 4 l/min $O_2$) and their femoral arteries and veins were catheterized. The mice were pre-injected with DutchAβ40 protein (500 µg; treatment) or normal saline (100 µl; control) via the femoral vein and after 15 minutes 100 µCi of $^{125}$I-nanovehicles were administered to each mouse in control and treatment groups. At pre-determined time points (0.25, 1, 5, 15 and 30 min), 20 µl blood was collected from the femoral artery, the plasma was recovered from the sample, and immediately assayed for radioactivity using a two-channel gamma counter (Cobra II; Amersham Biosciences Inc., Piscataway, N.J.). Then the $^{125}$I-nanovehicles were removed from the cerebral blood flow using transcardial perfusion with PBS. The brains were removed from the skull, sectioned into six different brain regions, weighed, and assayed for radioactivity.

The plasma kinetic data thus obtained was analyzed using non-compartmental pharmacokinetic analysis (linear trapezoidal method) with uniform weighting (WinNonlin® Professional, version 5.2, Mountain view, Calif.). The area under the plasma kinetic curve was determined using logtrapezoidal rule:

$$AUC\int_{t_2}^{t_1} = \frac{C_1 + C_2}{(t_2 - t_1)} \quad (2)$$

where AUC is the area under the curve, $t_1$ and $t_2$ are the selected time points and $C_1$ and $C_2$ are the corresponding plasma concentrations. The plasma clearance (CL), volume at steady state (Vss) and other pharmacokinetic parameters were derived from the plasma data using WinNonlin®.

Ability of Nanovehicles to Target Cerebrovascular Amyloid

Nanovehicle targeting to cerebrovascular vessels was determined by administering 45 mg AF647-nanovehicles via external carotid to 2 year old APP transgenic or agedmatched WT mice. After 25 min, transcardial perfusion with 2 ml/kg Evan's Blue (shown by the blue fluorescence) in PBS followed by 4% paraformaldhyde was performed. Arterioles were isolated using (1.25, 1.5 and 1.75 M) sucrose gradient centrifugation [3]. The 1.5 M isolated fraction was mounted using cytospin, stained with Thioflavin S (marker for CVA deposits) and subsequently imaged using an Axiovert 100 M microscope with settings for fluorescein isothiocyanante (Ex/Em: 488/535 nm), Evan's Blue (Ex/Em: 550/610 nm) and AF647 [Ex/Em: 652/668 nm] [3].

Magnetic Resonance Imaging (MRI)

All MR images were acquired using a 21.1 T vertical magnet with a bore diameter of 105-mm, built entirely at the National High Magnetic Field Laboratory (NHMFL). The magnet was equipped with a Bruker Avance III spectrometer and acquisition was performed with ParaVision 5.1 (Bruker, Billerca Mass.) and a 64-mm inner diameter high performance gradient (Resonance Research Inc, MA).

MRI relaxometry measurements were carried with phantoms containing the Magnevist® conjugated nanovehicles. Phantoms were prepared by diluting the nanovehicles in distilled water to obtain a concentration range of 0.72-23 mM gadolinium. The solutions were injected into microcapillary tubes and sealed with silicone gel (Dow Corning, Midland, Mich.). The tubes were imaged in sets of 7 arranged using a 10-mm birdcage coil, tuned to a proton ($^1$H) resonance frequency of 900 MHz. Measurements were performed to quantify $R_1$ and $R_2$ relaxation for each dilution. For relaxation measurements, a single slice 2D spin-echo (SE) sequence was used with nine incrementing repetition times (TR=25-15000 ms) and 16 incrementing echo times (TE=8-124 ms) for each respective contrast weighting. Sequences were acquired with a matrix of 128×128, 1.0 mm slice thickness, and 2 averages. The images were analyzed using Regions of Interest (ROIs) drawn to cover each individual micro-capillary as well as a noise ROI to perform baseline corrections. The ROI signal intensities were fitted by non-linear regression using the Levenburg-Marquadt algorithm in SigmaPlot 7.101 (SPSS Inc, Chicago, Ill.); for $R_2$ measurements, a single exponential decay function with baseline adjustment was employed while a single exponential growth was applied for $R_1$.

For ex vivo MR imaging, 200 µl aliquot containing 17 mg of nanovehicles was injected, via the femoral vein, to 2-year-old APP transgenic (Tg2576) or aged-matched WT mice (25-30 g). Three hours following the injection, transcardial perfusion was performed with PBS followed by 4% paraformaldehyde. The brains were removed and stored in 4% paraformaldehyde at 4° C. until imaged. A day before MR imaging, the excised brains were washed in PBS then placed individually in conical tubes containing fluorinert (3M, St. Paul Minn.), a perfluorinated liquid with no $^1$H MRI signal. The brains were imaged in unison using a 35-mm RF birdcage coil resonating at 900 MHz. A 3D gradient recalled echo sequence (GRE) was used to generate high resolution $T_2^*$ weighted images. The matrix was set to achieve a 50-µm isotropic resolution. The echo (TE) and repetition (TR) times were set at 10 and 150 ms, respectively over a 15 hr scan time. The data set was processed with AMIRA 5.3.3 (Visage imaging, CA) to visualize the brain structure of interest and to compare each brain in an accurate manner.

SPECT Imaging

A 500 µCi dose of $^{125}$I-nanovehicles was administered to 2-year-old Tg2576 or aged-matched WT mice. The cerebral and peripheral organs were monitored for $^{125}$I-nanovehicle uptake by dynamic single photon emission computerized tomography/computerized tomography (SPECT/CT) imaging (Gamma Medica, Northridge, Calif.). Corresponding images were processed using Biomedical Image Quantification and Kinetic Modeling Software (PMOD Technologies, Switzerland). The brain uptake of nanovehicles at various time points was calculated using the following equation:

Brain uptake=$^{125}$I-NVs conc. in the brain−($^{125}$I-NVs conc. in the plasma×residual plasma volume)  (3)

Statistical Analyses

Statistical analyses were conducted using one-way analysis of variance (ANOVA) followed by Tukey post-test using GraphPad Prism 5.0 software (Graph Pad Software Inc., San Diego, Calif.). Statistical comparisons of the pharmacokinetic parameters were performed using Student's t-test. Biodistribution studies in WT mice, with and without DutchAβ40 treatment, were compared using two-way ANOVA with a Tukey post-test. All experiments were conducted in triplicate.

Results

In the following section, the formulation and characterization of nanovehicles; plasma pharmacokinetics and brain uptake; their ability to target cerebrovascular amyloid; and their potential as MRI and SPECT contrast agents to detect amyloid deposits in the cerebral vasculature are described.

Formulation of Curcumin- and Dexamethasone-Nanovehicles

Figure 8:
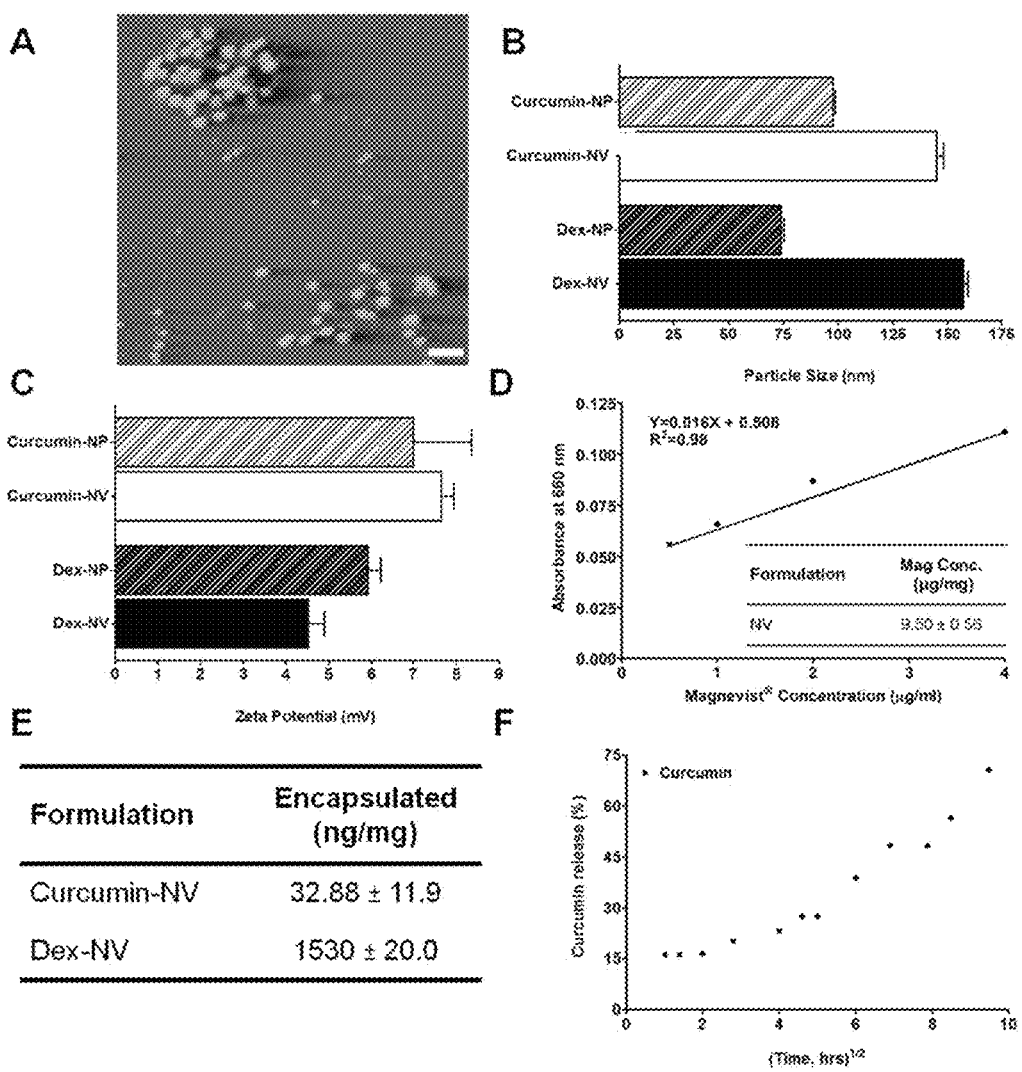
FIG. 8. (A) Atomic force micrograph of nanovehicles (NVs). Scale bar, 250 nm. (B) Average particle size of curcumin or dexamethasone (dex) loaded nanoparticles (NP; without IgG4.1) and NVs (with IgG4.1) at pH 7.0 (n=3). (C) Effect of pH on the average zeta potential of curcumin or dexamethasone loaded NPs and NVs (n=5). (D) Magnevist® standard curve with 0.2 mM arsenazo (table insert). The amount of Magnevist® present on the surface of Magnevist®-NVs as determined by measuring absorbance in the presence of arsenazo II (660 nm). (E) The amount of encapsulated curcumin or dexamethasone in the NVs formulation. (F) The release of curcumin from the NVs.

The nanovehicles appeared as spherical particles on AFM micrographs and demonstrated size ranges between 90-100 nm (FIG. 8A). These values coincided with the particle sizes measured using dynamic light scattering method. Curcuminnanoparticles (devoid of IgG4.1) demonstrated a particle size of 97.8±1.8 nm (FIG. 8B) and a zeta potential of 7.0±1.9 mV (FIG. 8C). Similarly, dexamethasone-nanoparticles produced particles of 74.1±2.2 nm in size (FIG. 8B) with a positive zeta potential of 5.6±0.7 mV (FIG. 8C). However, when IgG4.1 was conjugated to the nanovehicle surfaces, the particle size increased to 145±5.4 nm for curcumin-nanovehicles and 157.6±3.4 nm for dexamethasone-nanovehicles (FIG. 8B). The corresponding zeta potential for curcumin-nanovehicles increased to 7.7±0.4 mV, but, the zeta potential for dexamethasone-nanovehicles dropped to 4.5±0.5 mV (FIG. 8C). All particle size and zeta potential measurements were conducted at physiological pH.

As determined by the Arsenazo III dye assay, the nanovehicles carried 9.5±0.6 μg/mg of Magnevist® on the surface (FIG. 8D). The amount of curcumin and dexamethasone encapsulated was 32.88±11.9 and 1.53±0.02 μg/mg of nanovehicles, respectively (FIG. 8E). Almost 75% of the total amount of curcumin encapsulated in the nanovehicles was released within 90 hours (FIG. 8F).

Figure 9:
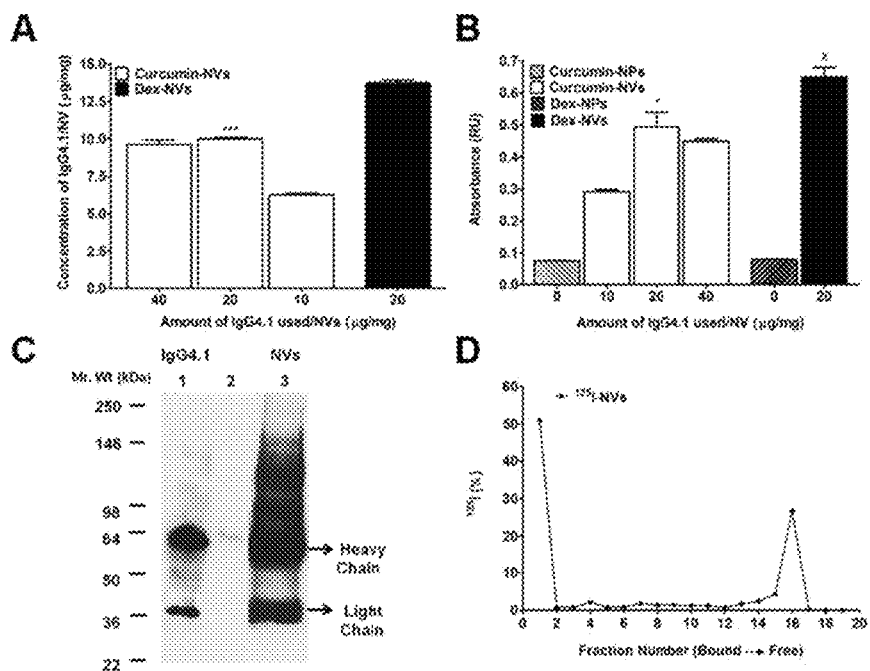
FIG. 9. (A) The amount of IgG4.1 retained in curcumin or dexamethasone (dex) loaded nanovehicles (NVs; contains IgG4.1). *$p<0.05$ (n=3); 20 μg of IgG4.1/mg curcumin-NVs vs 10 μg of IgG4.1 g/mg curcumin-NVs. (B) Binding of NVs to 10 μg/ml fibrillar DutchAβ40. *$p<0.005$ (n=3); 14 mg of IgG4.1/mg curcumin-NVs and dexamethasone-NVs vs 7 mg of IgG4.1/mg curcumin-NVs. (C) Substantiation of IgG4.1 conjugation to the NVs by Western blot. (D) The percentage of free and bound $^{125}$I in the $^{125}$I-IgG4.1 conjugated nanovehicle formulation as shown by paper chromatography.

The conjugation of IgG4.1 to nanovehicles was optimal when 20 μg of IgG4.1 per milligram of nanovehicles was used for the carbodiimide conjugation. This resulted in 10.0±0.1 μg and 14.6±0.4 μg of IgG4.1 per milligram of curcumin-nanovehicles and dexamethasone-nanovehicles, respectively (FIG. 9A). Both these nanovehicles have shown 5-7 fold higher binding to DutchAβ40 compared to the nanoparticles without IgG4.1 (FIG. 9B). However, no net change in IgG4.1 conjugated to nanovehicles or the ability of nanovehicles to bind to DutchAβ40 was observed when the IgG4.1 amount was increased to 40 μg per milligram of nanovehicles for the carbodiimide conjugation (FIG. 9A-B). Based on these observations, the optimal concentration of IgG4.1 for nanovehicle conjugation was determined as 20 μg/mg of nanovehicles (FIG. 9B). Western blot analysis verified the successful IgG4.1 conjugation to the nanovehicles (FIG. 9C).

To evaluate the plasma pharmacokinetics and brain uptake of the nanovehicles as well as to elucidate their biodistribution using SPECT imaging, the IgG4.1 on the nanovehicle surface was radioiodinated using Chloramine-T reaction. Paper chromatography data presented in FIG. 9D showed that the $^{st}$ and the $16^{th}$ paper fractions contained the most radioactivity. The radioactivity accumulated in the first fraction (origin) was most likely from the nanovehicles, whereas the radioactivity from the later fraction was due to the free $^{125}$I, running at the solvent front.

Migration of Nanovehicles Towards DutchAβ40 Treated BBB Monolayers In Vitro.

Figure 10:
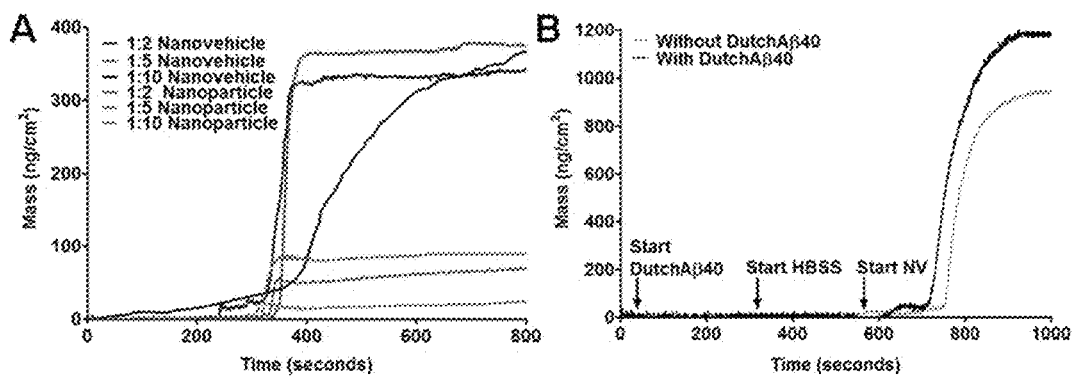
FIG. 10. (A) Mass change of various dilutions of nanoparticles (without IgG4.1) and nanovehicles (with IgG4.1) to bare gold sensors. (B) Mass change of nanovehicles in DutchAβ40-treated (treatment) or HBSS treated (control) Madin Darby canine kidney (MDCK) cells.

When the nanovehicles are injected into the systemic circulation, they are subjected to extensive dilution. To investigate the dilution effect on the margination of the nanovehicles from the blood flow to the vessel wall, QCM-D method was employed. Nanovehicles passing through a microfluidic channel migrated towards the naked quartz crystal more effectively than the nanoparticles at all dilutions. Although, dilution brought noticeable changes in the kinetics and the extent of margination, nanovehicles still maintained superior margination than the nanoparticles (FIG. 10A). The margination of nanovehicles towards the MDCK cell monolayer grown on the surface of the quartz crystal was 3-fold greater than that towards the bare sensor. When the cell monolayer was treated with DutchAβ40, the mass of nanovehicles bound to the sensor was determined to be 1190 ng/cm$^2$, whereas the binding to HBSS-treated cell-sensors was 970 ng/cm$^2$ (FIG. 10B). Furthermore, nanovehicles showed a faster margination towards DutchAβ40 treated cell monolayer than towards the HBSS treated monolayer.

Uptake of Nanovehicles by the Human BBB Model In Vitro.

Figure 11:
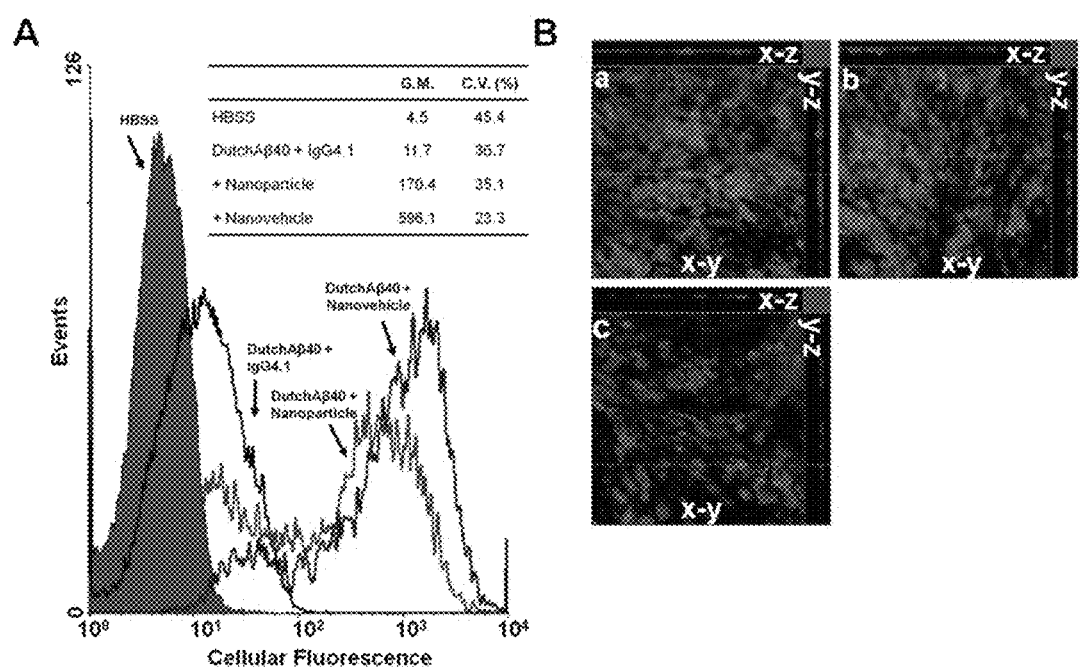
FIG. 11. (A) The uptake of a) HBSS- (control), b) alexafluor647 (AF647)-IgG4.1-, c) AF647-nanovehicles in HBSS-, d) AF647-nanovehicles in DutchAβ40-treated hCME cells as seen using flow cytometry. G.M. denotes geometric mean and C.V. denotes coefficient of variance. $p<0.001$: AF647-nanovehicles in DutchAβ40-treated cells as compared to all other treatments. (B) The uptake of a) nanovehicles in HBSS-, b) nanovehicles in chlorpromazine- c) nanovehicles in nystatin-treated human brain microvascular endothelial cell (hCMEC) monolayer as seen using laser confocal microscopy. The x-y plane images were obtained from the center of the z-stack. The AF647 nanovehicles are shown in red fluorescence and the cell nucleus with blue fluorescence.

The uptake of AF647-nanovehicles by the polarized hCMEC/D3 monolayers, a well characterized human BBB model, was determined by quantifying the amount of intracellular AF647 fluorescence using flow cytometry. Uptake of AF647-nanovehicles by the hCMEC/D3 cells pre-treated with DutchAβ40 showed a 16-fold increase than by the monolayers pre-treated with HBSS (FIG. 11A). However, a modest 2-fold increase in AF647-IgG4.1 antibody (no nanovehicle) uptake was observed in F-DutchAβ40 treated hCMEC/D3 cells than in those treated with HBSS (FIG. 11A).

The z-stack images of hCMEC/D3 cell monolayers treated with chlorpromazine (FIG. 11B.iii), an inhibitor of clathrin mediated endocytosis, demonstrated a substantially lower uptake of AF647-Nanovehicles than the hCMEC/D3 monolayers treated with HBSS (FIG. 11B.i). However, the hCMEC/D3 monolayers treated with nystatin (FIG. 11B.ii), a caveolae mediated endocytosis inhibitor, did not show appreciable differences in the uptake of AF647-Nanovehicles compared to those treated with HBSS. (FIG. 11B.i).

Biodistribution of Nanovehicles

Figure 12:
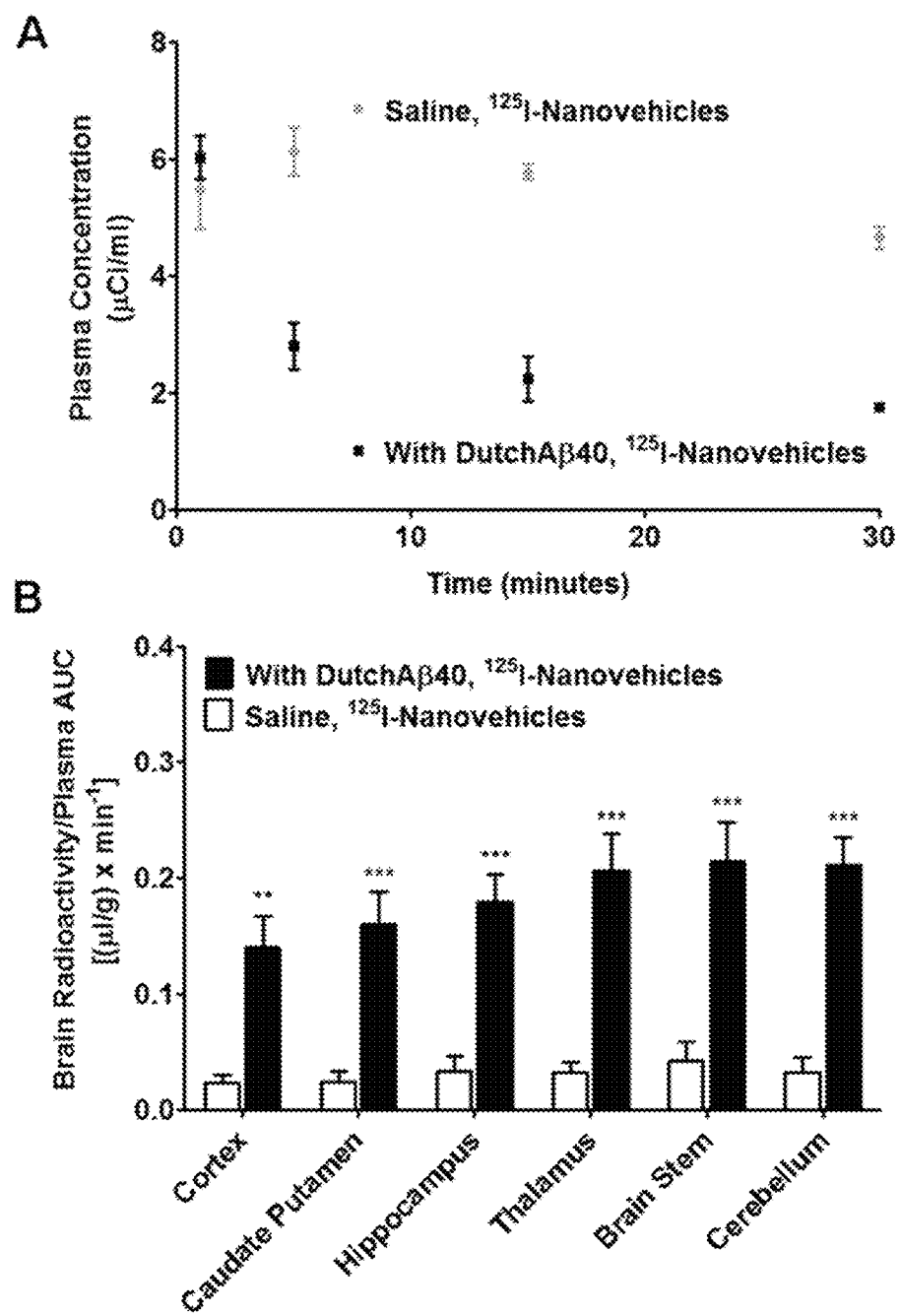
FIG. 12. (A) The plasma kinetic profile of $^{125}$I-nanovehicles in wild type (WT) mice treated with or without DutchAβ40. (B) Brain distribution of $^{125}$I-nanovehicles in WT mice treated with or without DutchAβ40 (D40). p<0.01 (n=3) or *p<0.001 (n=3); 125I-nanovehicles in DutchAβ40-treated mice vs untreated mice in the respective brain region.

The distribution of $^{125}$I-nanovehicles/mg of brain tissue normalized by the plasma AUC was remarkably higher in DutchAβ40 treated versus saline treated mice (FIG. 12B). The plasma AUC0-30 min and volume of distribution at steady state (Vss) was greater in HBSS pre-injected mice than in DutchAβ40 pre-injected mice. But no appreciable differences in either the elimination rate constant (Kel) or clearance (CL) was observed in DutchAβ40 or HBSS pre-injected mice (Table 1).

TABLE 1

Plasma pharmacokinetic parameters of $^{125}$I-nanovehicles in wild type (WT) mice.

| Parameter | $^{125}$I-Nanovehicles | | p |
|---|---|---|---|
| | With DutchAβ40 | Without DutchAβ40 | |
| AUC (min × μCi/ml) | 309.6 ± 108.3 | 753.3 ± 129.8 | * |
| Kel (min$^{-1}$) | 0.002 ± 0.0009 | 0.0035 ± 0.0014 | N.S. |
| Cl (ml/min/μCi) | 0.077 ± 0.032 | 0.054 ± 0.012 | N.S. |
| Vss (ml/μCi) | 40.37 ± 5.18 | 18.79 ± 0.14 | ** |

Data presented as mean ± standard error of the mean.
* p < 0.05,
** p < 0.01
N.S., not significant

TABLE 2

Gadolinium (Gd) concentration (mM) and respective T1 and T2 relaxation times.

| Nanovehicles (mM Gd) | T$_1$ (ms) | T$_2$ (ms) |
|---|---|---|
| 0.72 | 2076.7 | 78.0 |
| 1.44 | 1972.4 | 77.5 |
| 2.87 | 1694.4 | 76.4 |
| 5.74 | 1238.7 | 72.7 |

TABLE 3

Relaxivity of nanovehicles at 21.1 T with goodness of fit indicated by adjusted R$^2$.

| | r$^1$ (mM$^{-1}$s$^{-1}$) | Adjusted R$^2$ | r$^2$ (mM$^{-1}$s$^{-1}$) | Adjusted R$^2$ |
|---|---|---|---|---|
| NVs | 0.072 | 0.999 | 0.101 | 0.915 |

Ability of Nanovehicles to Target Cerebrovascular Amyloid

Figure 13:
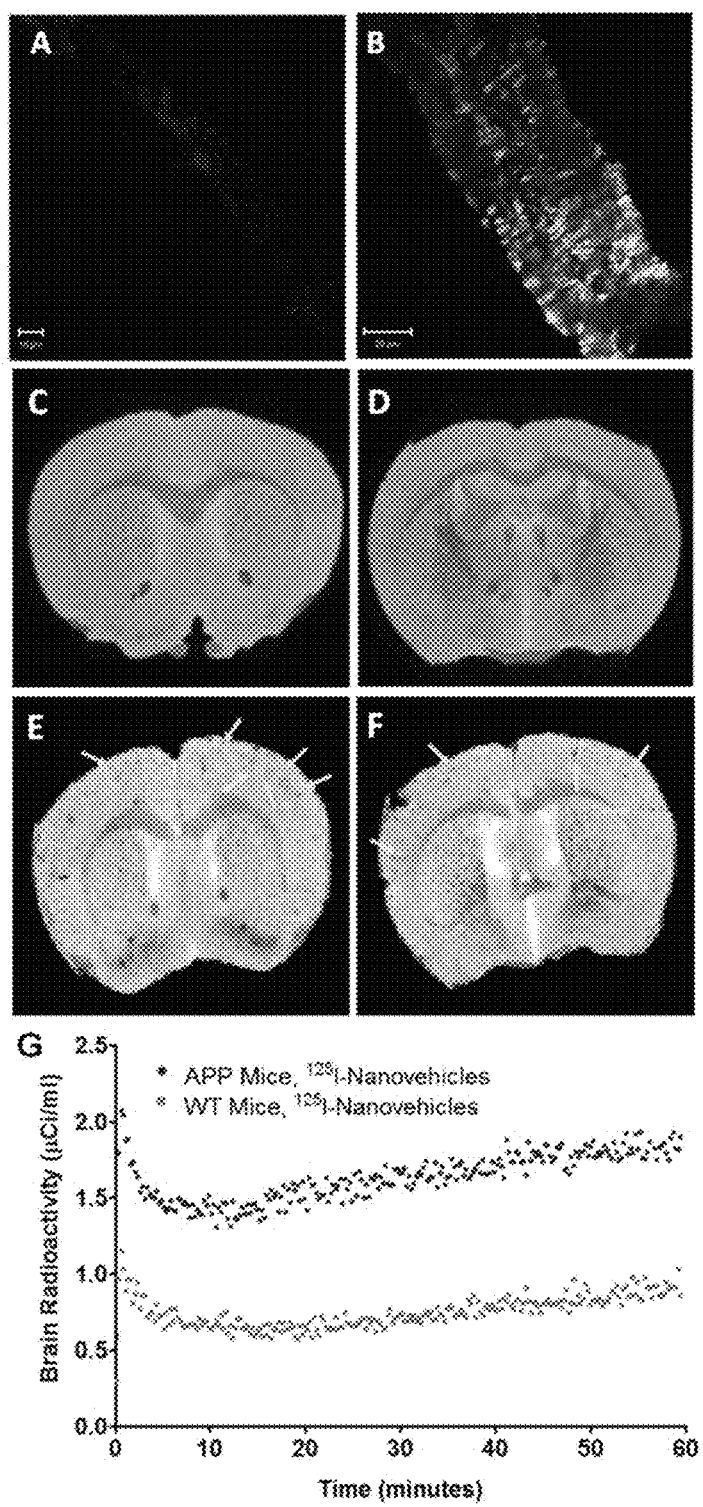
FIG. 13. Uptake of (FA) AlexaFluor 647 (AF647)-nanovehicles in brain arteriole of wild type mouse. (B) Uptake AF647-nanovehicles in brain arteriole of APP transgenic mouse. The blue fluorescence is to visualize structure, AF647-nanovehicles emits red fluorescence and Thioflavin S emits green fluorescence. Magnetic resonance imaging of: (C-D) Magnevist®-nanovehicles in wild type (WT) mice, (E-F) Magnevist®-nanovehicles in APP transgenic mice. Arrows indicate Magnevist®-nanovehicles ability to provide enhanced contrast. (G) Brain uptake of $^{125}$I-nanovehicles in APP transgenic mice vs $^{125}$I-nanovehicles in WT mice as determined by single photon emission computed tomography (SPECT).

To determine the co-localization of nanovehicles with the cerebrovascular amyloid, 45 mg of AF647-nanovehicles in 200 µl of normal saline was injected via external carotid artery to 24-month old Alzheimer's disease transgenic mouse (Tg2576) or aged-matched WT mice. The AF647-TNVs showed enhanced cerebrovascular uptake in Tg2576 mouse and selectively targeted amyloid deposits in the vascular wall (FIG. 13B). However, AF647-TNVs were confined to the cerebrovascular endothelium and did not show detectable permeation into the vascular wall in WT mice (FIG. 13A).

Nanovehicles as Imaging Agents

Coronal MRI brain scans clearly demonstrated the ability of nanovehicles to provide enhanced contrast throughout the cortex and especially in the radiating arterioles of 2-year-old Tg2576 mice (FIG. 13E-F) but not in aged-matched WT mice (FIG. 13C-D). Live dynamic SPECT imaging was conducted by injecting 400 µCi of $^{125}$I-nanovehicles in two-year-old Tg2576 mice or aged matched WT mice. After the subtracting the radioactive counts circulating in the cerebral vasculature from the total brain radioactivity, which was quantified by dynamic SPECT imaging, nearly 2-fold increase in the cerebrovascular accumulation of nanovehicles was observed in Tg2576 mice than WT mice (FIG. 13G).

Discussion

For targeting the cerebrovascular amyloid, the nanoparticles are expected to cross the BBB and be retained in the basement membrane, where cerebrovascular amyloid is deposited. To accomplish this goal, the nanovehicles are expected to be smaller than 150 nm to allow for the endothelial cell uptake; yet larger than 100 nm to not migrate through the basement membrane matrix into the brain parenchyma. Therefore, curcumin- and dexamethasone-nanovehicles were formulated to maintain a size range of 140-160 nm (FIG. 8B). Furthermore, the nanovehicles were formulated to maintain a positive zeta potential of 5.0-7.0 mV (FIG. 8C) to facilitate their adsorptive endocytosis at the negatively charged BBB endothelium. Previous studies have shown that this zeta potential range was adequate in promoting transcytosis of the nanovehicles [13].

The amount of curcumin encapsulated in the nanovehicles was around 33 ng curcumin/mg nanovehicle (FIG. 8E). When the nanovehicles were exposed to the aqueous environment, approximately 75% of the entrapped curcumin was released within 90 hours (FIG. 8F). This sustained delivery of curcumin to the cerebral vasculature is expected to reduce the inflammation at the affected site. Curcumin possesses anti-oxidant, anti-inflammatory and anti-amyloidgenic properties [14-16]. Curcumin also exists in a dynamic equilibrium of keto and enol tautomers, the latter of which can target Aβ aggregates [17]. Dexamethasone, on the other hand, has been shown to significantly reduce inflammation and the occurrence of microhemorrhages [18]. Of these compounds, curcumin has low bioavailability due to poor solubility and higher enzymatic degradation. To circumvent these issues, HPβCD's ability to complex hydrophobic curcumin was utilized and the resultant HPβCD [curcumin] was encapsulated in the nanovehicles.

The amount of IgG4.1 conjugated to the nanovehicle surface was quantified using BCA protein assay. A substantial increase in the amount of IgG4.1 conjugated to the nanovehicle surface was observed when the concentration of IgG4.1 used in the carbodiimide reaction was doubled from 10 to 20 µg of IgG4.1 per mg of nanovehicle (FIG. 9A). This concentration also resulted in enhanced binding of the nanovehicle to DutchAβ40 (FIG. 9B). However, a further increase in IgG4.1 from 20 to 40 µg did not further improve the nanovehicle binding to DutchAβ40 (FIG. 9B). Hence, 20 µg IgG4.1/mg nanovehicle was considered as the optimal concentration for the conjugation.

The ability of various nanovehicles to marginate towards the BBB endothelium was evaluated in vitro using QCM-D. This technique allows for quantifying the mass of nanoparticles adsorbed to an oscillating quartz crystal at the floor of the microfluidic channel through which the nanovehicle suspension is passed at various flow rates. The quartz crystal oscillation frequency is decreased proportionately to the mass of nanovehicles adsorbed on the crystal surface. Based on the frequency changes, the mass bound to the quartz crystal was calculated using the Sauebrey equation in Qtools® software (Västra Frölunda, Sweden). The nanoparticles without IgG4.1 showed minimal binding and migration to the bare gold sensor, whereas the nanovehicle with IgG4.1 showed a 3-fold increase in binding to the sensor. Dilution of the nanovehicle suspension did not affect the extent of nanovehicle binding to the sensor (FIG. 10A); this indicates that the ability of the nanovehicle to marginate to the vessel wall is not substantially disrupted when they are diluted in the systemic circulation. To evaluate the ability of these nanovehicles to marginate towards the BBB endothelium in the cerebral vasculature exposed to Aβ proteins, MDCK cells were seeded on the gold sensors and treated with DutchAβ40. The nanovehicles showed high binding to both HBSS and DutchAβ40 treated cell surface compared to the bare sensor (FIG. 10B). However, in the presence of DutchAβ40, the nanovehicles showed faster migration rate and increased cellular targeting than in case of HBSS treated cells.

Internalization of AF647-nanovehicles in DutchAβ40 treated hCMEC/D3 endothelial cells was twice as much as in HBSS treated cells (FIG. 11A). On the other hand, AF647-IgG4.1 exhibited only a slight increase in the uptake by DutchAβ40 treated cells compared to HBSS treated cells (FIG. 11A), which indicates a modest uptake of AF647-IgG4.1 compared to the nanovehicles. It can be inferred from these results that the nanovehicle surface covered by the protonated chitosan chains is most likely responsible for the enhanced uptake of nanovehicles by the hCMEC/D3 endothelial cells. The IgG4.1 conjugated to the nanovehicle surface does not play a major role in enhancing the cellular uptake of nanovehicles, but facilitates their intracellular movement along the path of DutchAβ40 accumulation (FIG. 11A).

The uptake of AF647 nanovehicles in the nystatin treated hCMEC/D3 endothelial cell monolayer was significant lower as compared to the monolayers treated with chlorpromazine or HBSS and nanovehicles (FIG. 11B). On the other hand, no differences in uptake were seen between the monolayers treated with HBSS and nanovehicles or chlorpromazine and nanovehicles (FIG. 11B). This demonstrates that caveolae mediated uptake plays a major role in the uptake of nanovehicles.

The plasma pharmacokinetics and the brain uptake of nanovehicles was elucidated in WT mice pre-injected with 500 µg of DutchAβ40. Previous studies have shown that DutchAβ40, when injected intravenously, accumulates primarily in the cerebral vasculature. Hence, the pre-injection of DutchAβ40 into WT mice provides a more reliable CAA model rather than the Tg2576 mice. Although, these AD transgenic mice were shown to express cerebrovascular amyloid, the extent of vascular amyloid, which drives the biodistribution of nanovehicles, varies significantly from animal to animal. The plasma pharmacokinetics of nanovehicles in the presence of DutchAβ40 is altered significantly and mimicked the biodistribution of DutchAβ40, which suggests that the nanovehicles are responsive to the presence of amyloid in vivo. However, the elimination rate constant (kel) of $^{125}$I-nanovehicles did not increase to match that of DutchAβ40, which could have resulted in their rapid elimination from the systemic circulation. Based on the observations that the volume of distribution of nanovehicles increased and AUC decreased in DutchAβ40 treated mice as compared to saline treated mice (FIG. 12A), it can be inferred that the changes in nanovehicle distribution due to the presence of DutchAβ40 is primarily due to better tissue partitioning from the systemic circulation. In agreement with these observations, the distribution of $^{125}$I-nanovehicles to all brain regions was 2 to 3-fold higher in DutchAβ40 treated mice than in the saline treated mice (FIG. 12B).

Isolation of vessels from Tg2576 mice treated with AF647-nanovehicles showed co-localization of the nanovehicles with the cerebrovascular amyloid, thus confirming the ability of nanovehicles to target amyloid within the cerebral vasculature (FIG. 13B). This selective targeting could facilitate site-directed release of curcumin, dexamethasone, or any other antioxidant/immunosuppressant to reduce cerebral hemorrhages resulting from inflammation in CAA.

In WT mice, the nanovehicles did not produce detectable MRI contrast (FIGS. 13C&D), whereas, high levels of contrast in the radiating arterioles was seen in Tg2576 mice injected with the nanovehicles (FIGS. 13E&F). These results demonstrate the ability of nanovehicles to detect cerebrovascular amyloid in AD transgenic animals. Similar confirmation was also obtained using SPECT/CT imaging, which showed a 6-fold increase in the accumulation of $^{125}$I-nanovehicles in Tg2576 versus WT mice (FIG. 13G).

Conclusions

Described herein is a hydrophilic nanovehicle capable of entrapping hydrophobic drugs that selectively target CVA deposits. These nanovehicles are large enough to be retained in the cerebral vasculature, yet small enough to permeate the BBB endothelium. The nanovehicles can be readily equipped with various imaging agents to facilitate early diagnosis of CAA using a variety of diagnostic tools such as MR, SPECT and fluorescent imaging. These nanovehicles were clearly proven to serve as effective diagnostic agents to detect CVA by MRI and SPECT modalities. In addition, they also displayed the potential to carry therapeutic agents to reduce inflammation associated with CAA, which is believed to trigger hemorrhages in CAA patient.

BIBLIOGRAPHY

[1] Calhoun M E, Burgermeister P, Phinney A L, Stalder M, Tolnay M, Wiederhold K H, et al. Neuronal overexpression of mutant amyloid precursor protein results in prominent deposition of cerebrovascular amyloid. Proc Natl Acad Sci USA. 1999; 96:14088-93.

[2] Jack C R, Jr., Marjanska M, Wengenack T M, Reyes D A, Curran G L, Lin J, et al. Magnetic resonance imaging of Alzheimer's pathology in the brains of living transgenic mice: a new tool in Alzheimer's disease research. Neuroscientist. 2007; 13:38-48.

[3] Poduslo J F, Hultman K L, Curran G L, Preboske G M, Chamberlain R, Marjanska M, et al. Targeting vascular amyloid in arterioles of Alzheimer disease transgenic mice with amyloid beta protein antibody-coated nanoparticles. Journal of Neuropathology and Experimental Neurology. 2011; 70:653-61.

[4] Poduslo J F, Ramakrishnan M, Holasek S S, Ramirez-Alvarado M, Kandimalla K K, Gilles E J, et al. In vivo targeting of antibody fragments to the nervous system for Alzheimer's disease immunotherapy and molecular imaging of amyloid plaques. J Neurochem. 2007; 102:420-33.

[5] Hsiao K, Chapman P, Nilsen S, Eckman C, Harigaya Y, Younkin S, et al. Correlative memory deficits, Abeta elevation, and amyloid plaques in transgenic mice. Science. 1996; 274:99-102.

[6] Agyare E K, Curran G L, Ramakrishnan M, Yu C C, Poduslo J F, Kandimalla K K. Development of a smart nano-vehicle to target cerebrovascular amyloid deposits and brain parenchymal plaques observed in Alzheimer's disease and cerebral amyloid angiopathy. Pharm Res. 2008; 25:2674-84.

[7] Jingou J, Shilei H, Weiqi L, Danjun W, Tengfei W, Yi X. Preparation, characterization of hydrophilic and hydrophobic drug in combine loaded chitosan/cyclodextrin nanoparticles and in vitro release study. Colloids Surface B Biointerfaces. 2011; 83:103-7.

[8] Saha T K, Ichikawa H, Fukumori Y. Gadolinium diethylenetriaminepentaacetic acid-loaded chitosan microspheres for gadolinium neutron-capture therapy. Carbohydr Res. 2006; 341:2835-41.

[9] Shikata F, Tokumitsu H, Ichikawa H, Fukumori Y. In vitro cellular accumulation of gadolinium incorporated into chitosan nanoparticles designed for neutron-capture therapy of cancer. Eur J Pharm Biopharm. 2002; 53:57-63.

[10] Poduslo J F, Curran G L, Wengenack T M, Malester B, Duff K. Permeability of proteins at the blood-brain barrier in the normal adult mouse and double transgenic mouse model of Alzheimer's disease. Neurobiology of Disease. 2001; 8:555-67.

[11] Poduslo J F, Curran G L. Increased permeability of superoxide dismutase at the blood-nerve and blood-brain barriers with retained enzymatic activity after covalent modification with the naturally occurring polyamine, putrescine. J Neurochem. 1996; 67:734-41.

[12] Rowatt E, Williams R J. The interaction of cations with the dye arsenazo III. Biochem J. 1989; 259:295-8.

[13] Jaruszewski K M, Ramakrishnan S, Poduslo J F, Kandimalla K K. Chitosan enhances the stability and targeting of immuno-nanovehicles to cerebro-vascular deposits of Alzheimer's disea se amyloid protein. Nanomedicine: Nanotechnology, Biology, and Medicine. 2012; 8:250-60.

[14] Yang F, Lim G P, Begum A N, Ubeda O J, Simmons M R, Ambegaokar S S, et al. Curcumin inhibits formation of amyloid beta oligomers and fibrils, binds plaques, and reduces amyloid in vivo. J Biol Chem. 2005; 280:5892-901.

[15] Goel A, Kunnumakkara A B, Aggarwal B B. Curcumin as "Curecumin": from kitchen to clinic. Biochem Pharmacol. 2008; 75:787-809.

[16] Lim G P, Chu T, Yang F, Beech W, Frautschy S A, Cole G M. The curry spice curcumin reduces oxidative damage and amyloid pathology in an Alzheimer transgenic mouse. J Neurosci. 2001; 21:8370-7.

[17] Yanagisawa D, Amatsubo T, Morikawa S, Taguchi H, Urushitani M, Shirai N, et al. In vivo detection of amyloid beta deposition using (1)(9)F magnetic resonance imaging with a (1)(9)F-containing curcumin derivative in a mouse model of Alzheimer's disease. Neuroscience. 2011; 184:120-7.

[18] Previti M L, Zhang W, Van Nostrand W E. Dexamethasone diminishes the pro-inflammatory and cytotoxic effects of amyloid beta-protein in cerebrovascular smooth muscle cells. J Neuroinflammation. 2006; 3:18.

Example 3

Theranostic Nanovehicles to Target Cerebrovascular Amyloid in Alzheimer's Disease Brain Introduction.

Cerebral amyloid angiopathy (CAA), characterized by pronounced accumulation of amyloid beta (Aβ) 40 and 42 proteins within the cerebral arteries and arterioles, currently affects 30% of individuals over 60 years of age and 85% of Alzheimer's disease (AD) patients.[1] In the early stages, CAA results in cerebrovascular inflammation, vascular dysfunction and microhemorrhages, but in advanced stages leads to lobar hemorrhages and massive strokes.[2]

Presumptive diagnosis of CAA is based upon cerebral hemorrhaging as seen using computerized tomography (CT), genetic pre-disposition and as well as clinical symptoms outlined by The Boston Cerebral Amyloid Angiopathy Group Guidelines including motor skill decline, memory loss, confusion, blurred vision and gradual loss of neurological skills.[3-6] However, patients with CAA can also be asymptomatic. Unfortunately, confirmation of presumptive diagnoses can only occur post-mortem. Moreover, treatment options are relatively non-existent, ineffective and only moderately reduce cerebrovascular inflammation or offer symptomatic relief. Cyclophosphamide is an example of an immunosuppressant used clinically to reduce severe inflammation and has shown to suppress symptoms of senile CAA.7 However, cyclophosphamide has severe systemic toxicity and undesirable side effects.

To address the deficiencies in diagnostics and therapeutics for CAA, described herein are theranostic nanovehicles (TNVs) loaded with cyclophosphamide and conjugated with a magnetic resonance (MR) imaging contrast agent, Magnevist®, to detect and treat CAA. These TNVs are 150-250 nm in diameter, which is small enough to be endocytosed by the brain endothelial cell. The positively charged chitosan in the TNV formulation is also expected to enhance adsorptive endocytosis in the brain endothelial cell. Furthermore, owing to the presence of the anti-amyloid antibody, IgG4.1, on the surface, TNVs recognize and bind to cerebrovasculature amyloid (CVA). Herein is disclosed the development and characterization of TNVs and their ability to target CVA in vitro and in AD.

Materials and Methods

The DutchAβ40 protein, a mutation of Aβ40 (E22Q), was obtained from the Mayo Clinic Protein Core Facility (Rochester, Minn.). IgG4.1 a monoclonal antibody raised against human fibrillar Aβ42 was developed at the Mayo Clinic (Rochester, Minn.).[8] Bicinchoninic acid (BCA) protein assay was obtained from Thermo Scientific (Rockford, Ill.). Polycarbophil was procured from Lubrizol (Wickliff, Ohio). Alexa Fluor 647 (AF647) was purchased from Invitrogen (Carlsbad, Calif.). Cyclophosphamide was obtained from MP Biomedicals (Solon, Ohio). Dulbecco's modified Eagle's medium (DMEM), fetal bovine were acquired from Mediatech Inc. (Manassas, Va.). Gold crystals (100 nm) were obtained from Biolin Scientific® (Sweden). All other chemicals were obtained from Sigma Chemical Co (St. Louis, Mo.).

Animals

All procedures were conducted according to the National Institutes of Health Guide on the Care and Use of Laboratory animals and approved by the Mayo Clinic Institutional Animal Care and Use Committee. Six week old wild-type (WT, B6/SJL) mice were obtained from Jackson Laboratory (Bar Harbour, Me.). Swedish Tg2576 transgenic mice were procured from Taconic (Germantown, N.Y.).

Cell Culture

Human brain microvascular endothelial cells (hCMEC/D3) were cultured as described.[9] Upon reaching 80% confluence, hCMEC/D3 cells were seeded on collagen coated Transwells® (12 mm, Costar, Cambridge, Mass.) which were maintained for 7 days at 95% $O_2$, 5% $CO_2$ and 37° C.

Nanoparticle Preparation

The polymeric nanocore without IgG4.1 conjugated to the surface is referred to as nanoparticle in this example.

Preparation of Magnevist® Conjugated to Chitosan

Magnevist® (90 mg/ml) was conjugated to 1.5 mg/ml medium MW chitosan (MW=190,000-310,000 Da) using the carbodiimide reaction at room temperature, pH 4.5 and 500 rpm.[10-12] The Magnevist® conjugated chitosan was dialyzed against distilled water using a dialysis membrane of molecular weight cut-off of 50,000 Da to remove free Magnevist®.

Nanoparticle Formation

Chitosan-polyacrylic acid nanoparticles (NPs) were prepared by slowly adding anionic charged polyacrylic acid (molecular weight (MW)=400,000 Da) to Magnevist®-chitosan in a 1:8, 1:10 or 1:16 ratio at pH 3.5 to form the polyelectrolyte complex. Chitosan polycarbophil NPs were prepared in a similar fashion, except using a 1:5, 1:8 or 1:16 ratio of polycarbophil to chitosan at pH 3.5.

Encapsulation of Cyclophosphamide

For cyclophosphamide encapsulation, a 1:5 ratio of cyclophosphamide:chitosan was added to the polycarbophil or polyacrylic acid solution and allowed to equilibrate for 30 min prior to the formation of nanoparticles.

Preparation of TNVs (Nanoparticles-IgG4.1)

To form TNVs, various concentrations of IgG4.1 (640, 320 or 160 μg IgG4.1/mg of TNV) was covalently conjugated to freshly prepared nanoparticles via carbodiimide conjugation at pH 5.0 as previously described.[13] To remove free IgG4.1 and cyclophosphamide, TNVs were subjected to ultracentrifugation at 171,000×g for 10 min. BCA assay was used to quantify the amount of IgG4.1 on the surface of the TNV per manufacturer protocol.

The TNVs were radiolabeled with $^{125}$I (PerkinElmer Life and Analytical Sciences, Boston, Mass.) using the chloramine-T reaction.[14] Free $^{125}$I was removed by dialysis (MWCO=1,000 Da) against phosphate buffered saline (PBS, pH 7.4).

TNV Characterization

Atomic force microscopy (AFM) was performed by mounting freshly prepared TNVs and imaging with a MultiMode Scanning Probe microscope (Veeco Metrology Inc., Plainview, N.Y.). Images were processed using NanoScope software (Veeco Metrology Inc., Plainview, N.Y.). Based on their characteristic shape, hereafter, the TNVs formed from chitosan and polyacrylic acid will be called spherical TNVs and those made from chitosan and polycarbophil will be referred to as saucer-shaped TNVs.

The zeta potential of TNVs before and after IgG4.1 conjugation was measured using a Brookhaven Zeta Plus machine (Brookhaven Instruments, Holtsville, N.Y.), whereas the particle size (hydrodynamic diameter) was determined using a BI-200SM dynamic laser light scattering system (Brookhaven Instruments, Holtsville, N.Y.).

Cibacron brilliant red, which binds to protonated amine groups on chitosan, was used to determine the amount of chitosan on the surface of spherical TNVs and saucer-shaped TNVs as described elsewhere.[15-17] The hydrolysis of chitosan was determined by placing 1.75 mg/ml of the particles in distilled water and allowing them to equilibrate for 3 days at room temperature with minimal shaking. The net change in chitosan concentration was evaluated by measuring the absorbance using a SpectraMax Plus spectrophometer (Molecular Devices, Sunnyvale, Calif.) at 570 nm in the presence of cibacron brilliant red. The amount of Magnevist® on the surface of spherical or saucer-shaped TNVs was quantified using 0.2 M Arsenazo III.[18] Briefly, the TNVs, with and without Magnevist®, were submerged in boiling water for 5 min. Differences in absorbance in the presence of Arsenazo III and water (negative control), TNVs without Magnevist® (positive control) or TNVs with Magnevist® was measured at 660 nm.

The immunoreactivity of various TNV formulations to DutchAβ40 was determined by an enzyme linked immunosorbent assay (ELISA) which utilizes a secondary antimouse IgG4.1 alkaline phosphatase antibody to evaluate the amount of IgG4.1 that reacted to DutchAβ40.[8] DutchAβ40 is a vasculotropic mutation of Aβ40 at amino acid 22 from glutamate to glutamine. DutchAβ40 demonstrates aggressive CVA accumulation which allowed for the creation of in vitro and in vivo models with ease.

In Vitro Characterization

The ability of TNVs to migrate and bind DutchAβ40 treated Madin Darby canine kidney (MDCK) cells was determined using quartz crystal microbalance-dissipation (QCM-D). Quartz sensors with gold electrodes, chosen for their high sensitivity and compatibility with these cells, were cleaned according to the manufacturer's protocol (QSense®; Västra Frölunda, Sweden). MDCK cells were seeded on the sensor surface (density=5,000 cells/sensor) and stored in a perspex box at 37° C. and 5% $CO_2$. MDCK culture medium consisted of 90% DMEM, 10% fetal bovine serum and 1× penicillin-streptomycin. After 5 days, cells were washed with HBSS with 15 mM hydroxyethylpiperazineethanesulfonic acid (HEPES) plus 0.1% bovine serum albumin (BSA) to block non-specific binding. The sensors were carefully mounted in the QCM-D chamber and a stable baseline was established by flowing Hank's balanced salt solution (HBSS)-HEPES at a rate of 0.1 ml/min at 37° C. Either 12.5 µg DutchAβ40 (treatment) or HBSS (control) were introduced, followed by 300 µl HBSS-HEPES to remove any free DutchAβ40. TNVs (625 µg) were then introduced, frequency changes were monitored and the TNV flow was continued until a stable baseline was achieved. The mass absorption to the crystal was calculated as follows:

$$\Delta m = \frac{C \Delta f}{n} \quad (1)$$

where $\Delta m$ is the change in mass, C is the mass sensitivity constant (17.7 ng·cm$^{-2}$·Hz$^{-1}$), $\Delta f$ is the change in frequency and n is the overtone number (n=5).

TNV targeting to the in vitro brain endothelial model was determined using laser confocal microscopy. The polarized hCMEC/D3 monolayer was transformed into an in vitro CAA model by pre-incubation with 25 µg/ml fluorescein isothiocyanante-DutchAβ40 (FITC-DutchAβ40; emits green fluorescence) protein.[17] NPs conjugated with AF647-IgG4.1 (i.e., TNVs; emits red fluorescence) were added to the in vitro hCMEC/D3 CAA model and incubated for 1 hr at 37° C. and 5% $CO_2$ with minimal shaking. The TNVs were removed, fixed with 4% paraformaldehyde, mounted on glass cover slips, stained with 4',6-diamidino-2-phenylindole (DAPI; Vector labs, Burlingame, Calif.; emits blue fluorescence) and subsequently imaged using an Axiovert 100 M microscope equipped with Zeiss LSM 510 laser confocal capabilities (Ex/Em: 488/520 nm FITC, 350/470 nm DAPI and 652/668 AF647; Carl Zeiss Inc., Thornwood, N.Y.). All images were obtained using identical microscopic settings to maintain continuity.

In Vivo Characterization

The radiolabeling efficiency of the bound and free $^{125}I$ in $^{125}I$-TNV formulation was determined using paper chromatography with PBS as the mobile phase. The biodistribution of the $^{125}I$-TNVs was determined by placing each WT mouse (18-25 g) under general anesthesia (1.5% isoflurane, 4 l/min $O_2$) followed by catheterization of the femoral artery and vein were catheterized. The DutchAβ40 protein (100 µl of 5 µg/µl; treatment) or normal saline (100 µl; control) was intravenously (IV) administered through the femoral vein and after 15 min, the $^{125}I$-TNVs (100 µCi) were administered IV. At various time intervals (1, 5, 15, 30, 45 and 60 min), 20 µl of blood was sampled via femoral artery. The plasma was recovered and subjected to trichloroacetic acid precipitation was performed on the plasma and analyzed using a two-channel gamma counter (Cobra II; Amersham Biosciences Inc., Piscataway, N.J.). Lastly, the mouse was subjected to transcardial perfusion with PBS to remove any unbound $^{125}I$-TNVs within the blood vessel walls of the cerebrovasculature. Brains were then removed, sectioned into six different regions, weighed and immediately assayed for $^{125}I$ radioactivity.

Pharmacokinetic parameters were estimated using non-compartmental pharmacokinetic analysis with uniform weighting with linear trapezoidal method (WinNonlin® Professional, version 5.2, Mountain view, Calif.) as described by the following function:

$$AUC \int_{t_2}^{t_1} = (t_2 - t_1)\frac{C_1 + C_2}{2} \quad (2)$$

where AUC is the area under the curve, $C_1$ and $C_2$ are plasma concentrations and $t_1$ and $t_2$ are the corresponding time points as estimated using WinNonlin®. The plasma clearance (CL), volume at steady state (Vss) and other pharmacokinetic parameters were also calculated using WinNonlin®.

Magnetic Resonance Imaging

All MR images were acquired using a 21.1 T vertical magnet with a bore diameter of 105-mm, built entirely at the National High Magnetic Field Laboratory (NHMFL).[19] The magnet was equipped with a Bruker Avance III spectrometer and acquisition was performed with ParaVision 5.1 (Bruker, Billerca Mass.) and a 64-mm inner diameter high performance gradient (Resonance Research Inc, MA).

MRI relaxometry measurements were carried with phantoms containing the Gd conjugated TNVs. Phantoms were created by diluting the TNVs in distilled water to obtain a concentration range of 0.10-6.5 µM Gd for the spherical TNVs and 0.3-27 µM Gd for the saucer-shaped TNVs. The solutions were injected into micro-capillary tubes and sealed with silicone gel (Dow Corning, Midland, Mich.). The tubes were imaged in sets of 7 using a 10-mm NMR tube (Wilmad-Labglass, Vineland N.J.). MR images were acquired using a 10-mm birdcage coil, tuned to a proton ($^1$H) resonance frequency of 900 MHz. Measurements were performed to quantify $R_1$ and $R_2$ relaxation for each sample. For both relaxation measurements, a single slice 2D spin-echo (SE) sequence was used with nine incrementing repetition times (TR=25-15000 ms) and 16 incrementing echo times (TE=8-124 ms) times for each respective contrast weighting. Both sequences were acquired with a matrix of 128×128, 1.0 mm slice thickness and 2 averages. Magnitude images were analyzed using Regions of Interest (ROIs) drawn to cover each individual micro-capillary as well as a noise ROI for baseline corrections. The ROI signal intensities were fitted by non-linear regression using the Levenburg-Marquadt algorithm in SigmaPlot 7.101 (SPSS Inc, Chicago, Ill.). For $R_2$ measurements, a single exponential decay function with baseline adjustment was employed while a single exponential growth was applied for $R_1$.

For ex vivo MR imaging, each 24 month old APP transgenic or aged-matched WT mouse (18-25 g) was placed under general anesthesia (1.5% isoflurane, 4 l/min $O_2$), the femoral vein catheterized and TNVs injected into each animal. After 3 hrs, animals were subjected to transcardial perfusion, followed by 4% paraformaldehyde fixation. Brains were removed, immersed in 4% paraformaldehyde. The excised brains were washed in buffered saline (PBS) for 24 hr prior to MRI. The brains were then placed individually in conical tubes containing flourinert (3M, St. Paul Minn.), a perfluorinated liquid with no $^1$H MRI signal. Brains were imaged in unison using a 35-mm RF birdcage coil resonating at 900 MHz. A 3D gradient recalled echo sequence (GRE) was used to generate high resolution $T_2$* weighted images. The matrix was set to achieve a 50-μm isotropic resolution. The echo (TE) and repetition (TR) times were 10 and 150 ms respectively resulting in a 15 hr scan time. The data set was processed with AMIRA 5.3.3 (Visage imaging, CA) to visualize the brain structure of interest and compare each individual brain in an accurate manner.

Single Photon Emission Computed Tomography (SPECT)

SPECT imaging was conducted through an IV bolus injection of 500 μCi of $^{125}$I-TNVs to 24 month old Tg2576 or aged-matched WT mice. Cerebral organ uptake of $^{125}$I-TNVs was determined by 15 sec/scan dynamic planar imaging, over a 40-60 min time range, using a low energy, high resolution parallel-hole collimator 12.5 cm FOV (X-SPECT, Gamma Medica Ideas Pre-Clinical Imaging, Northridge, Calif.). Single photon computed tomography (SEPCT) scans with corresponding computed tomography (CT) scans were taken at the completion of the dynamic phase and at set intervals on the XSPECT Gamma Medica scanner with the with the following parameters; low energy, high resolution parallel-hole collimator 12.5 cm FOV, 13:36 min acquisition time, 64 projections 10 sec per projection, reported resolution 1 to 2 um. The CT acquisition was a continuous circular orbit with a 50 um slice thickness, 256 images at 80 kVp with a 0.28 mA current, reported resolution 43 um. SPECT/CT and Dynamic images were acquired, processed and analyzed using Biomedical Image Quantification and Kinetic Modeling Software version 2.85 (PMOD Technologies, Switzerland). The brain uptake of TNVs at various time points was calculated using the following equation:

Brain uptake=$^{125}$I-TNVs in the brain−(residual plasma volume×$^{125}$I-TNVs in the plasma)  (3)

TNV targeting to CVA deposits was determined by placing 24 month old APP transgenic or aged-matched WT mice under general anesthesia (1.5% isoflurane, 4 l/min $O_2$), cannulating the left external carotid and administering 2.5 mg of saucer-shaped AF647-TNV. After 25 min, the heart was perfused with 2 mg/kg Evan's Blue in PBS (emits blue fluorescence) and 4% paraformaldehyde. The brain was subjected to gentle Dounce homogenization, centrifuged on (1.25, 1.5 or 1.75 M) sucrose gradient 92,000×g for 1 hr at 4° C. to isolate the blood vessels. Each fraction was stained with Thioflavin S (for CVA deposits, emits green fluorescence) and imaged using an Axiovert 100 M microscope with settings for fluorescein isothiocyanate (Ex/Em: 488/535 nm FITC, 550/610 nm Evan's Blue and 652/668 nm AF647).[13]

Statistics

All experiments were performed in triplicate and represented as mean±standard deviation. Statistical analyses were performed using one-way analysis of variance (ANOVA) followed by Tukey post-test using GraphPad Prism 5.0 software (Graph Pad Software Inc., San Diego, Calif.), with the exception of the pharmacokinetic study, which was compared by Student's t-test after WinNonlin® analysis. For brain distribution studies in WT type mice with and without DutchAβ40, treatments were compared by two-way ANOVA followed by Tukey post-test.

Results

In the following, the physicochemical characterization, formulation of NPs/TNVs from polyionic polymers, the ability of the TNVs to target CVA in vitro as well as in/ex vivo, and the ability of the TNVs to provide enhanced contrast for MR and SECT imaging are described below:

Preparation and Characterization of Nanoparticles (Spherical NPs or Saucer-shaped NPs; Without IgG4.1) and Theranostic Nanovehicles (Spherical TNVs or Saucer-shaped TNVs; With IgG4.1).

It is difficult to create a NP that meets ideal criteria in a single step. Therefore, these NPs were characterized in terms of particle size and zeta potential at each step. For example, 1:8 ratio of polycarbophil to chitosan showed an average particle size of 297±57.84 nm and a corresponding zeta potential of 5.96±0.37 mV at pH 4.0 (Table 1), (these NPs were free of Magnevist®, cyclophosphamide or IgG4.1). When the polycarbophil to chitosan ratio was decreased to 1:5 ratio, 214 nm sized particles with a near neutral zeta potential was seen. Alternatively, a 1:16 ratio generated 492 nm particles with a 9.39 mV potential at pH 4.0 (Table 1). However, when these saucer-shaped NPs were suspended in PBS at pH 7.0, the particle size varied in range from 18.45 to 2,339.3 nm with 66% of the particle population above 336 nm (data not shown). The corresponding zeta potential at pH 7.0 was 1.8±0.95 mV. Based upon these results, it was concluded that the optimal ratio of polycarbophil to chitosan was 1:8 which resulted in an acceptable particle size and positive zeta potential.

TABLE 1

Nanoparticle (NP) formulation optimization of spherical and saucer-shaped NPs at pH 4.0. NPs are free of Magnevist ®, cyclophosphamide and IgG4.1.

| Formulation | Polyacrylic acid:CS | Particle Size (nm) | Zeta Potential (mV) |
|---|---|---|---|
| Spherical NP | 1:8 | 290.5 ± 15.14 | 5.69 ± 0.46 |
| | 1:10 | 217.1 ± 7.91 | 25.1 ± 0.29 |
| | 1:16 | 496.7 ± 7.92 | 12.21 ± 0.59 |

TABLE 1-continued

Nanoparticle (NP) formulation optimization of spherical
and saucer-shaped NPs at pH 4.0. NPs are free of
Magnevist ®, cyclophosphamide and IgG4.1.

| Formulation | Polyacrylic acid:CS | Particle Size (nm) | Zeta Potential (mV) |
|---|---|---|---|
| Saucer-shaped NP | 1:5 | 214.5 ± 101.0 | 0.32 ± 0.09 |
| | 1:8 | 297 ± 57.84 | 5.96 ± 0.37 |
| | 1:16 | 492 ± 20.42 | 9.39 ± 0.24 |

Data is mean ± standard error of the mean.

Figure 14:
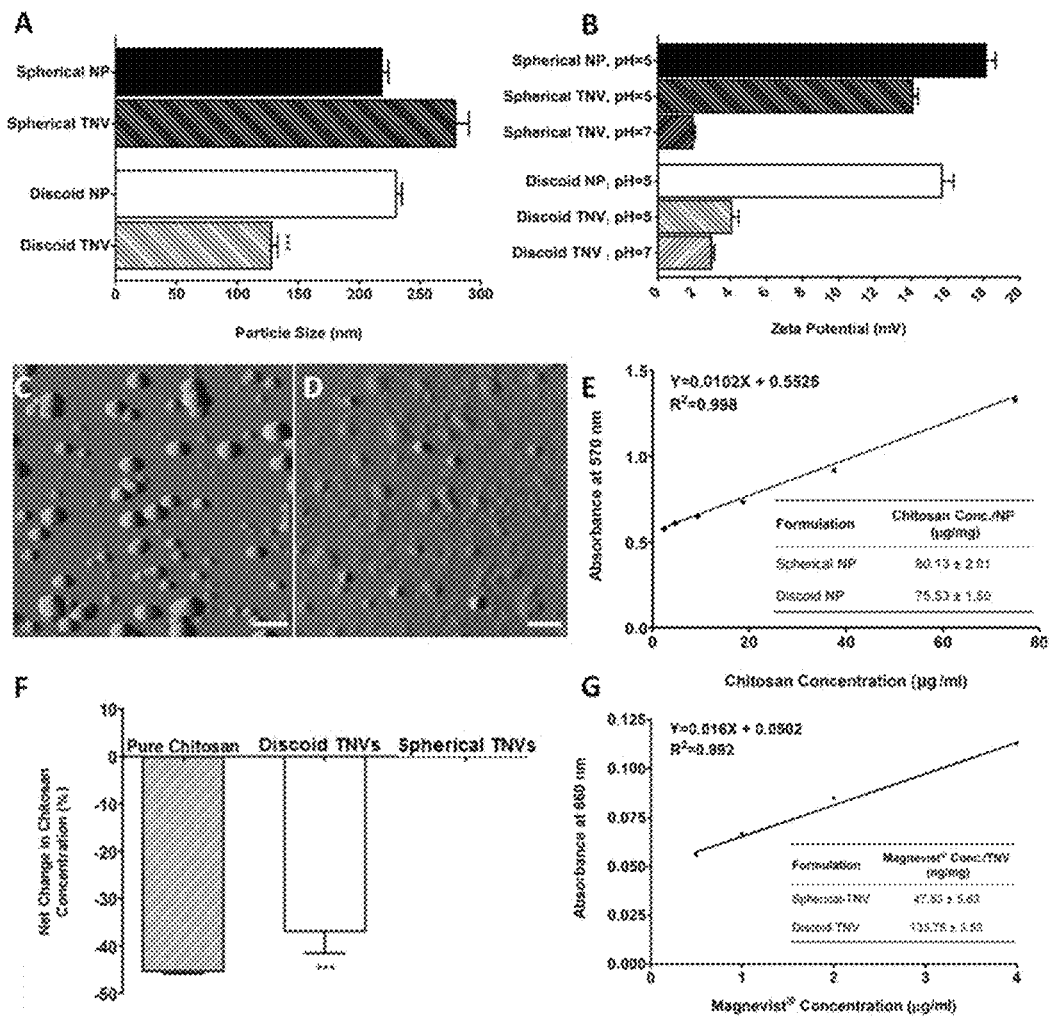
FIG. 14. (A) Average particle size of Magnevist® conjugated, cyclophosphamide (CYC) encapsulated spherical or saucer-shaped nanoparticles (NP; without IgG4.1) and theranostic nanovehicles (TNVs; with IgG4.1) at pH 5.0. *p<0.001 (n=3); saucer-shaped TNVs vs saucer-shaped NPs. (B) Effect of pH on the average zeta potential of Magnevist® conjugated cyclophosphamide encapsulated NPs and TNVs. (C) AFM micrograph of spherical NPs. Scale bar, 250 nm. (D) AFM of saucer-shaped NPs. Scale bar, 250 nm. (E) Chitosan standard curve with 150 µg/ml cibacron brilliant red (table insert). The amount of chitosan as determined by measuring the difference in absorbance of cibacron red in the presence and absence of spherical and saucer-shaped NPs. (F) The hydrolysis of pure chitosan, saucer-shaped and spherical TNVs in solution. *p<0.001 (n=3); saucer-shaped TNVs vs spherical TNVs. (G) Magnevist® standard curve with 0.2 mM arsenazo (table insert). The amount of Magnevist® on the surface of the TNVs as determined by measuring the difference in absorbance of arsenazo in the presence of TNVs with Magnevist®.

Following cyclophosphamide entrapment and Magnevist® conjugation, the size of saucer-shaped NPs was determined to be 230±9.35 nm (FIG. 14A); subsequent, IgG4.1 conjugation to form saucer-shaped TNVs generated a particle size of 128±9.40 nm at all pHs ranging from 4.0-7.0 (FIG. 14A). The corresponding zeta potential was 4.09±0.68 mV at pH 5.0 and 2.97±0.27 mV at pH 7.0 (FIG. 14B).

Alternatively, the optimal polyacrylic acid to chitosan ratio for blank NPs was 1:10, which produced an average particle size of 217.1±7.91 nm and corresponding zeta potential of 25.1±0.29 mV at pH 4.0 (Table 1). The particle size remained the same at pH 7.0 with a zeta potential of 12.96±2.1 mV (data not shown). These results were consistent with the literature showing the formation of a polyelectrolyte complex when polyacrylic acid is added drop-wise to the chitosan solution.[20] This resulted in a heterogeneous mixture of the polymers, but formed pH-stable NPs with small particle size (52-250 nm) and high zeta potential.[20,21] Alternatively, the 1:8 ratio produced 290.5 nm sized particles with zeta potential of 5.69 mV, while the 1:16 ratio gave particles of 496.7 nm in size with a 12.21 mV zeta potential. Magnevist®-chitosan cyclophosphamide encapsulated spherical NPs showed an average particle size of 218±9 nm at pH 4.0 and 7.0 (FIG. 14A) and a corresponding zeta potential of 18±0.93 mV at pH 7 (FIG. 14B). However, when conjugated with IgG4.1, these TNVs showed an average particle size of 279±20 nm and a corresponding zeta potential of 1.96±0.21 mV at pH 7.0 (FIG. 14A,B).

Morphology assessment of spherical NPs using AFM showed spherical shaped particles (FIG. 14C). Whereas, saucer-shaped NPs showed flat disk-shaped particles with a size range (58.23-182.74 nm) (FIG. 14D) consistent with that measured using dynamic light scattering.

Estimation of Chitosan and Magnevist® Content.

Cibacron brilliant red interacts with the protonated amine groups on chitosan to show enhanced absorbance at 570 nm. Using this assay, it was determined that the amount of chitosan on saucer-shaped- and spherical-NPs as 75.53±1.5 μg/mg and 80.13±2.01 μg/mg of NP, respectively (FIG. 14E). To assess changes in chitosan concentration, TNVs were incubated for 72 hrs and the net change in chitosan concentration was measured. Pure chitosan and saucer-shaped TNVs showed a 46% and 37% decrease in chitosan concentration, respectively (FIG. 14F). Spherical TNVs showed no significant changes in chitosan content (FIG. 14F). The amount of Magnevist® grafted on the surface of saucer-shaped and spherical TNVs was 133.76±3.5 ng/mg and 47.53±5.6 ng/mg of TNV, respectively (FIG. 14G).

Conjugation of Anti-Amyloid Antibody IgG4.1 to NPs

Figure 15:
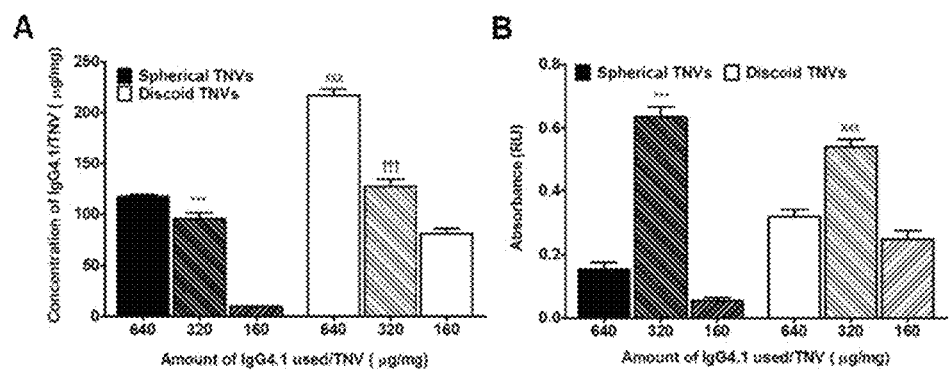
FIG. 15. (A) The amount of IgG4.1 retained on the surface of Magnevist® conjugated cyclophosphamide (CYC) encapsulated spherical or saucer-shaped theranostic nanovehicles (TNVs; contains IgG4.1). *p<0.001 (n=3); 0.32 mg/mg spherical TNVs vs 0.16 mg/mg spherical TNVs. xxxp<0.001 (n=3); 0.64 mg/mg saucer-shaped TNVs vs 0.32 mg/mg and 0.16 mg/mg saucer-shaped TNVs. +++p<0.001 (n=3); 0.32 mg/mg saucer-shaped TNVs vs 0.16 mg/mg saucer-shaped TNVs. (B) Binding of various TNVs to fibrillar DutchAβ40. *p<0.001 (n=3); 0.32 mg/mg spherical TNVs vs 0.64 and 0.16 mg/mg spherical TNVs. xxxp<0.001 (n=3); 0.32 mg/mg saucer-shaped TNVs vs 0.64 and 0.16 mg/mg saucer-shaped TNVs.

Increasing the concentration of IgG4.1 in the reaction mixture from 160 to 320 μg/mg of TNV significantly increased its conjugation to NPs (FIG. 15A). Further increasing the amount of IgG4.1 from 320 to 640 μg/mg showed only a moderate enhancement of IgG4.1 conjugation to TNVs, however, the binding to DutchAβ40 decreased (FIG. 15B). Therefore, it was determined that the ideal concentration of IgG4.1 for TNV conjugation without negatively impacting binding to DutchAβ40 in both cases was 320 μg/mg. Specifically, this corresponded to a mean absorbance value of 0.635±0.054 relative units (RU) for spherical TNVs and 0.542±0.039 RU for saucer-shaped TNV (FIG. 15B). In both cases, approximately a 6.5-8 fold increase was seen as compared to the control NPs (contains no IgG4.1), which lacked the ability to bind DutchAβ40.

Migration of TNV Towards Amyloid Treated Cells

Figure 16:
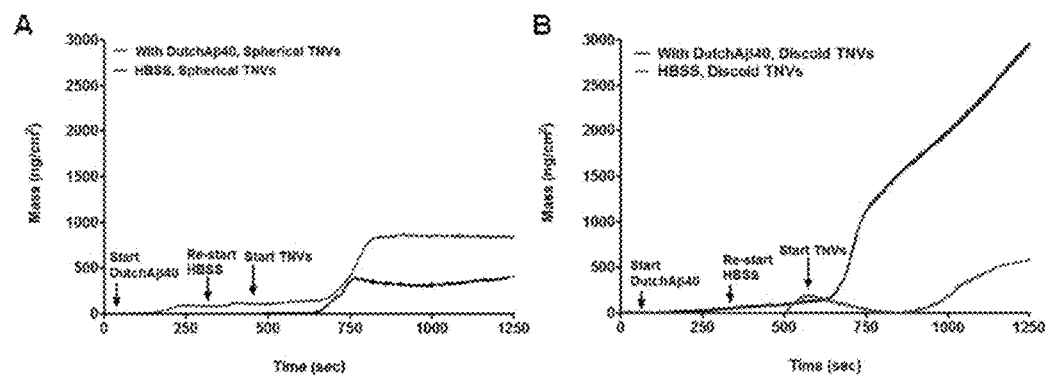
FIG. 16. Mass change of (A) spherical- or (B) saucer-shaped-theranostic nanovehicles (TNVs) in DutchAβ40 (D40)-treated (treatment) or HBSS treated (control) Madin Darby canine kidney (MDCK) cells.

Quartz crystals carrying a monolayer of MDCK on the surface of the sensors were carefully placed in a QCM-D chamber, equilibrated with HBSS-HEPES. The crystals were treated with either HBSS (control) or DutchAβ40 (treatment), washed with HBSS and then treated with TNVs. Data analysis was completed using Sauerbrey equation in Qtools® software (Västra Frölunda, Sweden) which measures the frequency changes observed when DutchAβ40 and then TNVs bound to the sensor. The binding of spherical and saucer-shaped TNVs to the model BBB monolayer treated with vasculotropic DutchAβ40 was shown to be 2-fold and 14-fold, respectively, compared to the HBSS treated cells (FIG. 16A,B). The saucer-shaped TNVs showed a faster migration and distribution rate to DutchAβ40 treated cells relative to spherical TNVs. The migration of TNVs to HBSS-treated cells was also poor. These results were consistent with ELISA assay, which also showed a 6-7 fold increase in TNV binding over control NPs to DutchAβ40.

Uptake of TNVs by Polarized hCMEC/D3 Monolayers

Figure 17:
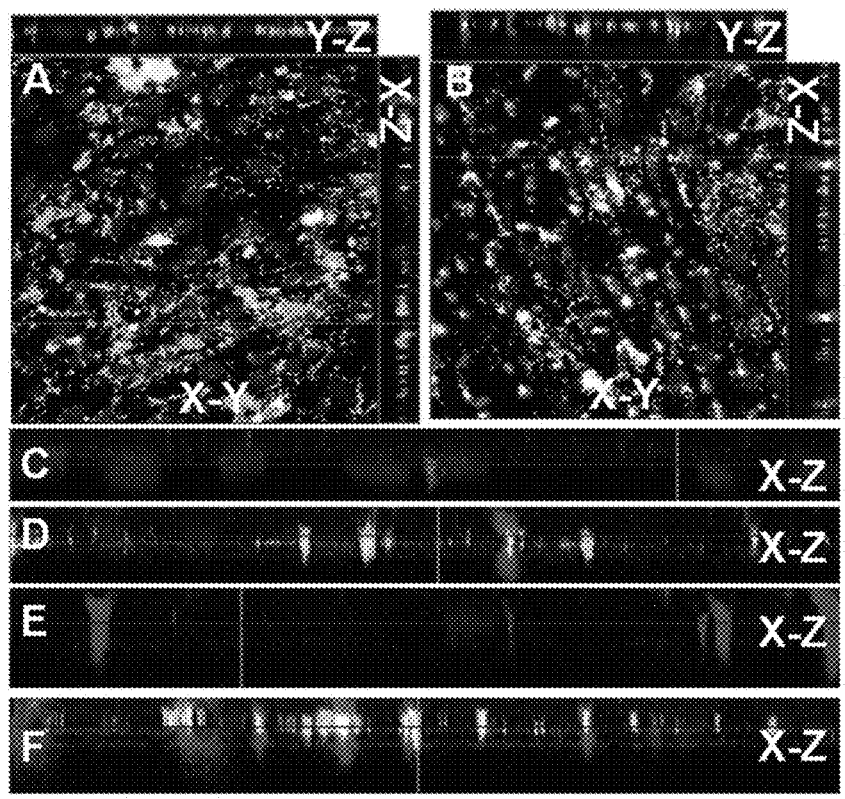
FIG. 17. Uptake of (A) AlexaFluor647 (AF647)-spherical TNVs in FITC-DutchAβ40-, (B) AF647-saucer-shaped TNVs in FITC-DutchAβ40-, (C) AF647-spherical TNVs in HBSS-, (D) AF647-spherical TNVs in FITC-DutchAβ40-, (E) AF647-saucer-shaped TNVs in HBSS- (F) AF647-saucer-shaped TNVs in FITC-DutchAβ40-treated BBMVEC monolayer as seen using laser confocal microscopy. The x-y plane images were obtained from the center of the z-stack. The AF647-TNVs is depicted with red fluorescence, FITC-DutchAβ40 in green and the cell nucleus in blue.

Z-stack images of FITC-DutchAβ40 treated hCMEC/D3 cell monolayers incubated with saucer-shaped AF647-TNVs showed a significant increase in fluorescent signal as compared to the monolayer treated with spherical AF647-TNVs (FIG. 17A-B). Furthermore, significantly higher fluorescence intensity was also seen when comparing FITC-DutchAβ40 treated and saucer-shaped AF647-TNVs or spherical AF647-TNVs compared with the HBSS (control) treated counterpart (FIG. 17C-F). More importantly, the co-localization of green (FITC-DutchAβ40) and red (saucer-shaped AF647-TNVs) fluorescence is indicative of the TNVs ability to selective target DutchAβ40-treated areas (FIG. 17F). On the other hand, spherical AF647-TNVs showed minimal to no ability to selectively target FITC-DutchAβ40 (FIG. 17D). Furthermore, x-y images obtained from the core of the z-stack indicated intracellular accumulation of all of the TNVs treatments. The most intracellular accumulation was seen in monolayers treated with both FITC-DutchAβ40 and saucer-shaped AF647-TNVs. Projection in the y-z and x-z orthogonal planes established the ability of the saucer-shaped AF647-TNVs to transcytose the hCMEC/D3 cell monolayer.

TNV Radio Labeling Efficiency

Figure 18:
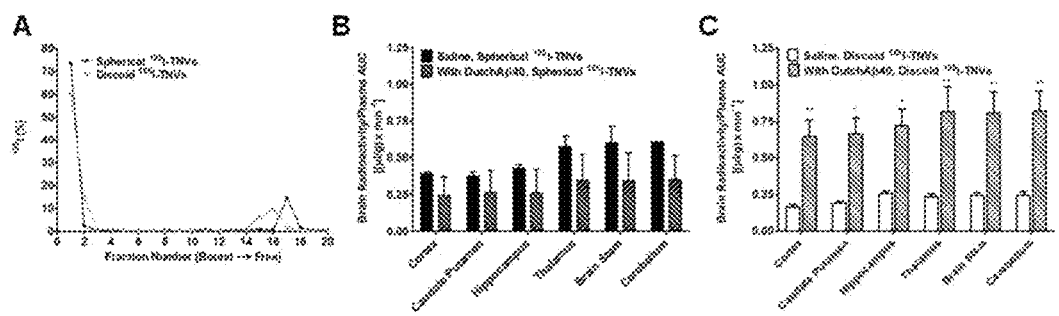
FIG. 18. (A) The percentage of free and bound $^{125}$I in the $^{125}$I-IgG4.1 conjugated spherical or saucer-shaped theranostic nanovehicle (TNV) formulations as shown using paper chromatography; brain distribution of (C) spherical TNVs and (B) saucer-shaped TNVs in WT mice treated with or without DutchAβ40. Comparisons among mean absorbance were made using 1-way ANOVA followed by Tukey post-test. *p<0.05 (n=3) or **p<0.01 (n=3); saucer-shaped TNVs in DutchAβ40-treated mice vs. untreated mice in the same brain region.
Figure 19:
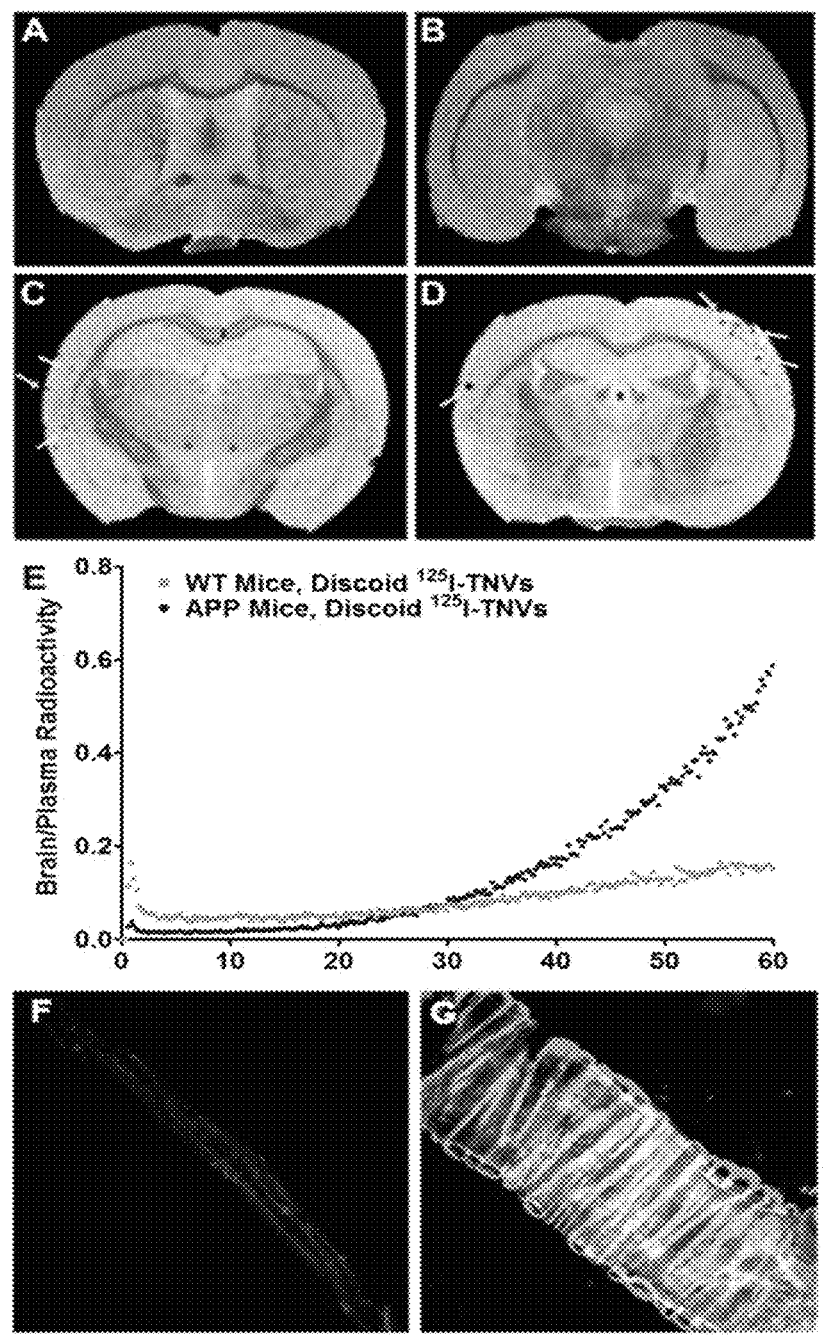
FIG. 19. Magnetic resonance imaging of: (A-B) Magnevist®-saucer-shaped theranostic nanovehicle (TNVs) in WT mice, (C-D) saucer-shaped TNVs in APP transgenic mice. Arrows indicate ability of TNVs to provide enhanced contrast. (E) Brain uptake of saucer-shaped $^{125}$I-TNVs in APP transgenic mice vs. saucer-shaped $^{125}$I-TNVs in WT mice as determined by single photon emission computed tomography (SPECT). (F) Uptake of AlexaFluor 647 (AF647)-saucer-shaped TNVs in brain arteriole of wild type mouse. (G) Uptake AlexaFluor 647 (AF647)-saucer-shaped TNVs in brain arteriole of APP transgenic mouse. The AF647-TNVs emits red fluorescence, Thioflavin S (fluoresces in response to amyloid) emits green fluorescence and the blue fluorescence is for structural purposes.

The amount of bound $^{125}$I in the $^{125}$I-TNV formulation was approximately 80% for both spherical and saucer-shaped TNVs, as seen with paper chromatography (FIG. 18A). The remaining 20% was shown to be free (unbound) $^{125}$I.

TNV Accumulation in Brain

Biodistribution profiles of TNVs in saline (control) or DutchAβ40-treated mice were investigated. The brain counts following transcardial perfusion were normalized by the wet weight of the brain region and plasma AUC. The spherical TNVs showed no enhanced brain accumulation in the DutchAβ40-treated versus saline treated mice (FIG. 18B). In addition, appreciable changes in the plasma pharmacokinetic parameters, such as AUC and elimination rate constant (Kel), were not seen in DutchAβ40 treated mice compared to that of saline treated mice (Table 2). Alternately, saucer-shaped TNVs showed enhanced accumulation in all brain regions of DutchAβ40 treated versus saline treated mice (FIG. 18C). Moreover, the AUC was significantly lower signifying the distribution of TNVs away from the plasma. The volume at steady state (Vss) is significantly higher in the case of DutchAβ40-treated mice, which again indicates greater distribution of saucer-shaped TNVs due to the presence of the DutchAβ40 protein (Table 3). The plasma clearance of saucer-shaped TNVs in saline treated mice was slightly higher than that of DutchAβ40 treated mice. These trends were similar to that of the plasma pharmacokinetic profiles of DutchAβ40 reported earlier.[22]

TABLE 2

Plasma Pharmacokinetic parameters of spherical $^{125}$I-theranostic probes (TNVs) in wild type (WT) mice.

| Parameter | Spherical TNVs | | |
|---|---|---|---|
| | With DutchAβ40 | Without DutchAβ40 | p |
| AUC (min × μCi/ml) | 315.49 ± 82.72 | 260.95 ± 108.5 | N.S. |
| Kel (min$^{-1}$) | 0.0021 ± 0.0011 | 0.005 ± 0.002 | N.S. |
| Cl (ml/min/μCi) | 0.081 ± 0.036 | 0.15 ± 0.09 | N.S. |
| Vss (ml/μCi) | 45.03 ± 7.06 | 29.36 ± 10.33 | N.S. |

Data presented as mean ± standard error of the mean.
N.S., not significant

TABLE 3

Plasma Pharmacokinetic parameters of saucer-shaped $^{125}$I-theranostic nanovehicles (TNVs) in wild type (WT) mice.

| Parameter | Saucer-shaped TNVs | | |
|---|---|---|---|
| | With DutchAβ40 | Without DutchAβ40 | p |
| AUC (min × μCi/ml) | 123.9 ± 4.11 | 419.67 ± 15.01 | *** |
| Kel (min$^{-1}$) | 0.0021 ± 0.008 | 0.0036 ± 0.0005 | N.S. |
| Cl (ml/min/μCi) | 0.096 ± 0.027 | 0.14 ± 0.011 | N.S. |
| Vss (ml/μCi) | 49.47 ± 5.87 | 21.58 ± 8.18 | * |

Data presented as mean ± standard error of the mean.
* p < 0.05,
** p < 0.001
N.S., not significant Ability of TNVs to Serve as Imaging Agents The spherical TNVs, despite its low gadolinium concentration has a much better ability to shorten the $T_1$ relaxation times as seen in Table 4. Consequently saucer-shaped TNVs will have a much larger $r_1$ and $r_2$ relaxivity (Table 5). This is likely due to the location of the gadolinium-ion on the spherical TNV molecule and its access to water, which is necessary to produce $T_1$ contrast.

TABLE 4

Gadolinium (Gd) concentration (mM) and respective $T_1$ and $T_2$ relaxation times

| Spherical TNVs (μM Gd) | $T_1$ (ms) | $T_2$ (ms) | Saucer-shaped TNVs (μM Gd) | $T_1$ (ms) | $T_2$ (ms) |
|---|---|---|---|---|---|
| 0.11 | 1834 | 76.3 | 0.30 | 1875 | 75.4 |
| 0.21 | 1517 | 75.6 | 0.60 | 1722 | 76.3 |
| 0.42 | 1796 | 76.4 | 1.19 | 1832 | 76.8 |
| 0.85 | 1800 | 76.1 | 2.38 | 1599 | 76.4 |
| 3.38 | 931 | 71.1 | 9.50 | 1389 | 74.2 |
| 6.75 | 577 | 65.1 | 27.0 | 975 | 73.2 |
| Water | 3056 | 81.2 | | 2875 | 78.8 |

TABLE 5

Relaxivity of spherical TNVs and saucer-shaped TNVs at 21.1 T with 2 goodness of fit indicated by adjusted $R^2$

| | $r^1$ (mM$^{-1}$s$^{-1}$) | Adjusted $R^2$ | $r^2$ (mM$^{-1}$s$^{-1}$) | Adjusted $R^2$ |
|---|---|---|---|---|
| Spherical TNVs | 177.6 | 0.97 | 340.9 | 0.98 |
| Saucer-shaped TNVs | 16.8 | 0.72 | 20.7 | 0.69 |

As seen with radio labeling, ex vivo MRI showed enhanced contrast in the radiating arterioles of the cortex of 2 year old APP transgenic mice treated with saucer-shaped NTPs versus aged-matched WT mice (FIG. 19A-D). Magnevist® is considered to be a $T_1$-agent due the bound gadolinium and its ability to shorten the longitudinal relaxation and create a signal enhancement. Here, the NPs are entrapped in endothelial cells within the arterioles which limit water access necessary for $T_1$-contrast. Therefore $T_2$-contrast becomes the dominant contrast mechanism which reduces MRI signal and creates signal voids as seen in FIG. 19. To enhance clinical relevance, live dynamic SPECT imaging was acquired by injecting 500 μCi of $^{125}$I labeled saucer-shaped TNVs in 2 year old APP transgenic or aged matched WT mice. Following acquisition of dynamic SPECT imaging and subsequent normalization of $^{125}$I counts in the brain to plasma, a 30% increase in extravascular accumulation of saucer-shaped TNVs in APP mice relative to WT control mice was observed (FIG. 19E). As expected, spherical TNVs lacked the ability to provide any MRI contrast in both 2 year old APP and aged matched WT mice (data not shown). As a result, dynamic SPECT was not acquired using spherical TNVs. Lastly, saucer-shaped AF647-TNVs showed the ability to line the endothelial wall in the arteries of WT mice (FIG. 19F). On the other hand, saucer-shaped AF647-TNVs in APP mouse showed the increased uptake of TNVs and ability of TNVs to selectively target amyloid deposits in the arterioles (FIG. 19G).

Discussion.

Although a plethora of diagnostic tools are available for CAA, most have decisive drawbacks such as low resolution and sensitivity. For instance, MR imaging is very promising, but requires delivery of large amounts of contrast agent to the brain. Studies have utilized monocrystalline iron oxide NPs (MIONS) to detect CVA deposits in the arterioles with some success.[13] Furthermore, these delivery systems do not offer the biocompatibilities and enhanced plasma residence time seen with polymeric nanoparticles made with chitosan. Moreover, conjugation of immunoglobulins on the MION surface could be challenging due to its lipophilic nature. The use of surfactants coating the MION surface blocks the functional groups necessary for carbodiimide conjugation. To combat these issues, chitosan is often used for its abundant amine functional groups to conjugate immunoglobulins, as well as its biocompatibility and biodegradable properties. Previously in vitro endothelial cell models have been used which show the ability of chitosan-based NPs to target CVA deposits, enhance transcytosis across BBB endothelial cells, and significantly reduce cerebrovasculature inflammation.[10,17] Herein disclosed are chitosan based TNVs to facilitate the detection and selective targeting of CVA amyloid using MR, fluorescent and preclinical dynamic SPECT imaging. Although it is difficult to design and create one TNV with the right diameter, surface charge and contrast agent, it is successfully demonstrated herein the development chitosan TNVs containing anionic polymers encompassing these important characteristics. Two types of nanoparticles were developed by taking advantage of electrophilic between positively charged chitosan and negatively charged polyacrylic acid or polycarbophil.

The spherical TNVs initially showed increased particle size and decreased zeta potential which are two major factors limiting the ability of particles to enter endothelial cells (FIG. 14A,B). These NPs, before and after IgG4.1 conjugation, were stable at every pH ranging from 4.0 to 7.0. However, saucer-shaped NPs showed a very large particle size range with increasing pH. In this case, chitosan coats polycarbophil, which is essentially acrylic acid cross-linked with glycol to form a saucer-shaped scaffold. The pKa of chitosan is 6.5 and the pKa of polyacrylic acid/polycarbophil is 4.75, but at physiological pH this would result in a weak positively charged chitosan and a strong negatively charged polycarbophil, thus modulating their electrostatic interactions. Polycarbophil also swells with increasing pH due to its tendency to gel at high pHs, resulting in increased particle size (data not shown). To combat this issue, chitosan was cross-linked to polyacrylic acid scaffold which is then tethered to the amine (from chitosan) and carboxylate functional groups through conjugation of an anti-amyloid antibody to yield a compact saucer-shaped nanovehicle. This was achieved through a single synthesis protocol to generate stabile saucer-shaped nanoparticles.

The amount of chitosan on the surface of the spherical NP and saucer-shaped NP were nearly identical as seen using cibacron brilliant red (FIG. 14E). However, a significant decrease in chitosan concentration was seen 3 days after equilibration of the saucer-shaped TNVs in distilled water (FIG. 14F). This decrease was similar to that of equilibrated pure chitosan solution, but not that of spherical TNVs, which indicated no net decrease, indicative of insufficient chitosan hydrolysis. It is posited that a lack of exposed chitosan hydroxyl groups in the spherical TNV formulation may result from the manner in which chitosan interacts with polyacrylic acid (FIG. 14F). In addition, the Magnevist® on spherical TNVs is only one-third of that present on saucer-shaped TNVs (FIG. 14G), supporting the notion of insufficient free amine groups available on the chitosan in spherical TNVs. Chitosan only covers the polycarbophil surface which reduces the bulk of interactions between chitosan and polycarbophil. This allowed for a greater amount of IgG4.1 to be loaded onto the saucer-shaped TNV surface as compared to spherical TNVs. In the later case, polyacrylic acid strands intermingles with that of chitosan and potentially converts the amine groups in the carbodiimide reaction which limits the extent of IgG4.1 conjugation (FIG. 15A). On the other hand, no increase in IgG4.1 concentration on the spherical TNV surface was seen when the concentration was raised from 320 to 640 μg/mg. In both saucer-shaped and spherical cases, the highest IgG4.1 binding was seen at 320 μg IgG4.1/mg TNV, which was chosen as the optimal concentration (FIG. 15B). The ability of putrescine modified IgG4.1 (PIgG4.1) conjugated TNVs to bind to DutchAβ40 was also investigated. Putrescine modification adds positive charges to the antibody that could increase permeability across the negatively charged endothelial cells. However, no binding was seen in either the PIgG4.1-saucer-shaped or PIgG4.1-spherical NP formulations (data not shown). The IgG4.1 was developed against fibillar Aβ42; previous studies have demonstrated that IgG4.1 exhibits substantially lower affinity to soluble Aβ.[23] Most of the plasma Aβ is not in the fibrillar form and hence may not saturate PIgG4.1 conjugated to the TNVs resulting from the double conjugation step involved in the PIgG4.1-TNVs formulation.

QCM-D allowed for the modeling the ability of nanoparticles to marginate from the blood flow towards the endothelial cells. Due to the limitations in maintaining physiological conditions in the compartment where the sensors are placed, a more durable polarized MDCK cell line was chosen, that is widely used as an in vitro BBB model.[24] As stated in the results, the binding and ability of spherical TNVs to target intracellular DutchAβ40 was relatively poor (FIG. 16A). In the case of saucer-shaped TNVs, the binding was enhanced 14-fold in DutchAβ40 treated MDCK cells compared to HBSS (control) cells. This correlates to the TNVs ability to target cellular Aβ proteins (FIG. 16B). The length of time it took saucer-shaped TNVs to reach and bind to DutchAβ40 treated cells was much faster compared to HBSS treated and DutchAβ40/spherical-TNV treated cells. This appears to contradict ELISA results that showed higher binding to DutchAβ40 with spherical TNVs. However, ELISA involves a simple incubation step where little to no movement of TNV solution occurs. But, in the QCM-D apparatus, TNVs are floated across the sensor surface at a rate of 0.1 ml/min. As a result, spherical TNVs were most likely carried away by the increased flow rate resulting in poor margination to the sensor and targeting intracellularly accumulated DutchAβ40. On the other hand, saucer-shaped shaped nanoparticles, as in the case of saucer-shaped TNVs, have a greater propensity to marginate from the bulk flow to the endothelium than do spherical shaped particles. Therefore, saucer-shaped TNVs likely had better cellular targeting owing to their disk shaped structure, resembling a platelet, which was previously shown to have better margination dynamics.

Poor transcytosis of spherical AF647-TNVs in DutchAβ40 treated cell monolayers was observed in z-series laser confocal micrographs as compared to DutchAβ40 and saucer-shaped AF647-TNVs treated counterpart (FIG. 17D, F). This may be due to an increased particle size and decreased zeta potential that reduces chitosan's ability to facilitate absorptive mediated endocytosis.[17] Furthermore, the extent of intracellular accumulation and transcytosis of saucer-shaped TNVs is higher in DutchAβ40 treated cells as compared to HBSS treated cells (FIG. 17E,F). More importantly, co-localization of red/green fluorescence which is indicative of selective targeting of TNVs to DutchAβ40-accumulated areas was predominant with saucer-shaped AF647-TNVs but not with spherical AF647-TNVs (FIG. 17D,F). These results clearly demonstrate the propensity of saucer-shaped AF647-TNVs but not spherical AF647-TNVs to target Aβ proteins accumulating in the endothelium. These results also indicate that the chitosan displayed on the TNV surface interacts with the extracellular matrix proteins and is expected to reduce the diffusion of TNVs away from the basement membrane. Moreover, the migration of TNVs into the brain parenchyma is expected to be limited due to the estimated 200-250 nm pore size of the basement membrane.

The amount of bound $^{125}$I in the $^{125}$I-TNV formulation was determined to be almost 80% (FIG. 18A). Consistent with QCM-D and laser confocal microscopy findings, no differences in the brain distribution of spherical $^{125}$I-TNVs in DutchAβ40-treated and control mice were seen (FIG. 18B), Alternatively, saucer-shaped $^{125}$I-TNVs distribution within the brain was 3.5 times higher in various brain regions of DutchAβ40-treated mice compared to saline-treated mice (FIG. 18C). DutchAβ40 peptide was allowed to circulate long enough (before injection of the TNVs) to ensure the majority is within the cerebrovasculature, but not long enough to permeate into the brain parenchyma. This provides us with a more cost-effective CAA model that tests the ability of TNVs in targeting CVA. The AUC in DutchAβ40-treated mice was 3 times lower than that of saline-treated mice (Table 3). In addition, the volume of distribution of saucer-shaped $^{125}$I-TNVs at the steady state (Vss) is significantly higher in DutchAβ40 treated mice than in control mice. These parameters suggest that in the presence of DutchAβ40, the plasma pharmacokinetics of saucer-shaped $^{125}$I-TNVs shift to match the known distribution profile of DutchAβ40.[25] Lastly, by controlling the interactions between oppositely charged polyplexes and allowing for the proper coverage of nanoparticle surface with chitosan, could prevent opsonisation and rapid removal of TNVs from systemic circulation. This affect can be partially seen from the reduced plasma clearance of saucer-shaped $^{125}$I-TNVs in the presence of DutchAβ40 treated mice as compared to saline treated mice.

MR imaging of saucer-shaped TNVs indicated high levels of contrast in the radiating arterioles in APP mice post-perfusion (FIG. 19A-D). This demonstrates the ability of saucer-shaped TNVs to bind and be retained by the endothelial cells within these arterioles. When hydrolysis of the saucer-shaped TNVs occurs, polycarbophil can swell in response to the changing environment and pH, which leads to increased water content and enhanced MRI signal. The MRI brain scans shown (FIG. 19C-D) were taken post-perfusion after a 3 hr saucer-shaped TNVs circulation timeframe. During this time, TNVs will still have access to water until their migration and internalization within endothelial cells, wherein they impart the dark contrast seen on the T2-weighted spin echo (SE) image. In addition to MRI, live dynamic SPECT imaging was performed, which showed a ~3.5 increase in brain uptake of saucer-shaped $^{125}$I-TNVs in APP mice as compared to WT mice (FIG. 19E). Although, dynamic SPECT imaging has lower resolution than MRI, it offers a great advantage of being more readily translatable to clinical CAA diagnosis. Finally, selectively targeting to the amyloid build-up in the arteries of APP was seen through the re-distribution and co-localization of the saucer-shaped AF647-TNVs with the amyloid deposits.

Conclusions

Disclosed herein are effectively designed TNVs capable of selectively targeting CVA deposits. These TNVs are small enough to transcytose endothelial cells, yet large enough to prevent their migration into the brain parencyhma. They are capable of serving as a multi-modal diagnostic tool for CAA through the use of MR, SPECT and fluorescent imaging. Therefore, based on the evidence provided, TNVs have demonstrated a high potential to serve both as diagnostic and therapeutic tools to detect and selectively target CVA while potentially slowing or even reverse the progression of this debilitating disease.

BIBLIOGRAPHY

1. Vinters H V, Gilbert J J 1983. Cerebral amyloid angiopathy: incidence and complications in the aging brain. II. The distribution of amyloid vascular changes. Stroke 14(6):924-928.
2. Calhoun M E, Burgermeister P, Phinney A L, Stalder M, Tolnay M, Wiederhold K H, Abramowski D, Sturchler-Pierrat C, Sommer B, Staufenbiel M, Jucker M 1999. Neuronal overexpression of mutant amyloid precursor protein results in prominent deposition of cerebrovascular amyloid. Proc Natl Acad Sci USA 96(24):14088-14093.
3. Chao C P, Kotsenas A L, Broderick D F 2006. Cerebral amyloid angiopathy: CT and MR imaging findings. Radiographics 26(5):1517-1531.
4. Knudsen K A, Rosand J, Karluk D, Greenberg S M 2001. Clinical diagnosis of cerebral amyloid angiopathy: validation of the Boston criteria. Neurology 56(4):537-539.
5. Greenberg S M, Vonsattel J P 1997. Diagnosis of cerebral amyloid angiopathy. Sensitivity and specificity of cortical biopsy. Stroke 28(7):1418-1422.
6. Greenberg S M, Briggs M E, Hyman B T, Kokoris G J, Takis C, Kanter D S, Kase C S, Pessin M S 1996. Apolipoprotein E epsilon 4 is associated with the presence and earlier onset of hemorrhage in cerebral amyloid angiopathy. Stroke 27(8):1333-1337.
7. Fountain N B, Lopes M B 1999. Control of primary angiitis of the CNS associated with cerebral amyloid angiopathy by cyclophosphamide alone. Neurology 52(3):660-662.
8. Poduslo J F, Ramakrishnan M, Holasek S S, Ramirez-Alvarado M, Kandimalla K K, Gilles E J, Curran G L, Wengenack T M 2007. In vivo targeting of antibody fragments to the nervous system for Alzheimer's disease immunotherapy and molecular imaging of amyloid plaques. J Neurochem 102(2):420-433.
9. Weksler B B, Subileau E A, Perriere N, Charneau P, Holloway K, Leveque M, Tricoire-Leignel H, Nicotra A, Bourdoulous S, Turowski P, Male D K, Roux F, Greenwood J, Romero I A, Couraud P O 2005. Blood-brain barrier-specific properties of a human adult brain endothelial cell line. FASEB journal: official publication of the Federation of American Societies for Experimental Biology 19(13):1872-1874.
10. Agyare E K, Curran G L, Ramakrishnan M, Yu C C, Poduslo J F, Kandimalla K K 2008. Development of a smart nano-vehicle to target cerebrovascular amyloid deposits and brain parenchymal plaques observed in Alzheimer's disease and cerebral amyloid angiopathy. Pharm Res 25(11):2674-2684.
11. Saha T K, Ichikawa H, Fukumori Y 2006. Gadolinium diethylenetriaminopentaacetic acid-loaded chitosan microspheres for gadolinium neutron-capture therapy. Carbohydr Res 341(17):2835-2841.
12. Shikata F, Tokumitsu H, Ichikawa H, Fukumori Y 2002. In vitro cellular accumulation of gadolinium incorporated into chitosan nanoparticles designed for neutron-capture therapy of cancer. Eur J Pharm Biopharm 53(1):57-63.
13. Poduslo J F, Hultman K L, Curran G L, Preboske G M, Chamberlain R, Marjanska M, Garwood M, Jack C R, Jr., Wengenack T M 2011. Targeting vascular amyloid in arterioles of Alzheimer disease transgenic mice with amyloid beta protein antibody-coated nanoparticles. Journal of neuropathology and experimental neurology 70(8): 653-661.
14. Poduslo J F, Curran G L, Wengenack T M, Malester B, Duff K 2001. Permeability of proteins at the blood-brain barrier in the normal adult mouse and double transgenic mouse model of Alzheimer's disease. Neurobiology of disease 8(4):555-567.
15. Muzzarelli R A 1998. Colorimetric determination of chitosan. Anal Biochem 260(2):255-257.
16. Wischke C, Borchert H H 2006. Increased sensitivity of chitosan determination by a dye binding method. Carbohydr Res 341(18):2978-2979.
17. Jaruszewski K M, Ramakrishnan S, Poduslo J F, Kandimalla K K 2012. Chitosan enhances the stability and targeting of immuno-nanovehicles to cerebro-vascular deposits of Alzheimer's disease amyloid protein. Nanomedicine: nanotechnology, biology, and medicine 8(2): 250-260.
18. Rowatt E, Williams R J 1989. The interaction of cations with the dye arsenazo III. Biochem J 259(1):295-298.
19. Fu R, Brey W W, Shetty K, Gor'kov P, Saha S, Long J R, Grant S C, Chekmenev E Y, Hu J, Gan Z, Sharma M, Zhang F, Logan T M, Bruschweller R, Edison A, Blue A, Dixon I R, Markiewicz W D, Cross T A 2005. Ultra-wide bore 900 MHz high-resolution NMR at the National High Magnetic Field Laboratory. Journal of magnetic resonance 177(1):1-8.
20. Hu Y, Jiang X, Ding Y, Ge H, Yuan Y, Yang C 2002. Synthesis and characterization of chitosan-poly(acrylic acid) nanoparticles. Biomaterials 23(15):3193-3201.
21. Lorenzo-Lamosa M L, Cuna M, Vila-Jato J L, Torres D, Alonso M J 1997. Development of a microencapsulated form of cefuroxime axetil using pH-sensitive acrylic polymers. J Microencapsul 14(5):607-616.
22. Poduslo J F, Curran G L, Haggard J J, Biere A L, Selkoe D J 1997. Permeability and residual plasma volume of human, Dutch variant, and rat amyloid beta-protein 1-40 at the blood-brain barrier. Neurobiol Dis 4(1):27-34.
23. Ramakrishnan M, Kandimalla K K, Wengenack T M, Howell K G, Poduslo J F 2009. Surface plasmon resonance binding kinetics of Alzheimer's disease amyloid beta peptide-capturing and plaque-binding monoclonal antibodies. Biochemistry 48(43):10405-10415.
24. Irvine J D, Takahashi L, Lockhart K, Cheong J, Tolan J W, Selick H E, Grove J R 1999. MDCK (Madin-Darby canine kidney) cells: A tool for membrane permeability screening. J Pharm Sci 88(1):28-33.
25. Agyare E, Leonard S, Curran G, Yu C, Lowe V, Paravastu A K, Poduslo J, Kandimalla K K 2012. Traffic jam at the blood brain barrier promotes greater accumulation of Alzheimer's disease amyloid-beta proteins in the cerebral vasculature. Mol Pharm.

Example 4

TNVs Trigger Controlled Immune Response and Stimulate the Clearance of Cerebrovascular Amyloid Recent passive immunization trials, despite falling short of reversing cognitive decline in AD patients, provided phenomenological observations on how amyloid clearance from the brain proceeds after the administration of anti-amyloid antibodies (Boche, Zotova et al. 2008). Some of those findings were: 1) the anti-amyloid antibodies that recognize the N-terminus of the Aβ protein are more effective in clearing the brain amyloid burden than those recognizing the C-terminus (Bard, Barbour et al. 2003); 2) the administration of the anti-amyloid antibody to the vascular wall, by-passing the BBB, accelerates cerebrovascular amyloid clearance (Prada, Garcia-Alloza et al. 2007, Thakker, Weatherspoon et al. 2009); 3) the administration of chitin to the vascular wall triggers the recruitment of perivascular macrophages from the periphery and enhances the clearance of cerebrovascular amyloid (Hawkes and McLaurin 2009); 4) immunization paradigms that stimulate Th2 response show less cerebrovascular inflammation and elicit greater amyloid clearance than those that provoke Th1 response. The Th2 response promotes antibody production, down-regulates pro-inflammatory Th1 responses, and results in the release of anti-inflammatory cytokines that have the potential to mitigate chronic inflammatory conditions in AD patients (Gelinas, DaSilva et al. 2004).

Figure 20:
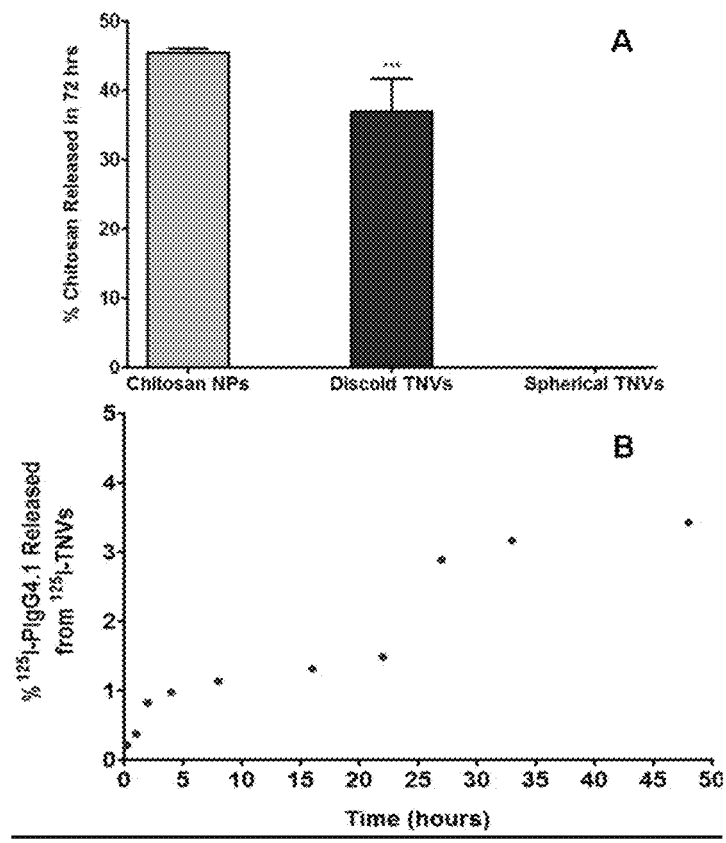
FIG. 20. Sustained release of chitosan and $^{125}$I-pIgG4.1 from the TNVs. A. Percent of chitosan released from various nanovehicles in 72 hours. Saucer-shaped vs spherical TNVs; Student's t-test (***p<0.001). B. Percent $^{125}$I-pIgG4.1 released from $^{125}$I-TNVs.

These observations were taken into account in the instant TNV design. Chitosan batch employed in formulating the TNVs has about 20-25% chitin. Furthermore, chitosan was shown to function as Th2 response triggering adjuvant in the immunization therapies. The native IgG4.1 binds to the N-terminal epitopes (2-10) on Aβ protein and can accelerate amyloid clearance from the brain. Additionally, the cyclophosphamide entrapped in the TNV is capable of subsiding Th1 response and enhance the Th2 response. All these components were delivered to the cerebrovascular basement membrane by the TNVs, and as demonstrated in the FIG. 20, the release of chitosan/chitin and pIgG4.1 can be sustained over a period of 3-5 days (FIG. 20) and the release of cyclophosphamide from the TNVs (4 µg/hr) followed Higuchi's √t profile for the first 24 hours. This approach avoids immune response in the brain, but triggers immunostimulation.

Example 5

Figure 21:
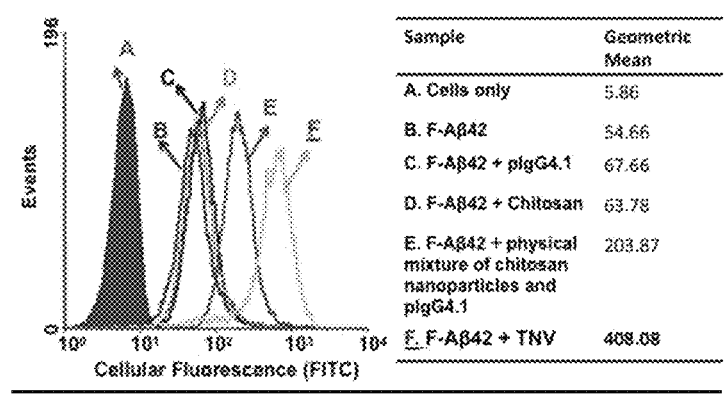
FIG. 21. Enhanced phagocytosis of fluoroscein isothiocyanate-Aβ42 (F-Aβ42) fibrils in monocytes in the present of various TNVs. G. M. denotes geometric mean.
Figure 22:
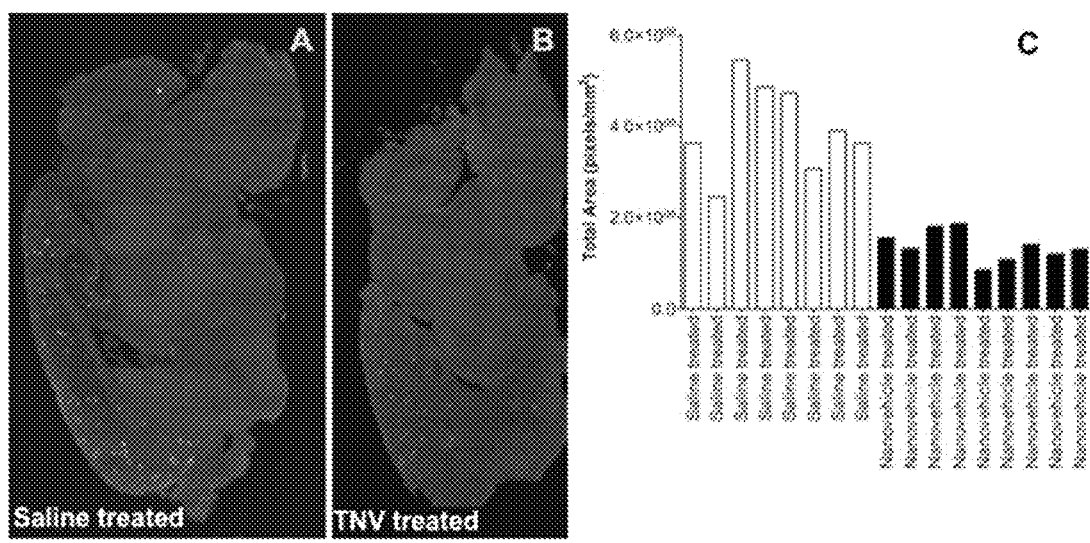
FIG. 22. Amyloid plaques (stained green by thioflavin S) in brain slice of the mouse treated with (A) saline and (B) theranostic nanovehicles (TNV). Quantification of the total plaque surface in saline and TNV treated mice. The bars in the graph represent the total plaque area in each slide as quantified using ImageJ software. A clear reduction in the plaque burden is evident in TNV treated mice compared to saline treated mice.

TNV Treatment Increases the Phagocytosis of Fluorescein Labeled Aβ42 (F-Aβ42) Fibrils by the U937 Pre-Monocytic Cells The human pre-monocytic cell line U937 is widely used as an in vitro model to investigate macrophage function (Lu and Pitha 2001). The effect of TNVs on the ability of U937 cells to phagocytose F-Aβ42 fibrils was investigated. The U937 cell suspension was incubated with F-Aβ42 fibrils for 30 min. To this mixture TNVs (1.15 mg/ml) were added. Incubation with pIgG4.1 (150 µg/ml), chitosan (0.75 mg/ml), physical mixture of pIgG4.1 (150 µg/ml), or chitosan nanoparticles or nanodiscs (1 mg/ml) served as controls. One hour following the incubation, the cells were harvested, washed thoroughly with HBSS, fixed in 4% paraformaldehyde and then analyzed by flow cytometry. The data presented in FIG. 21 shows that the phagocytosis of F-Aβ42 fibrils in the presence of TNVs increased by 8-fold than that in the presence of pIgG4.1 or chitosan.

Example 6

Maximizing the Sensitivity of Nanoprobes

Following IV bolus injection of Magnevist®-nanoprobes, cerebrovascular amyloid in AD transgenic mouse (APP,PS1) brain was detected ex vivo at high field strengths of 11.4 Tesla. However, amyloid imaging in live mice, against physiological motion, and at clinically approved field strengths may require further contrast enhancement. The sensitivity of detection can be increased by engineering the nanoprobe surface to accommodate: a) an array of agents such as Gd[DOTA] and $^{19}$F for higher MRI contrast and/or $^{64}$Cu-DOTA to generate greater specific activity for PET imaging; b) optimal cationic charge density to facilitate electrostatic interactions with negatively charged cerebrovascular endothelium (blood-brain barrier, BBB); and c) anti-amyloid antibody (IgG4.1) to target cerebrovascular amyloid.

Example 7

Ensuring the Specificity of Cerebrovascular Amyloid Detection

To be effective as CAA diagnostic agents, nanoprobes should demonstrate robust amyloid responsive cerebrovascular accumulation, but negligible uptake when the amyloid is absent. Based on data presented herein, this is achieved by enhancing the margination of nanoprobes from blood to the BBB along the Aβ concentration gradients and improving the migration of nanoprobes into the cerebrovascular basement membrane, where amyloid deposits are prevalent.

a) saucer-shaped nanoprobe with positive zeta potential, adequate buoyant density, and IgG4.1 grafted on its surface exhibits greater amyloid responsive margination to the BBB; and b) nanoprobe migration to the cerebrovascular basement membrane could be facilitated by: i) selectively disrupted BBB reported at the sites of amyloid deposition in the cerebral vasculature; ii) preferential binding of IgG4.1 to cerebrovascular amyloid deposits rich in fibrillar Aβ than to soluble Aβ circulating in the plasma; and iii) retention of nanoprobes >150 nm in the vascular wall without drifting into the brain parenchyma.

Example 8

Evaluating Nanoprobes' Biosafety/Efficacy in Transgenic Mice

Nanoprobes offer: i) sensitivity to detect cerebrovascular amyloid at a very young age in Tg-SwDI mice and to capture subsequent age-dependent increase in the vascular amyloid; and ii) specificity to detect cerebrovascular amyloid against the parenchymal amyloid burden in APP,PS1 mice. b) Nanoprobes are biocompatible, biodegradable, and cause no adverse reactions in vivo. Cyclophosphamide loaded in the nanocore, can quell potential cerebrovascular inflammation triggered by the nanoprobes.

Impact: By enabling the early detection of CAA, the multimodal nanoprobes can enhance the quality of life and life-span of CAA and AD patients as well as save millions of dollars in patient care costs.

The disclosures of each and every patent, patent application, and publication cited herein are hereby incorporated by reference herein in their entirety.

Headings are included herein for reference and to aid in locating certain sections. These headings are not intended to limit the scope of the concepts described therein under, and these concepts may have applicability in other sections throughout the entire specification.

While this invention has been disclosed with reference to specific embodiments, it is apparent that other embodiments and variations of this invention may be devised by others skilled in the art without departing from the true spirit and scope of the invention.

What is claimed is:

1. A method of treating a neurological disease and/or condition where accumulation of amyloid beta (Aβ) proteins have a role in the disease pathogenesis, the method comprising administering to a subject in need thereof an effective amount of a saucer shaped nanoparticle comprising chitosan cross-linked to polycarbophil, so as to treat the neurological disease, wherein the nanoparticle further comprises one or more therapeutic agents.

2. The method according to claim 1, wherein the disease and/or condition comprises cerebral amyloid angiopathy (CAA).

3. The method according to claim 1, wherein the disease and/or condition comprises Alzheimer's Disease, brain hemorrhage, vascular dysfunction, cerebrovascular inflammation, stroke and brain ischemia.

4. A method to treat cerebral inflammation in CAA comprising administering to a subject in need thereof an effective amount of a saucer shaped nanoparticle comprising chitosan cross-linked to polycarbophil, so as to treat cerebral inflammation in CAA, wherein the nanoparticle further comprises one or more therapeutic agents.

5. A method to detect accumulation of amyloid beta (Aβ) proteins comprising administering to a subject a saucer shaped nanoparticle comprising chitosan cross-linked to polycarbophil and imaging the subject's head, wherein the nanoparticle further comprises an imaging agent.

6. The method of claim 5, wherein the amyloid accumulation is detected in cerebral vasculature.

7. The method of claim 5, wherein the imaging is SPECT, MRI, PET, or fluorescent imaging.

8. The method of claim 1, further comprising one or more targeting moieties.

9. The method of claim 1, wherein the chitosan is about 5 to 16 fold excess to polycarbophil.

10. The method of claim 1, wherein the ratio of polycarbophil to chitosan is 1:5.

11. The method of claim 5, wherein the imaging agent is gadolinium, $^{19}F$, $^{125}I$, $^{99m}Tc$, $^{64}Cu$ or a fluorescent compound.

* * * * *